(12) United States Patent
Liu et al.

(10) Patent No.: US 10,323,037 B2
(45) Date of Patent: *Jun. 18, 2019

(54) AMINOPYRIDAZINONE COMPOUNDS AS PROTEIN KINASE INHIBITORS

(71) Applicant: Jiangsu Hengrui Medicine Co., Ltd., Lianyungang, Jiangsu (CN)

(72) Inventors: Dong Liu, Basking Ridge, NJ (US); Minsheng Zhang, Greenbrook, NJ (US); Qiyue Hu, Shanghai (CN)

(73) Assignee: JIANGSU HENGRUI MEDICINE CO., LTD., Jiangsu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/906,934

(22) Filed: Feb. 27, 2018

(65) Prior Publication Data

US 2018/0251465 A1 Sep. 6, 2018

Related U.S. Application Data

(63) Continuation of application No. 15/323,929, filed as application No. PCT/US2014/061393 on Oct. 20, 2014, now Pat. No. 9,951,077.

(60) Provisional application No. 62/021,421, filed on Jul. 7, 2014.

(51) Int. Cl.
*C07D 487/04* (2006.01)
*A61K 31/5025* (2006.01)

(52) U.S. Cl.
CPC .................. *C07D 487/04* (2013.01)

(58) Field of Classification Search
CPC .................................................. C07D 487/04
See application file for complete search history.

(56) References Cited

U.S. PATENT DOCUMENTS

| 8,673,925 B1 | 3/2014 | Goldstein | |
|---|---|---|---|
| 9,951,077 B2* | 4/2018 | Liu | C07D 487/04 |
| 2009/0209523 A1 | 8/2009 | Jones et al. | |
| 2013/0035325 A1 | 2/2013 | Taunton, Jr. et al. | |

FOREIGN PATENT DOCUMENTS

| WO | WO 2008/121742 A2 | 1/2008 |
|---|---|---|
| WO | WO 2008/039218 A1 | 4/2008 |
| WO | WO 2014/036016 A1 | 3/2014 |

OTHER PUBLICATIONS

Banker, Gilbert S. et al., "*Modern Pharmaceutics*," 3rd Ed. (1996), p. 596.
Berg, Leslie J., et al., "*TEC Family Kinases in T Lymphocyte Development and Function*," Annu. Rev. Immunol. vol. 23, (2005), pp. 549-600.
De Lucca, George V. et al., *Small Molecule Reversible Inhibitors of Bruton's Tyrosine Kinase (BTK): Structure-Activity Relationships Leading to the Identification of 7-(2-Hydroxypropan-2-yl)-4-[2-methyl-3-(4-dihydroquinazolin-3- yl)phenyl]-9H-Carbazole-1-Carboxamide (BMS-935177)*, J. Medicinal Chemistry, vol. 59, (2016), pp. 7915-7935.
Edwards, Jonathan C.W. et al., "*Efficacy of B-Cell-Targeted Therapy with Rituximab in Patients with Rheumatoid Arthritis*," N. Engl. J Med (2004), 350: pp. 2572-2581.
Favas, Catarina, et al., "*B-Cell-Depletion Therapy in SLE—What are the Current Prospects for Its Acceptance?*" Nature Reviews Rheumatology, vol. 5, (2009), pp. 711-716.
Hauser, Stephen L., et al., "*B-Cell Depletion with Rituximab in Relapsing-Remitting Multiple Sclerosis*," N. Engl J. Med., 358: (2008), pp. 676-688.
Honigberg, Lee A., et al., "*The Bruton Tyrosine Kinase Inhibitor PCI-32765 Blocks B-Cell Activation and is Efficacious in Models of Autoimmune Disease and B-Cell Malignancy*," PNAS, vol. 107, No. 29, (2010), pp. 13075-13080.
Meade, Eric A., et al., "*Synthesis, Antiproliferative, and Antiviral Activity of 4-Amino-1-(β-D-ribofuranosyl) Pyrrolo [2,3-d] Pyridazin-7 (6H)-One and Related Derivatives*," J. Med. Chem. vol. 36, (1993), pp. 3834-3842.
Mohamed, Abdala J., et al., "*Bruton's Tyrosine Kinase (BTK): Function, Regulation, and Transformation with Sepcial Emphasis on the PH Domain*," Immunological Reviews, vol. 228: (2009), pp. 58-73.
Ponader, Sabine, et al., "*The Bruton Tyrosine Kinase Inhibitor PCI-32765 Thwarts Chronic Lymphocytic Leukemia Cell Survival and Tissue Homing In Vitro and In Vivo*," Blood, vol. 119: No. 5, (2012), pp. 1182-1189.
Testa, Bernard, et al., "*Predicting Drug Metabolism: concepts and Challenges*," Pure Appl. Chem., vol. 76, No. 5, (2004), pp. 907-914.
Thomas, Jeffrey D., et al., "*Colocalization of X-Linked Agammaglobulinemia and X-Linked Immunodeficiency Genes*," Science, vol. 261, (1993), pp. 355-358.

(Continued)

Primary Examiner — Emily A Bernhardt
(74) Attorney, Agent, or Firm — Brinks Gilson & Lione; Yuezhong Feng

(57) ABSTRACT

The present disclosure provides a compound of formula (I) and the use thereof for the therapeutic treatment of human cancers including B-cell lymphoma and autoimmune diseases such as rheumatoid arthritis, systemic lupus erythematosus, and multiple sclerosis.

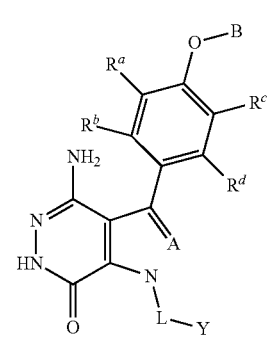

31 Claims, 2 Drawing Sheets

(56) References Cited

OTHER PUBLICATIONS

Wang, Xuehai et al., Chemical Abstract, vol. 165, No. 223974, Abstract for WO 2016/112637 (Jul. 2016).
Wolff, Manfred E., "*Burger's Medicinal Chemistry and Drug Discovery*," 5$^{th}$ Ed. vol. 1, Principles and Practice, ImmunoPharmaceutics, Inc., San Diego, CA (1995), pp. 975-977.
International Search Report to PCT/US2014/061393 (WO2016/007185A1), dated Jan. 8, 2015 (2p).
Extended European Search Report to European Application No. 14896967.8 dated Oct. 23, 2017, (12p).
Third Party Observation (53 pages) dated Dec. 13, 2018 out of corresponding European Application No. 14896967.8.
Pennington, Lewis D. et al., "The Necessary Nitrogen Atom: A Versatile High-Impact Design Element for Multiparameter Optimization", Journal of Medical Chemistry, 2017, vol. 60 (9), pp. 3552-3579.

\* cited by examiner

**: $p<0.01$, vs blank.

AMINOPYRIDAZINONE COMPOUNDS AS PROTEIN KINASE INHIBITORS

The present application is continuation of U.S. patent application Ser. No. 15/323,929, filed Jan. 4, 2017, which is the national phase of International Patent Application No. PCT/US2014/061393, filed on Oct. 20, 2014, which claims priority to U.S. Provisional Application No. 62/021,421, filed Jul. 7, 2014, all of which are hereby incorporated by reference herein.

TECHNICAL FIELD

The present invention describes a series of new compounds that display potent inhibition against Bruton's tyrosine kinase and, therefore, may provide a potential therapeutic approach to treating human cancers including B-cell lymphoma and autoimmune diseases such as rheumatoid arthritis, systemic lupus erythematosus, and multiple sclerosis.

BACKGROUND

Bruton's tyrosine kinase (Btk) is a non-receptor cytoplasmic tyrosine kinase belonging to the Tec family of kinases, members of which also include Tec, Itk, Txk, and Bmx. Most of these kinases are predominantly expressed in hematopoietic cells and play important roles in relaying signal transductions from cell surface receptors to direct cell development, differentiation, and other functions (Berg J J et al. Annual Review of Immunology, 2005; 23:549-600). Btk is critical for B cell development, differentiation, maturation, and signaling (Mohamed A J et al. Immunological Reviews, 2009; 228:58-73). Loss-of-function mutations of Btk cause X linked agammaglobulinemia (XLA) in humans and X linked immunodeficiency in mice (Thomas J D et al. Science 1993; 261:355-358). Patients with XLA have normal pre-B cell populations in their bone marrow but these cells fail to mature and enter the circulation. Therefore, these patients essentially have no circulating B cells and are incapable of producing antibodies.

BTK plays pivotal roles in B cell proliferation and activation mediated by B cell receptor (BCR). Upon BCR activation, Btk is translocated to the plasma membrane where it is phosphorylated and subsequently initiates a cascade of signaling events including activation of phospholipase Cγ2 (PLCγ2) and eventually leading to calcium mobilization and transcriptional regulation involving nuclear factor kappa B (NF κB) (Mohamed A J et al. Immunological Reviews 2009; 228:58-73). Because of the indispensable roles in BCR signaling pathway, it is believed that the kinase activity of Btk is critical for development and maintenance of a wide variety of B cell malignancies, including chronic lymphocytic leukemia (CLL) and a number of non-Hodgkin's lymphoma (NHL) subtypes, mantle cell lymphoma (MCL), and diffuse large B cell lymphoma (DLBCL) (Ponader S. et al. Blood 2012, 119:1182-1189; Honigberg L A et al. Proceedings of the National Academy of Sciences, 2010, 107:13075-13080). In addition, the role of B cell in the pathogenesis of rheumatoid arthritis, systemic lupus erythematosus, multiple sclerosis, and other immune disorders has been clinically demonstrated (Edwards J C et al. The New England Journal of Medicine, 2004, 350:2572-2581; Favas C et al. Nature Review Rheumatology, 2009, 5:711-716; Hauset S L et al. The New England Journal of Medicine, 2008, 358:676-688). Therefore, targeting Btk with small molecule inhibitors may provide therapeutic benefit for the treatment of B cell malignancies and autoimmune diseases.

SUMMARY

In one aspect, compounds are of formula (I), or pharmaceutically acceptable salts, solvates, hydrates, metabolites, or prodrugs thereof:

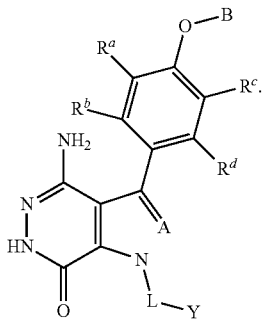

wherein:
A is selected from the group consisting of $CR^1$ and N; and wherein $R^1$ is selected from the group consisting of hydrogen, halogen, and unsubstituted or substituted alkyl;

$R^a$, $R^b$, $R^c$ and $R^d$ are independently selected from the group consisting of hydrogen, halogen, hydroxyl, nitro, cyano, unsubstituted or substituted alkyl, and unsubstituted or substituted alkoxyl;

B is selected from the group consisting of hydrogen, unsubstituted or substituted alkyl, unsubstituted or substituted cycloalkyl, unsubstituted or substituted heterocycloalkyl, unsubstituted or substituted aryl, and unsubstituted or substituted heteroaryl;

L is unsubstituted or substituted alkyl, or absent; and

Y is selected from the group consisting of unsubstituted or substituted cycloalkyl, unsubstituted or substituted heterocycloalkyl, unsubstituted or substituted aryl, and unsubstituted or substituted heteroaryl.

DETAILED DESCRIPTION

Figure 1:
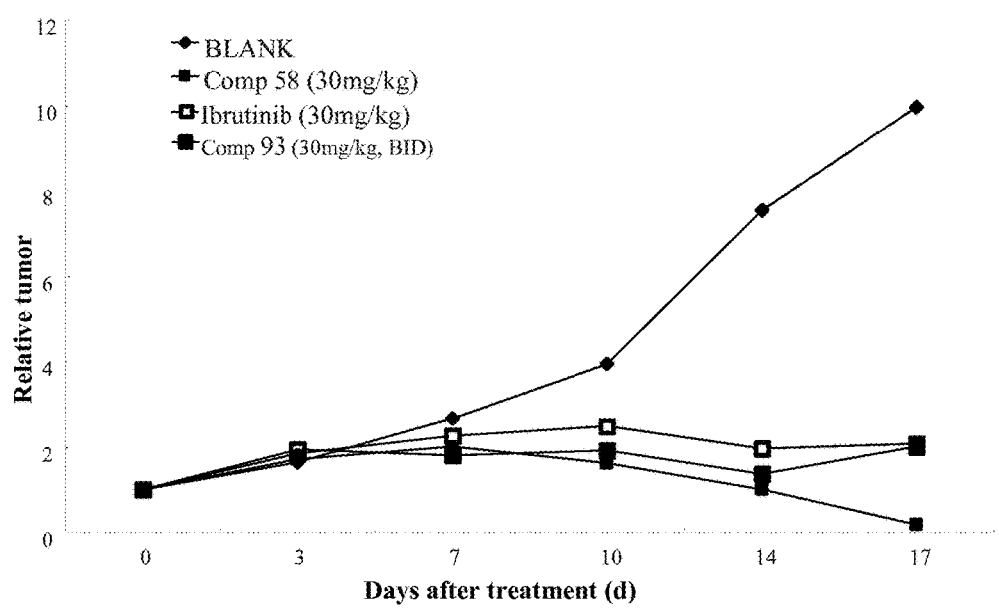
FIG. 1 illustrates effect of Btk inhibitors on tumor growth in TMD-8 xenograft model.
Figure 2:
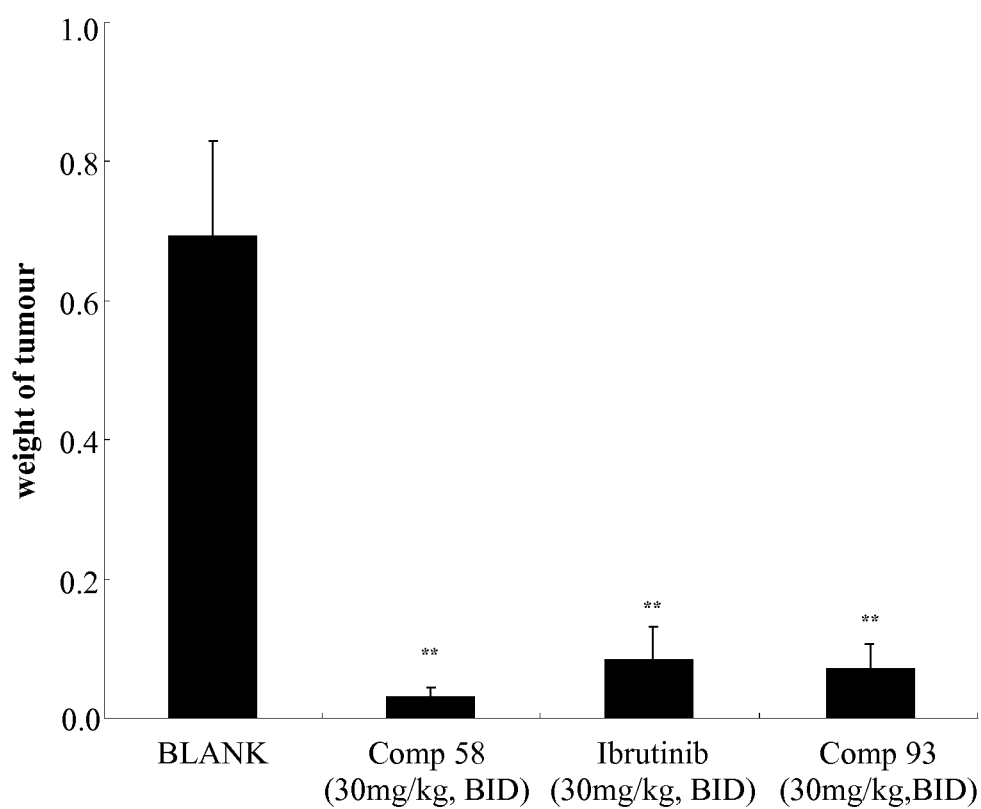
FIG. 2 illustrates effect of Btk inhibitors on tumor growth in TMD-8 xenograft model (final tumor weight).

This disclosure relates generally to compounds that modulate protein tyrosine kinase activity, methods of synthesizing, and using such compounds in therapeutic methods.

Definitions

Any terms in the present application, unless specifically defined, will take the ordinary meanings as understood by a person of ordinary skill in the art.

As used herein, the singular forms "a", "an", and "the" include plural reference unless the context clearly dictates otherwise.

Unless stated otherwise, all aryl, cycloalkyl, heteroaryl, and heterocyclyl groups of the present disclosure may be substituted as described in each of their respective definitions. For example, the aryl part of an arylalkyl group, such as benzyl, may be substituted as described in the definition of the term "aryl."

The term "alkoxy," as used herein, refers to a $C_1$-$C_{10}$, preferably $C_1$-$C_6$, alkyl group attached to the parent molecular moiety through an oxygen atom. Representative examples of alkoxy group include, but are not limited to, methoxy ($CH_3O—$), ethoxy ($CH_3CH_2O—$), and t-butoxy (($CH_3)_3CO—$).

The term "alkyl," as used herein, refers to a group derived from a straight or branched chain saturated hydrocarbon by removal of a hydrogen from one of the saturated carbons. The alkyl group preferably contains from one to ten carbon atoms, more preferably one to six carbon atoms. Representative examples of alkyl group include, but are not limited to, methyl, ethyl, isopropyl, and tert-butyl.

The term "aryl," as used herein, refers to a group derived from a $C_6$-$C_{12}$, preferably $C_6$-$C_{10}$, aromatic carbocycle by removal of a hydrogen atom from an aromatic ring. The aryl group can be monocyclic, bicyclic or polycyclic. Preferred examples of aryl groups include phenyl and naphthyl.

The term "cyano," as used herein, refers to —CN.

The term "cycloalkyl," as used herein, refers to a group derived from a monocyclic saturated carbocycle, having preferably three to eight, more preferably three to six, carbon atoms, by removal of a hydrogen atom from the saturated carbocycle. Representative examples of cycloalkyl groups include, but are not limited to, cyclopropyl, cyclopentyl, and cyclohexyl. When a cycloalkyl group contains one or more double bond(s) in the ring, yet not aromatic, it forms a "cycloalkenyl" group.

The terms "halo" and "halogen," as used herein, refer to F, Cl, Br, or I.

The term "haloalkoxy," as used herein, refers to a $C_1$-$C_6$, preferably $C_1$-$C_4$, haloalkyl group attached to the parent molecular moiety through an oxygen atom.

The term "haloalkyl," as used herein, refers to a $C_1$-$C_{10}$, preferably $C_1$-$C_6$, more preferably $C_1$-$C_4$, alkyl group substituted by at least one halogen atom. The haloalkyl group can be an alkyl group of which all hydrogen atoms are substituted by halogens. Representative examples of haloalkyl include, but are not limited to, trifluoromethyl ($CF_3—$), 1-chloroethyl ($ClCH_2CH_2—$), and 2,2,2-trifluoroethyl ($CF_3CH_2—$).

The term "heteroaryl," as used herein, refers to a 5- to 10-membered, monocyclic or bicyclic aromatic group comprising one or more, preferably one to three, heteroatoms independently selected from nitrogen, oxygen, and sulfur in the aromatic ring(s). As is well known to those skilled in the art, heteroaryl rings have less aromatic character than their all-carbon counterparts. Thus, for the purposes of the invention, a heteroaryl group need only have some degree of aromatic character. Illustrative examples of heteroaryl groups include, but are not limited to, pyridyl, pyridazinyl, pyrimidyl, pyrazyl, triazinyl, pyrrolyl, pyrazolyl, imidazolyl, pyrimidinyl, furyl, thienyl, isoxazolyl, thiazolyl, isoxazolyl, oxazolyl, indolyl, quinolinyl, isoquinolinyl, benzisoxazolyl, benzothiazolyl, and benzothienyl.

The term "heterocyclyl," as used herein, refers to a 3- to 10-membered monocyclic or bicyclic nonaromatic group comprising one or more, preferably one to three, heteroatoms independently selected from nitrogen, oxygen, and sulfur in the nonaromatic ring(s). The heterocyclyl groups of the present disclosure can be attached to the parent molecular moiety through a carbon atom or a nitrogen atom in the group. A heterocylcyl group can be saturated or unsaturated, for example, containing one or more double bond(s) in the ring. Examples of heterocyclyl groups include, but are not limited to, morpholinyl, oxazolidinyl, piperazinyl, piperidinyl, pyrrolidinyl, tetrahydrofuryl, thiomorpholinyl, and indolinyl, or the like.

The terms "hydroxy" or "hydroxyl," as used herein, refers to —OH.

The term "nitro," as used herein, refers to —$NO_2$.

The term "oxo," as used herein, refers to "=O".

When any group, for example, alkyl, alkenyl, "cycloalkyl," "aryl," "heterocyclyl," or "heteroaryl", is said to be "optionally substituted," unless specifically defined, it means that the group is or is not substituted by from one to five, preferably one to three, substituents independently selected from halogen, alkyl, alkoxy, haloalkyl, haloalkoxy, hydroxy, oxo, acyl, cyano, nitro, and amino group, or the like, provided that such substitution would not violate the conventional bonding principles known to a person of ordinary skill in the art. When the phrase "optionally substituted" is used before a list of groups, it means that each one of the groups listed may be optionally substituted.

The compounds of the present disclosure can exist as pharmaceutically acceptable salts or solvates. The term "pharmaceutically acceptable salt," as used herein, means any non-toxic salt that, upon administration to a recipient, is capable of providing the compounds or the prodrugs of a compound of this invention. The salts can be prepared during the final isolation and purification of the compounds or separately by reacting a suitable nitrogen atom with a suitable acid. Acids commonly employed to form pharmaceutically acceptable salts include inorganic acids such as hydrochloric acid, hydrobromic acid, hydroiodic acid, sulfuric acid, phosphoric acid, hydrogen bisulfide as well as organic acids, such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid, acetic acid acid, and related inorganic and organic acids.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include, but are not limited to, lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, and N-methylmorpholine.

The term "solvate," as used herein, means a physical association of a compound of this invention with one or more, preferably one to three, solvent molecules, whether organic or inorganic. This physical association includes hydrogen bonding. In certain instances the solvate will be capable of isolation, for example when one or more, preferably one to three, solvent molecules are incorporated in the crystal lattice of the crystalline solid. Exemplary solvates include, but are not limited to, hydrates, ethanolates, methanolates, and isopropanolates. Methods of solvation are generally known in the art.

The term "therapeutically effective amount," as used herein, refers to the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially, or simultaneously.

The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

The term "patient" includes both human and other mammals.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

In one embodiment, compounds are of formula (I), or pharmaceutically acceptable salts, solvates, hydrates, metabolites, or prodrugs thereof:

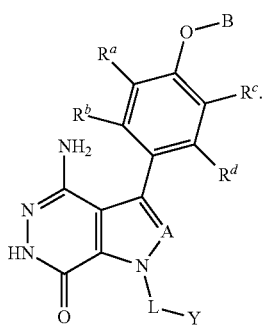

I wherein:

A is selected from the group consisting of $CR^1$ and N; and wherein $R^1$ is selected from the group consisting of hydrogen, halogen, and unsubstituted or substituted alkyl;

$R^a$, $R^b$, $R^c$ and $R^d$ are independently selected from the group consisting of hydrogen, halogen, hydroxyl, nitro, cyano, unsubstituted or substituted alkyl, and unsubstituted or substituted alkoxyl;

B is selected from the group consisting of hydrogen, unsubstituted or substituted alkyl, unsubstituted or substituted cycloalkyl, unsubstituted or substituted heterocycloalkyl, unsubstituted or substituted aryl, and unsubstituted or substituted heteroaryl;

L is unsubstituted or substituted alkyl, or absent; and

Y is selected from the group consisting of unsubstituted or substituted cycloalkyl, unsubstituted or substituted heterocycloalkyl, unsubstituted or substituted aryl, and unsubstituted or substituted heteroaryl.

In some embodiments, A is selected from the group consisting CH, CF, CCl and N.

In some embodiments, at least one of $R^a$, $R^b$, $R^c$ and $R^d$ is selected from the group consisting of hydrogen, F, Cl, and methoxyl. In some embodiments, $R^a$, $R^b$, $R^c$ and $R^d$ are hydrogen. In some embodiments, $R^a$ is F, Cl, or methoxyl. In some embodiments, $R^d$ is F, Cl, or methoxyl.

In some embodiments, B is unsubstituted or substituted $C_1$-$C_6$ alkyl In some embodiments, B is unsubstituted or substituted aryl. In some embodiments, B is unsubstituted or substituted phenyl. In some embodiments, B is phenyl. In some embodiments, B is phenyl substituted with at least one member selected from the group consisting of halogen, cyano, nitro, hydroxyl, unsubstituted or substituted alkyl, unsubstituted or substituted alkoxy, —$NR^1R^2$, —$C(O)R^3$, —$C(O)OR^4$, —$C(O)NHR^5$, and —$S(O)_2R^6$. $R^1$ and $R^2$ are independently selected from the group consisting of hydrogen, unsubstituted or substituted alkyl, —$C(O)R^7$, —$C(O)OR^8$, —$C(O)NHR^9$, —$S(O)_2R^{10}$; and wherein $R^3$, $R^4$, $R^5$, $R^6$, $R^7$, $R^8$, $R^9$, and $R^{10}$ are independently selected from the group consisting of unsubstituted or substituted alkyl, unsubstituted or substituted cycloalkyl, unsubstituted or substituted heterocycloalkyl, unsubstituted or substituted aryl, and unsubstituted or substituted heteroaryl.

In some embodiments, B is phenyl substituted with at least one member selected from the group consisting of F, Cl, and methoxyl. In some embodiments, B is phenyl substituted with two F. In some embodiments, B is phenyl substituted with two Cl. In some embodiments, B is phenyl substituted with one Cl and one methoxyl.

In some embodiments, L is absent. In some embodiments, L is methylene.

In some embodiments, Y is selected from the group consisting of unsubstituted or substituted piperidinyl, unsubstituted or substituted phenyl, unsubstituted or substituted bicyclo[3.2.1]octanyl, unsubstituted or substituted azetidinyl, and unsubstituted or substituted pyrrolidinyl. In some embodiments, Y is substituted with at least one member selected from the group consisting of halogen, —CN, —$C(O)R^{11}$, —$NHC(O)R^{12}$, —$S(O)_2R^{13}$, and —$NHS(O)_2R^{14}$; and wherein $R^{11}$, $R^{12}$, $R^{13}$, and $R^{14}$ are independently selected from the group consisting of unsubstituted or substituted alkyl, unsubstituted or substituted cycloalkyl, unsubstituted or substituted alkenyl, unsubstituted or substituted cycloalkenyl, and unsubstituted or substituted alkynyl.

In some embodiments, Y is substituted with at least one member selected from the group consisting of F, CN, —C(O)CH=$CH_2$, —C(O)CH=$CHCH_2N(CH_3)_2$, —NHC(O)CH=$CH_2$, —NHC(O)CH=$CHCH_2N(CH_3)_2$, —C(O)CH=$CHCH_2N(CH_3)(COOC(CH_3)_3)$; —C(O)CH=$CHCH_2NH(CH_3)$, —C(O)$CH_2CH_3$, —C(O)$CH_2CH_2CH_3$,

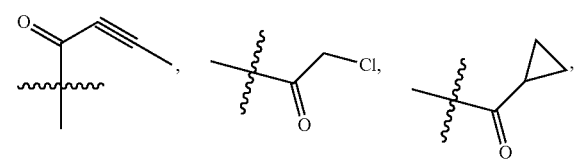

—C(O)$CH_2CN$,

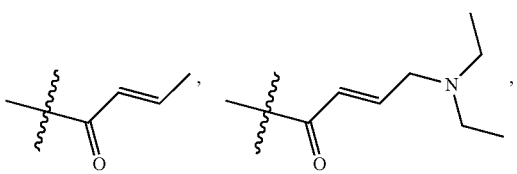

-continued

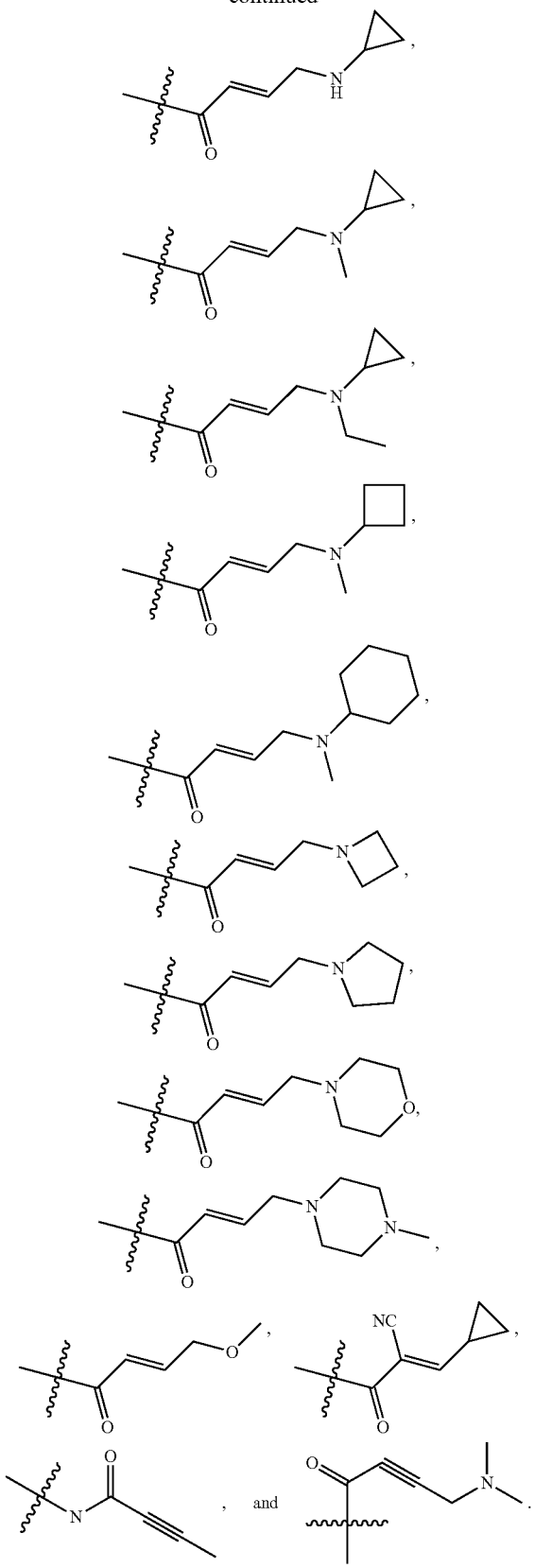

In some embodiments, the compound has both S-form and R-form. In some embodiments, the compound has more R-form than S-form. In some embodiments, the compound has more S-form than R-form.

In some embodiments, the compound has a structure of formula (II):

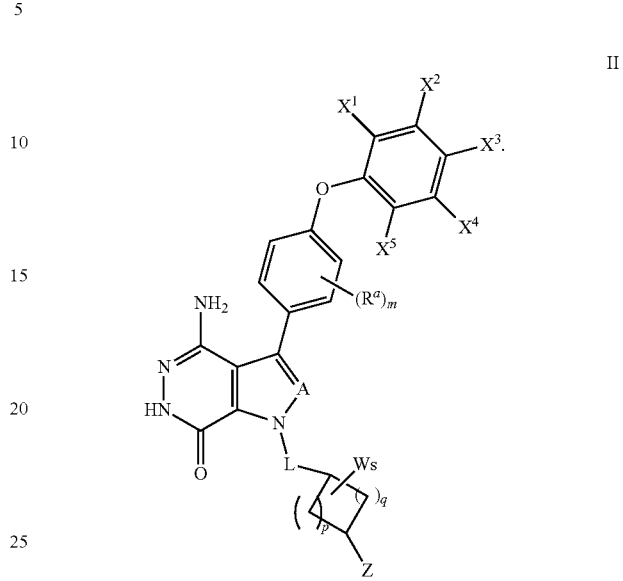

II where $R^a$, A, and L are defined as in formula (I);

$X^1$, $X^2$, $X^3$, $X^4$, and $X^5$ are independently selected from the group consisting of hydrogen, halogen, cyano, nitro, hydroxyl, unsubstituted or substituted alkyl, unsubstituted or substituted alkoxy, —$NR^1R^2$, —$C(O)R^3$, —$C(O)OR^4$, —$C(O)NHR^5$, and —$S(O)_2R^6$;

wherein $R^1$ and $R^2$ are independently selected from the group consisting of hydrogen, unsubstituted or substituted alkyl, —$C(O)R^7$, —$C(O)OR^8$, —$C(O)NHR^9$, —$S(O)_2R^{10}$; and wherein $R^3$, $R^4$, $R^5$, $R^6$, $R^7$, $R^8$, $R^9$, and $R^{10}$ are independently selected from the group consisting of unsubstituted or substituted alkyl, unsubstituted or substituted cycloalkyl, unsubstituted or substituted heterocycloalkyl, unsubstituted or substituted aryl, and unsubstituted or substituted heteroaryl;

W is selected from the group consisting of halogen, hydroxyl, unsubstituted or substituted alkyl, and unsubstituted or substituted alkoxyl; wherein two W may combine with an atom or atoms to which they are attached to form unsubstituted or substituted $C_{3-12}$ cycloalkyl, unsubstituted or substituted 3- to 12-membered heterocyclic, unsubstituted or substituted $C_{6-12}$ aryl, or unsubstituted or substituted 5- to 12-membered heteroaryl;

m=0, 1, 2, or 3;
p=1, 2, or 3;
q=0, 1, or 2;
s=0, 1, 2, or 3; and

Z is selected from the group consisting of —$NHC(O)R^{12}$, and —$NHS(O)_2R^{14}$; and wherein $R^{12}$, and $R^{14}$ are independently selected from the group consisting of unsubstituted or substituted alkyl, unsubstituted or substituted cycloalkyl, unsubstituted or substituted alkenyl, unsubstituted or substituted cycloalkenyl, and unsubstituted or substituted alkynyl.

In some embodiments, A is N, CH, CF or CCl. In some embodiments, L is absent or —$CH_2$—. In some embodiments, p and q are independently 1 or 2. In some embodiments, s is 1 or 2.

In some embodiments, Z is selected from the group consisting of —NHC(O)CH═CH₂, —NHC(O)CH═CHCH₂N(CH₃)₂, and

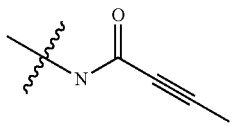

In some embodiments, the compound has a structure of formula (III):

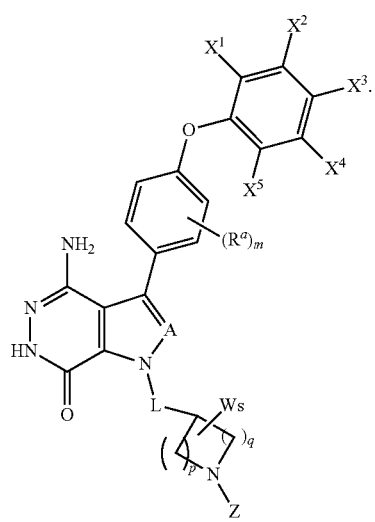

III where Rᵃ, A, L, X¹, X², X³, X⁴, X⁵, W, p, q, s and m are defined as above.

Z is selected from —CN, —C(O)R¹¹ and —S(O)₂R¹³; and wherein R¹¹ and R¹³ are independently selected from the group consisting of unsubstituted or substituted alkyl, unsubstituted or substituted cycloalkyl, unsubstituted or substituted alkenyl, unsubstituted or substituted cycloalkenyl, and unsubstituted or substituted alkynyl.

In some embodiments, Z is selected from the group consisting of CN, —C(O)CH═CH₂, —C(O)CH═CHCH₂N(CH₃)₂, —C(O)CH═CHCH₂N(CH₃)(COOC(CH₃)₃; —C(O)CH═CHCH₂NH(CH₃), —C(O)CH₂CH₃, —C(O)CH₂CH₂CH₃,

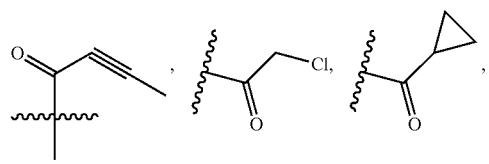

—C(O)CH₂CN,

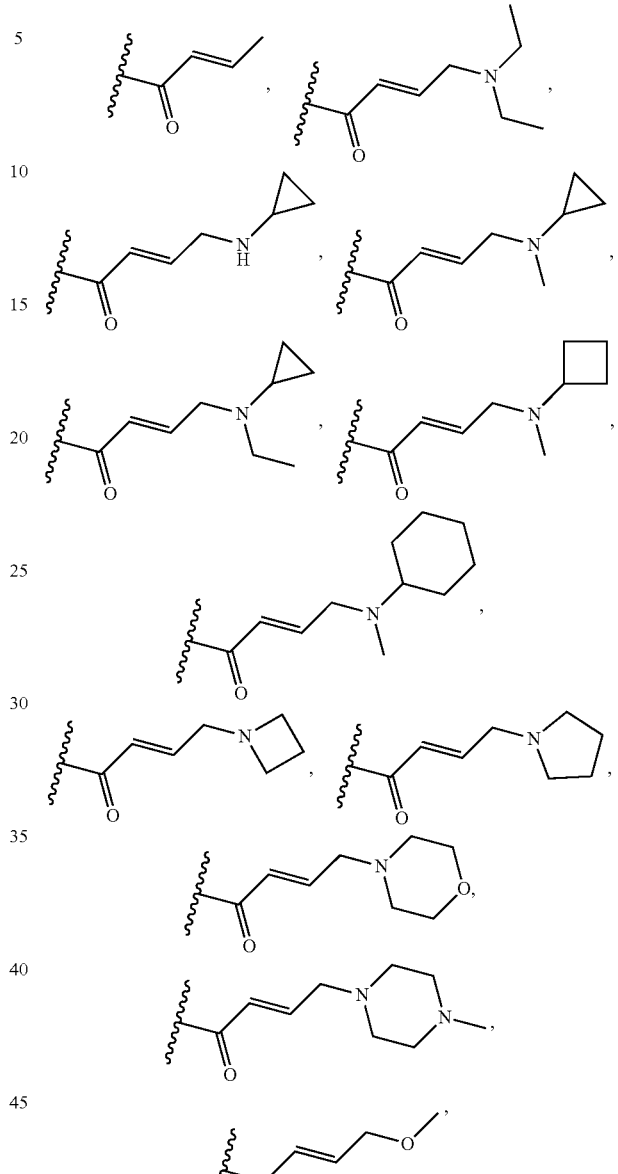

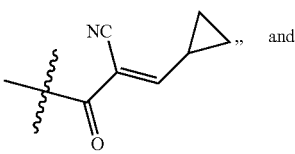

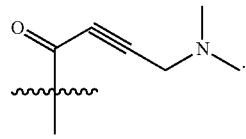

In some embodiments, the compound has formula (IV):

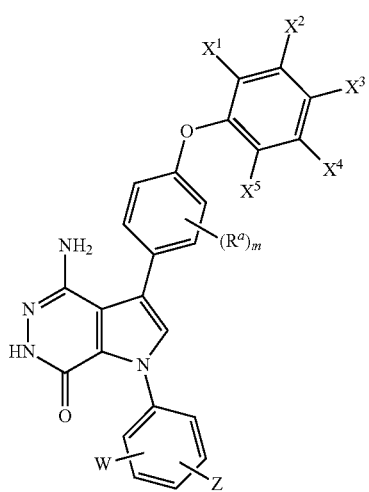

IV where $R^a$, $X^1$, $X^2$, $X^3$, $X^4$, $X^5$, W, Z, and m are defined as above.

In some embodiments, Z is selected from the group consisting of —NHC(O)$R^{12}$ and —NHS(O)$_2R^{14}$.

In some embodiments, the compound has formula (V):

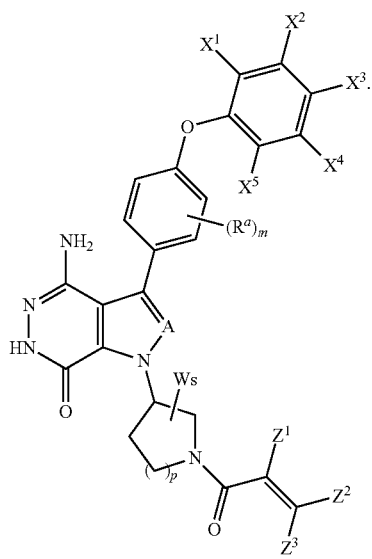

V where $R^a$, A, $X^1$, $X^2$, $X^3$, $X^4$, $X^5$, W, s, and m are defined as above;

$Z^1$ is selected from the group consisting of hydrogen, halogen, cyano, and unsubstituted or substituted alkyl; and $Z^2$ and $Z^3$ are independently selected from the group consisting of hydrogen, unsubstituted or substituted alkyl, unsubstituted or substituted cycloalkyl, unsubstituted or substituted heterocycloalkyl, —CH$_2$O$R^{15}$, and —CH$_2$N$R^{16}R^{17}$;

$R^{15}$ and $R^{16}$ are independently selected from the group consisting of hydrogen, unsubstituted or substituted alkyl, unsubstituted or substituted cycloalkyl, and unsubstituted or substituted heterocycloalkyl; $R^{17}$ is selected from the group consisting of unsubstituted or substituted alkyl, unsubstituted or substituted cycloalkyl, unsubstituted or substituted aryl, and unsubstituted or substituted heteroaryl, —C(O)$R^{18}$, —C(O)O$R^{19}$, and —S(O)$_2R^{20}$; wherein $R^{18}$, $R^{19}$ and $R^{20}$ are independently selected from the group consisting of unsubstituted or substituted alkyl, and unsubstituted or substituted cycloalkyl;

$R^{16}$ and $R^{17}$ combine with N to which they are attached to form unsubstituted or substituted 3- to 12-membered heterocyclic, or unsubstituted or substituted 5- to 12-membered heteroaryl; and $Z^1$ and $Z^2$ can join together to form a bond or combine with atoms to which they are attached to form unsubstituted or substituted C$_{5-12}$ cycloalkenyl, unsubstituted or substituted 5- to 12-membered heterocyclic, unsubstituted or substituted C$_{6-12}$ aryl, or unsubstituted or substituted 5- to 12-membered heteroaryl.

In some embodiments, A is selected from the group consisting of CH, CF and CCl.

In some embodiments, $Z^1$, $Z^2$ and $Z^3$ are H. In some embodiments, $Z^1$ and $Z^2$ join together to form a bond. In some embodiments, $Z^1$ and $Z^3$ are hydrogen, $Z^2$ is —CH$_2$N$R^{16}R^{17}$.

In some embodiments, 3 or less than 3 of $X^1$, $X^2$, $X^3$, $X^4$, and $X^5$ are halogen. In some embodiments, $X^1$ is F. In some embodiments, $X^2$, $X^3$, and $X^4$ are hydrogen. In some embodiments, $X^5$ is selected from the group consisting of H, F and Cl.

Although all of the above structure formulas were drawn as certain isomers for convenience, the present invention may include all isomers, such as, tautomers, rotamers, geometric isomers, diastereomers, racemates, and enantiomers.

Tautomers are constitutional isomers of organic compounds that readily interconvert by a chemical reaction called tautomerization. This reaction commonly results in the formal migration of a hydrogen atom or proton, accompanied by a switch of a single bond and adjacent double bond. A couple of the common tautomeric pairs are: ketone-enol, lactam-lactim. An example of lactam-lactim equilibria is between A and B as shown below

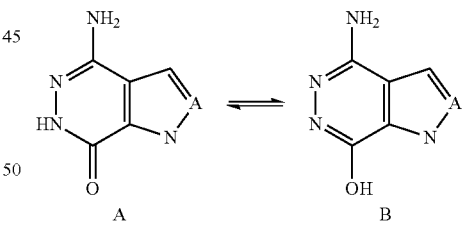

All the compounds in the present disclosure can be drawn as either form A or form B. All tautomeric forms are included in the scope of the invention. The naming of the compounds does not exclude any tautomers.

Pharmaceutical compositions or formulations of the present invention include those suitable for oral, nasal, topical (including buccal and sublingual), rectal, vaginal and/or parenteral administration. Regardless of the route of administration selected, the active ingredient(s) are formulated into pharmaceutically acceptable dosage forms by methods known to those of skill in the art.

The amount of the active ingredient(s) which will be combined with a carrier material to produce a single dosage form will vary depending upon the host being treated, the particular mode of administration and all of the other factors described above. The amount of the active ingredient(s) which will be combined with a carrier material to produce a single dosage form will generally be that amount of the active ingredient(s) which is the lowest dose effective to produce a therapeutic effect.

Methods of preparing pharmaceutical formulations or compositions include the step of bringing the active ingredient(s) into association with the carrier and, optionally, one or more accessory ingredients. In general, the formulations are prepared by uniformly mixing the active ingredient(s) into liquid carriers, or finely divided solid carriers, or both, and then, if necessary, shaping the product.

Exemplary, non-limiting examples of formulations of the disclosure suitable for oral administration may be in the form of capsules, cachets, pills, tablets, lozenges (using a flavored basis, usually sucrose and acacia or tragacanth), powders, granules, or as a solution or a suspension in an aqueous or nonaqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of the active ingredient(s).

In solid dosage forms of the invention for oral administration (capsules, tablets, pills, dragees, powders, granules and the like), the prodrug(s), active ingredient(s) (in their micronized form) is/are mixed with one or more pharmaceutically-acceptable carriers known to those of skill in the art. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof. Proper fluidity can be maintained, for example, by the use of coating materials, such as lecithin, by the maintenance of the required particle size, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monostearate and gelatin.

In some cases, in order to prolong the effect of the active ingredient(s), it is desirable to slow the absorption of the drug from subcutaneous or intramuscular injection. This may be accomplished by the use of a liquid suspension of crystalline or amorphous material having poor water solubility. The rate of absorption of the active ingredient(s) then depends upon its/their rate of dissolution which, in turn, may depend upon crystal size and crystalline form.

The formulations may be presented in unit-dose or multi-dose sealed containers, for example, ampoules and vials, and may be stored in a lyophilized condition requiring only the addition of the sterile liquid carrier, for example water for injection, immediately prior to use. Extemporaneous injection solutions and suspensions maybe prepared from sterile powders, granules and tablets of the type described above.

The present disclosure includes a method of modulating protein tyrosine kinase activity, comprising contacting a cell with an effective amount of any compound of formulae (I)-(V) or the pharmaceutically acceptable salt thereof.

The present disclosure includes a method of treating a condition or a disease mediated by protein tyrosine kinase, comprising administering to a subject a therapeutically effective amount of any compound of formulae (I)-(V), or the pharmaceutically acceptable salt thereof. In some embodiments, the condition or the disease is cancer or autoimmune diseases. In some embodiments, the cancer is B-cell malignancies. In some embodiments, the cancer is chronic lymphocytic leukemia (CLL), mantle cell lymphoma (MCL), diffuse large B-cell lymphoma (DLBCL), multiple myeloma (MM), follicular lymphoma (FL), armginal zone lymphoma and waldenström's macroglobulinemia (WM). In some embodiments, the autoimmune disease is rheumatoid arthritis. In some embodiments, the autoimmune disease is systemic lupus erythematosus.

Synthetic Methods

Abbreviations

Abbreviations which have been used in the descriptions of the schemes and the examples that follow are:
Cy for cyclohexane
DAST for diethylaminosulfur trifluoride;
DCM for dichloromethane;
DIEA or DIPEA for diisopropyl ethylamine;
DMAP for N,N-dimethylaminopyridine;
DME for ethylene glycol dimethyl ether;
DMF for N,N-dimethyl formamide;
DMSO for dimethylsulfoxide;
DPPA for diphenoxyphosphoryl azide;
EDCI or EDC for 1-(3-diethylaminopropyl)-3-ethylcarbodiimide hydrochloride;
ESI for electrospray ionization;
Et for ethyl;
EtOAc for ethyl acetate;
g for gram(s);
h for hour(s);
HATU for O-(7-Azabenzotriazole-1-yl)-N,N,N',N'-tetramethyluronium hexafluoro-phosphate;
HBTU for O-Benzotriazole-N,N,N',N'-tetramethyl-uronium-hexafluoro-phosphate;
HPLC for high-performance liquid chromatography;
mCPBA for 3-Chloroperbenzoic acid;
Me for methyl;
MeOH for methanol;
mg for milligram(s);
min for minute(s);
MS for mass spectrometry;
NBS for N-Bromosuccinimide;
NCS for N-Chlorosuccinimide;
NMR for nuclear magnetic resonance;
Pd(dppf)Cl$_2$ for [1,1'-Bis(diphenylphosphino)ferrocene]dichloropalladium(II);
Pd$_2$(dba)$_3$ for Tris(dibenzylideneacetone)dipalladium(0);
PG for protecting groups;
Ph for phenyl;
PPh$_3$ for triphenylphosphine;
rt for room temperature;
TEA for triethyl amine;
TFA for trifluoroacetic acid;
THF for tetrahydrofuran;
TLC for thin layer chromatography; and
tBOC or Boc for tert-butyloxy carbonyl.

The compounds and processes of the present invention will be better understood in connection with the following synthetic schemes that illustrate the methods by which the compounds of the invention may be prepared. Other reaction schemes could be readily devised by those skilled in the art.

Scheme 1

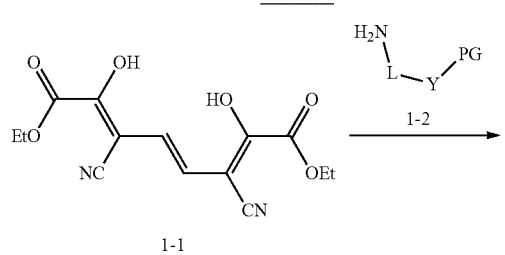

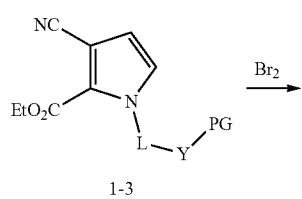

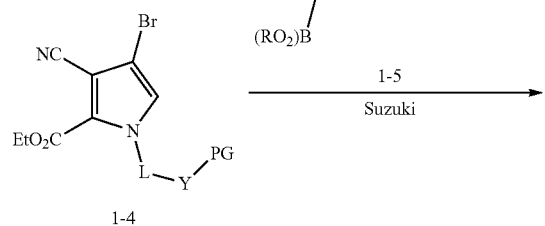

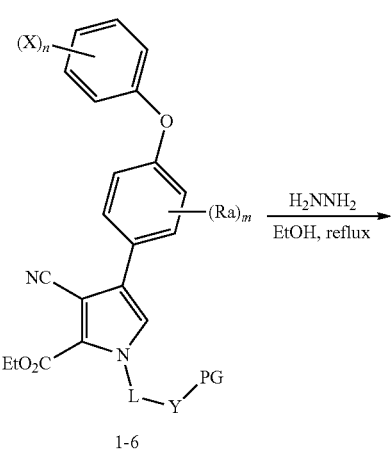

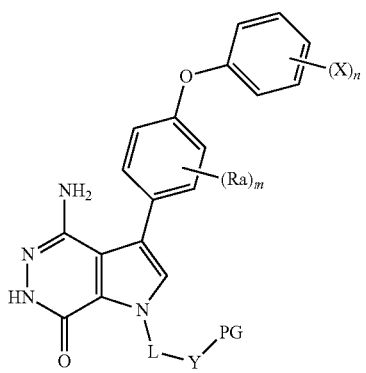

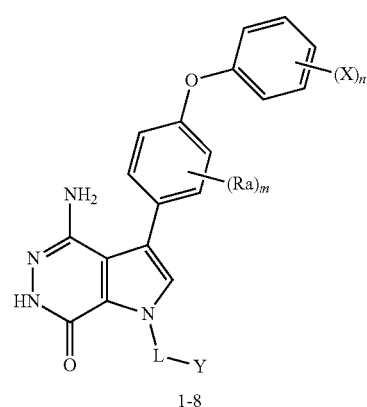

Triene 1-1 and amine 1-2 stirred in organic solvents (e.g. EtOAc) at elevated temperature to afford pyrrole 1-3. Bromination with Br₂ or other proper reagents gave bromide 1-4, which reacted with readily available bronic acid or bronic ester 1-5 under Suzuki reaction conditions to give 1-6. Ester 1-6 and hydrazine refluxed in EtOH gave key intermediate 1-7. Deprotection and Z installation yielded 1-8.

Scheme 2

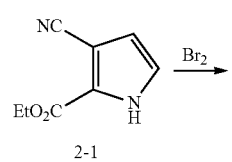

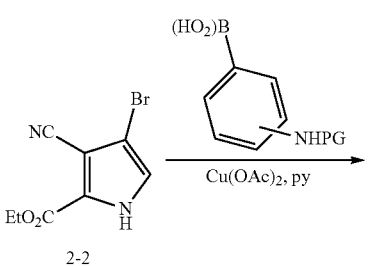

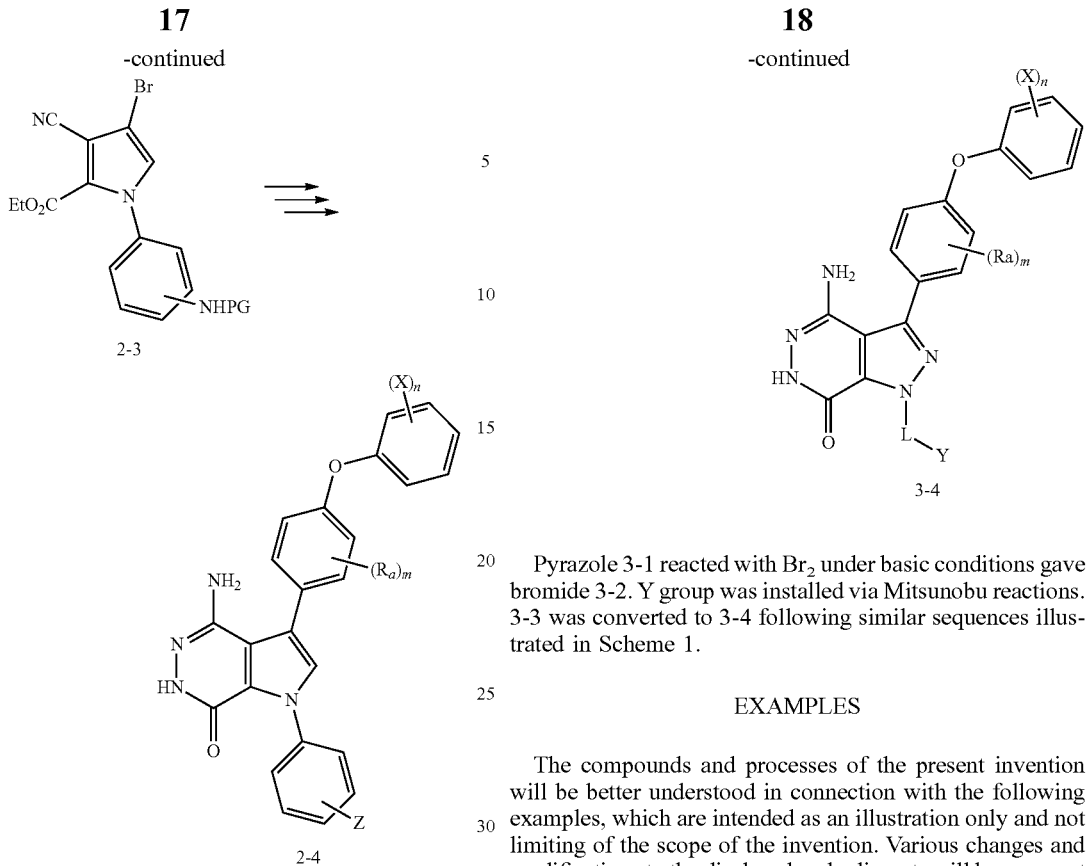

Pyrazole 3-1 reacted with Br$_2$ under basic conditions gave bromide 3-2. Y group was installed via Mitsunobu reactions. 3-3 was converted to 3-4 following similar sequences illustrated in Scheme 1.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, relating to the chemical structures, substituents, derivatives, formulations and/or methods of the invention may be made without departing from the spirit of the invention and the scope of the appended claims.

Example 1

(R)-1-(1-acryloylpiperidin-3-yl)-4-amino-3-(4-phenoxyphenyl)-1H-pyrrolo[2,3-d]pyridazin-7(6H)-one Alternatively, pyrrole 2-1 without N substitute was prepared, followed by bromination to afford bromide 2-2. The aromatic ring was installed via copper catalyzed C—N cross-coupling reactions. The resulting intermediate 2-3 was transformed to final compound 2-4 via similar sequences illustrated in Scheme 1.

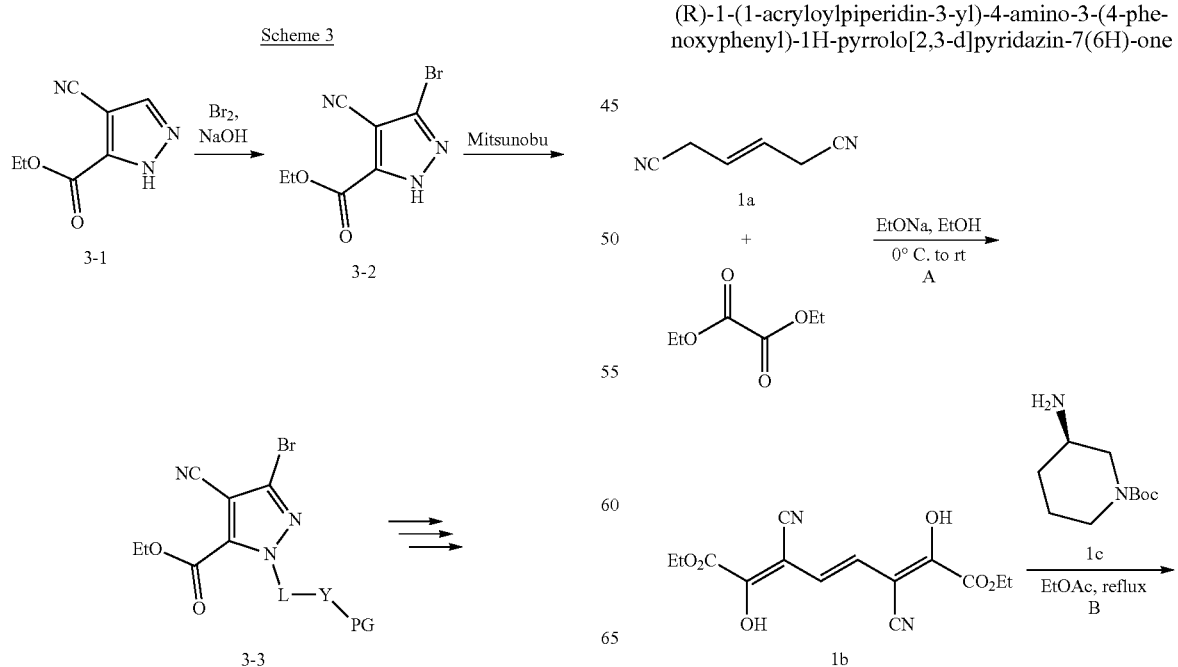

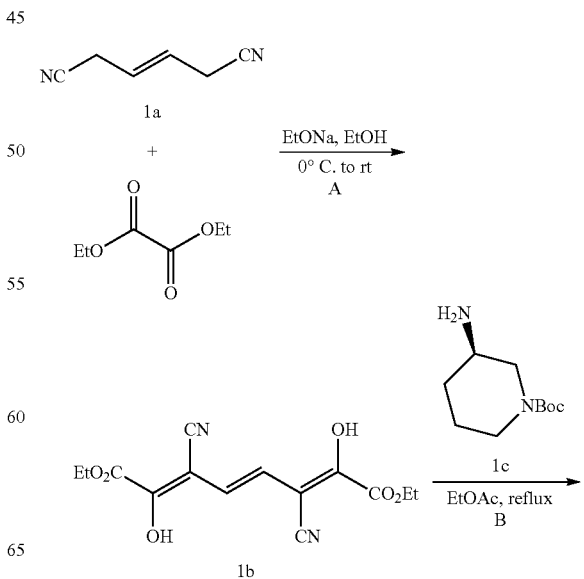

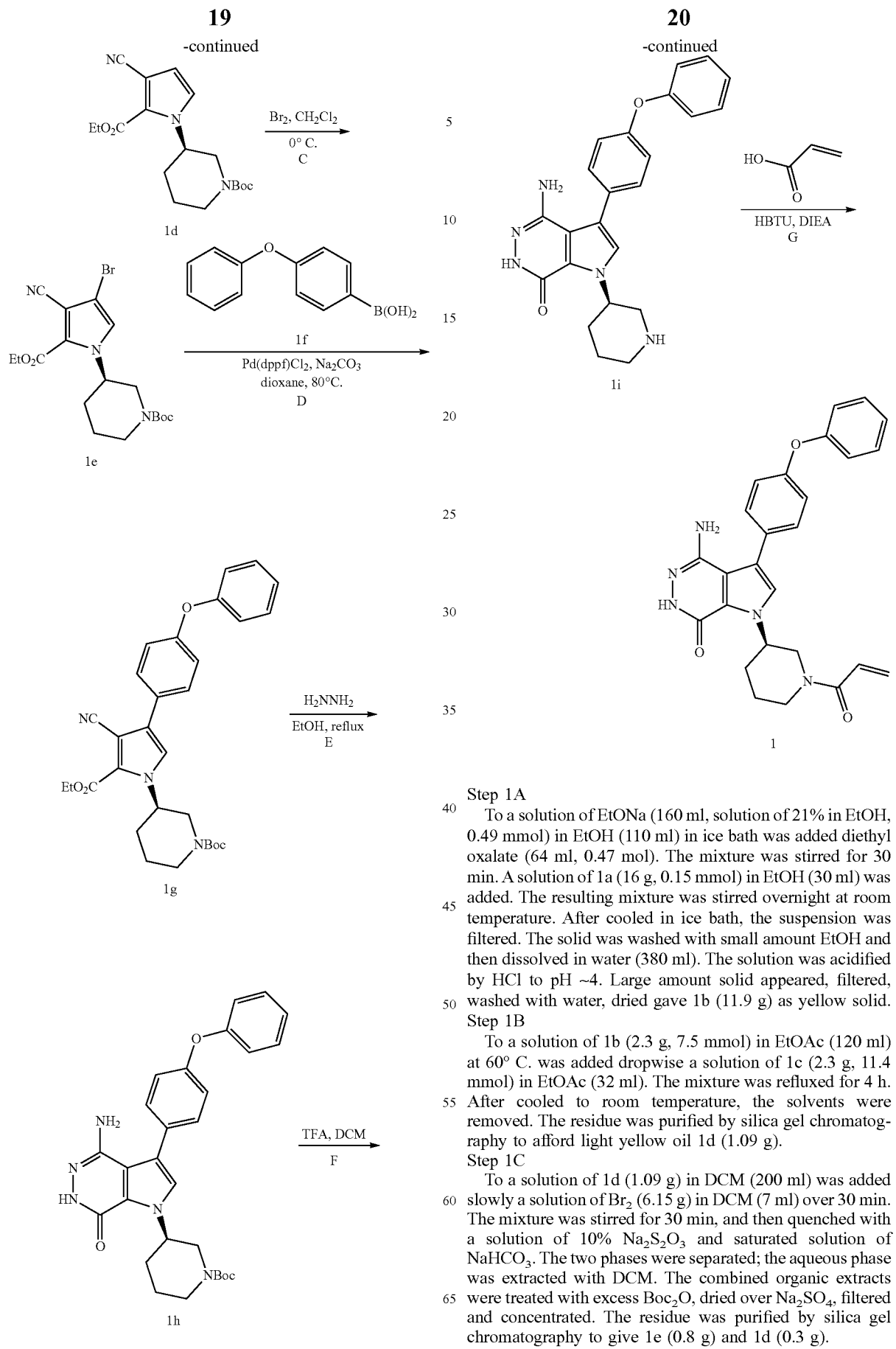

Step 1A

To a solution of EtONa (160 ml, solution of 21% in EtOH, 0.49 mmol) in EtOH (110 ml) in ice bath was added diethyl oxalate (64 ml, 0.47 mol). The mixture was stirred for 30 min. A solution of 1a (16 g, 0.15 mmol) in EtOH (30 ml) was added. The resulting mixture was stirred overnight at room temperature. After cooled in ice bath, the suspension was filtered. The solid was washed with small amount EtOH and then dissolved in water (380 ml). The solution was acidified by HCl to pH ~4. Large amount solid appeared, filtered, washed with water, dried gave 1b (11.9 g) as yellow solid.

Step 1B

To a solution of 1b (2.3 g, 7.5 mmol) in EtOAc (120 ml) at 60° C. was added dropwise a solution of 1c (2.3 g, 11.4 mmol) in EtOAc (32 ml). The mixture was refluxed for 4 h. After cooled to room temperature, the solvents were removed. The residue was purified by silica gel chromatography to afford light yellow oil 1d (1.09 g).

Step 1C

To a solution of 1d (1.09 g) in DCM (200 ml) was added slowly a solution of $Br_2$ (6.15 g) in DCM (7 ml) over 30 min. The mixture was stirred for 30 min, and then quenched with a solution of 10% $Na_2S_2O_3$ and saturated solution of $NaHCO_3$. The two phases were separated; the aqueous phase was extracted with DCM. The combined organic extracts were treated with excess $Boc_2O$, dried over $Na_2SO_4$, filtered and concentrated. The residue was purified by silica gel chromatography to give 1e (0.8 g) and 1d (0.3 g).

Step 1D

A mixture of 1e (0.8 g), 1f (1.2 g), Na₂CO₃ (2 M, 5 ml), and Pd(dppf)Cl₂ (0.3 g) in 1.4-dioxane (50 ml) was stirred in under N₂ at 80° C. for 20 h. After cooled to room temperature, the solvents were removed. The residue was purified by silica gel chromatography to give colorless oil 1g (0.8 g). MS (ESI): m/z=516 [M+H]⁺.

Step 1E

A mixture of 1g (0.8 g) and N₂H₄ (8 ml) in EtOH (80 ml) was refluxed for 28 h. After cooled to room temperature, the solvents were removed. The residue was purified by silica gel chromatography to give colorless oil 1h (0.327 g). MS (ESI): m/z=502 [M+H]⁺.

Step 1F

To a solution of 1 h (0.327 g) in DCM (15 ml) was added TFA (1.5 ml). The mixture was stirred at rt for 30 min and concentrated to give 1i which was used directly in next step.

Step 1G

To a solution of 1i (10.6 mg, 0.026 mmol) in DCM (2 ml) were added Et₃N (0.1 ml), acrylic acid (5 mg, 0.067 mmol) and HBTU (19 mg, 0.05 mmol). The resulting mixture was stirred at room temperature for 0.5 h and purified by reversed phase preparative HPLC to give title compound 1 (3.5 mg) as white solid. MS (ESI): m/z=456 [M+H]⁺.

Examples 2 to 12

(Table 1) were made from 1b and corresponding amines (commercially available) via the similar conditions described in steps 1B-1G of Example 1.

TABLE 1

Compounds of formula:

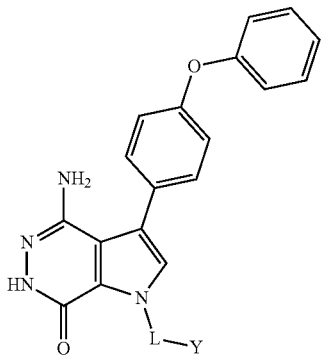

| Example | L-Y | Name | MS(ESI) m/z [M + H]⁺ |
|---|---|---|---|
| 2 | | 4-amino-3-(4-phenoxyphenyl)-1-(1-prop-2-enoyl-3-piperidyl)-6H-pyrazolo[3,4-d]pyridazin-7-one | 456 |
| 3 | | 4-amino-3-(4-phenoxyphenyl)-1-[(3S)-1-prop-2-enoylpyrrolidin-3-yl]-6H-pyrrolo[2,3-d]pyridazin-7-one | 442 |
| 4 | | 4-amino-3-(4-phenoxyphenyl)-1-[(3R)-1-prop-2-enoylpyrrolidin-3-yl]-6H-pyrrolo[2,3-d]pyridazin-7-one | 442 |

TABLE 1-continued

Compounds of formula:

| Example | L-Y | Name | MS(ESI) m/z [M + H]+ |
|---|---|---|---|
| 5 | *azetidine with acryloyl* | 4-amino-3-(4-phenoxyphenyl)-1-(1-prop-2-enoylazetidin-3-yl)-6H-pyrrolo[2,3-d]pyridazin-7-one | 428 |
| 6 | *(2S)-pyrrolidine methyl with acryloyl* | 4-amino-3-(4-phenoxyphenyl)-1-[[(2S)-1-prop-2-enoylpyrrolidin-2-yl]methyl]-6H-pyrrolo[2,3-d]pyridazin-7-one | 456 |
| 7 | *(2R)-pyrrolidine methyl with acryloyl* | 4-amino-3-(4-phenoxyphenyl)-1-[[(2R)-1-prop-2-enoylpyrrolidin-2-yl]methyl]-6H-pyrrolo[2,3-d]pyridazin-7-one | 456 |
| 8 | *3-pyrrolidine methyl with acryloyl* | 4-amino-3-(4-phenoxyphenyl)-1-[(1-prop-2-enoylpyrrolidin-3-yl)methyl]-6H-pyrrolo[2,3-d]pyridazin-7-one | 456 |
| 9 | *4-piperidyl with acryloyl* | 4-amino-3-(4-phenoxyphenyl)-1-(1-prop-2-enoyl-4-piperidyl)-6H-pyrrolo[2,3-d]pyridazin-7-one | 456 |

TABLE 1-continued
Compounds of formula:
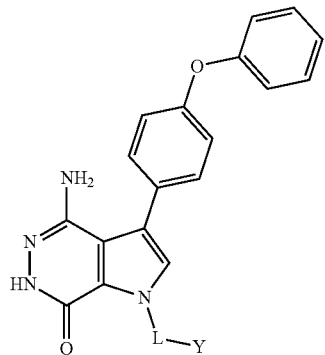
| Example | L-Y | Name | MS(ESI) m/z [M + H]⁺ |
|---|---|---|---|
| 10 | | 4-amino-3-(4-phenoxyphenyl)-1-[(1-prop-2-enoyl-4-piperidyl)methyl]-6H-pyrrolo[2,3-d]pyridazin-7-one | 470 |
| 11 | | N-((1s,4s)-4-(4-amino-7-oxo-3-(4-phenoxyphenyl)-6,7-dihydro-1H-pyrrolo[2,3-d]pyridazin-1-yl)cyclohexyl)acrylamide | 470 |
| 12 | | 4-amino-3-(4-phenoxyphenyl)-1-[(1-prop-2-enoylazetidin-3-yl)methyl]-6H-pyrrolo[2,3-d]pyridazin-7-one | 442 |

Example 13

1-(1-acryloyl-4-fluoropiperidin-3-yl)-4-amino-3-(4-phenoxyphenyl)-1H-pyrrolo[2,3-d]pyridazin-7(6H)-one

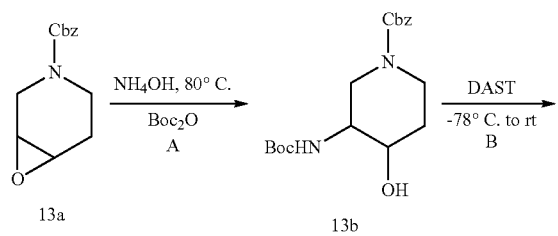

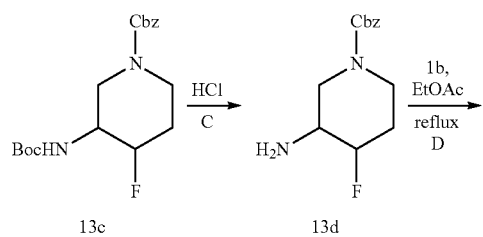

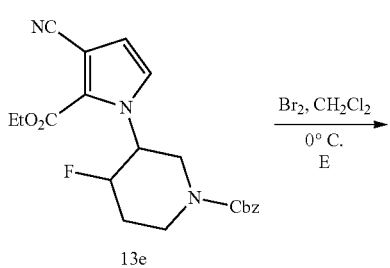

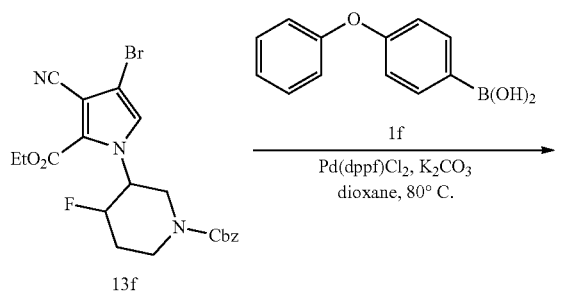

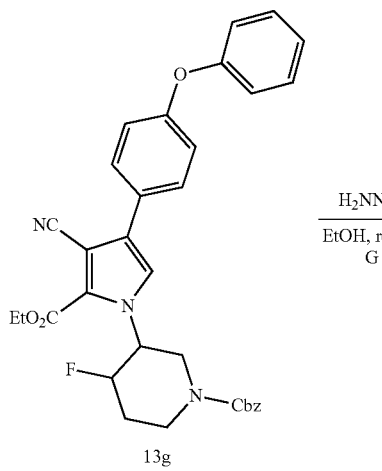

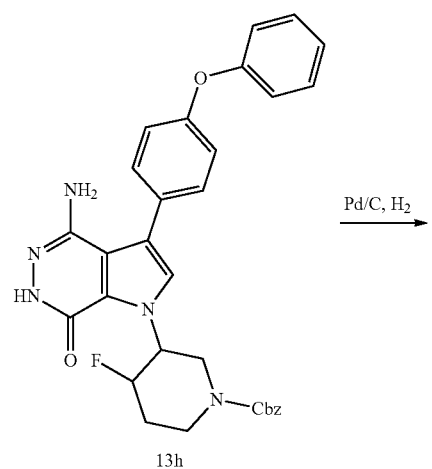

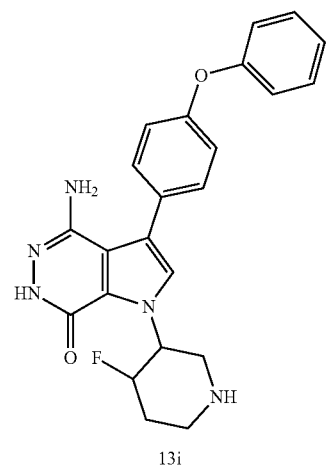

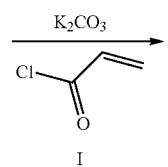

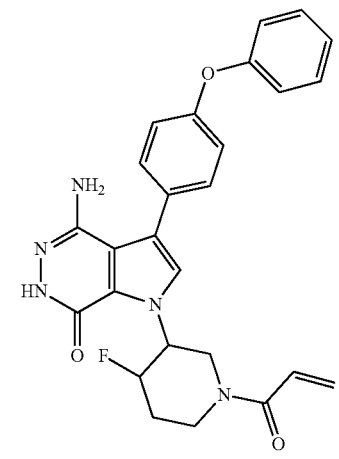

Step 13A

A mixture of 13a (2.2 g) and NH₄OH (14 mL) in EtOH (33 mL) was stirred in seal tube at 80° C. for 18 h. The solvents were removed; the residue was dissolved in THF (30 mL) and EtOH (30 mL) and charged with Boc₂O (2.46 g). The mixture was stirred at room temperature for 20 h. The crude product was purified by silica gel chromatography to give white solid 13b (1.02 g) and undesired region isomer (1.7 g).

Step 13B

DAST (0.28 mL, 2.14 mmol) was added dropwise to a solution of 13b (0.68 g, 1.94 mmol) in DCM (20 mL) at −78° C. The mixture was allowed to warm to room temperature overnight. It was quenched with saturated NaHCO$_3$ solution, extracted with DCM. The organic extracts were dried over Na$_2$SO$_4$, filtered and concentrated. The residue was purified by silica gel chromatography to give colorless oil 13c (0.31 g).

Step 13C

A mixture of 13c (0.31 g) and HCl (4 M in dioxane) was stirred for 2 h. The solvents were removed, the residue was suspended in EtOAc, 2M K$_2$CO$_3$ solution was added to adjust pH over 9. The aqueous layer was extracted with EtOAc three times. The combined organic extracts were dried over Na$_2$SO$_4$, filtered and concentrated to give light yellow oil 13d (0.18 g).

Step 13D

To a solution of 13d (140 mg) in EtOAc (12 ml) at 60° C. was added dropwise a solution of 1b (140 mg) in EtOAc (3 ml). The mixture was refluxed for 18 h. After cooled to room temperature, the solvents were removed. The residue was purified by silica gel chromatography to afford yellow oil 13e (40 mg).

Step 13E

To a solution of 13e (40 mg) and AcOH (40 μl) in DCM (3 ml) at 0° C. was added Br$_2$ (40 mg) slowly. The mixture was allowed to warm to rt and stirred for 5 h, and then quenched with a solution of 10% Na$_2$S$_2$O$_3$ and saturated solution of NaHCO$_3$. The two phases were separated; the aqueous phase was extracted with EtOAc. The combined organic layer was dried over Na$_2$SO$_4$, filtered and concentrated. The residue was purified by silica gel chromatography to give 13f (18 mg).

Step 13F

A mixture of 13f (22 mg), 1f (25 mg), K$_2$CO$_3$ (2 M, 0.1 ml), and Pd(dppf)Cl$_2$ (13 mg) in 1.4-dioxane (1 ml) was stirred in under N$_2$ at 80° C. for 20 h. After cooled to room temperature, the solvents were removed. The residue was purified by silica gel chromatography to give colorless oil 13g (28 mg). MS (ESI): m/z=568 [M+H]$^+$.

Step 13G

A mixture of 13g (28 mg) and N$_2$H$_4$ (0.2 ml) in EtOH (2 ml) was refluxed for two days. After cooled to room temperature, the solvents were removed. The residue was purified by silica gel chromatography to give 13h (15 mg). MS (ESI): m/z=554 [M+H]$^+$.

Step 13H

A mixture of 13h (15 mg) and Pd/C (10 wt %, 9 mg) in MeOH (1 ml) was stirred under H$_2$ balloon for 3 h. The reaction mixture was filtered through a pad of celite, washed with EtOAc/MeOH and concentrated to give white solid 13i (10 mg).

Step 13I

To a mixture of 13i (5.3 mg) and K$_2$CO$_3$ (2M, 30 μl) in THF (0.8 ml) at 0° C. was added a solution of acryloyl chloride (1.4 mg) in THF. The resulting mixture was stirred at 0° C. for 0.5 h and purified by reversed phase preparative HPLC to give title compound 13 (3 mg) as off white solid. MS (ESI): m/z=474 [M+H]$^+$.

Example 14

(R)-1-(1-acryloyl-5,5-difluoropiperidin-3-yl)-4-amino-3-(4-phenoxyphenyl)-1H-pyrrolo[2,3-d]pyridazin-7(6H)-one

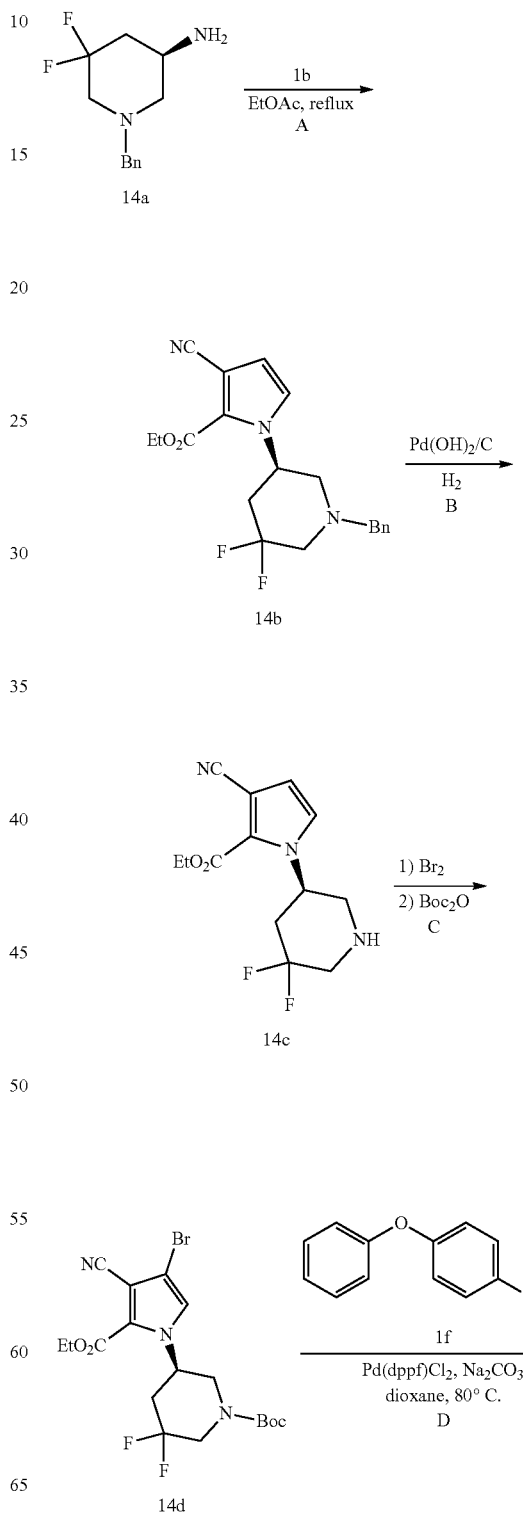

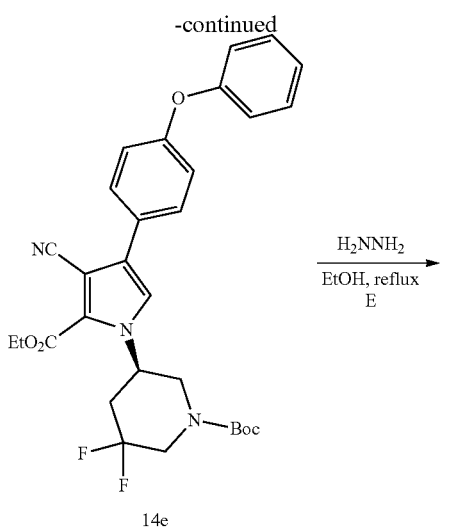

14e

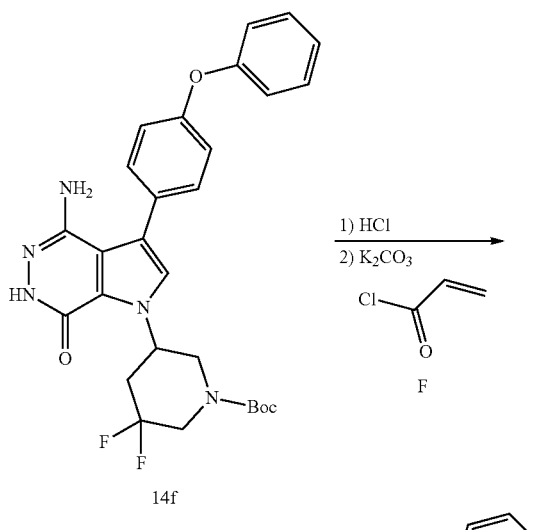

14f

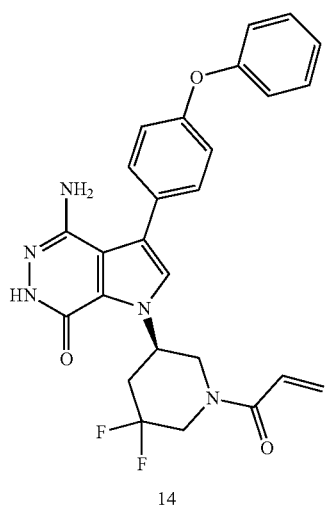

14

Step 14A

To a solution of 1b (271 mg) in EtOAc (12 ml) at 60° C. was added dropwise a solution of 14a (223 mg, the compound was prepared following procedures described in *Organic Letters*, 2011, vol. 13, p. 4442-4445 Anne Cochi et al.) in EtOAc (2 ml). The mixture was refluxed for 18 h. After cooled to room temperature, the solvents were removed. The residue was purified by silica gel chromatography to afford light yellow oil 14b (76 mg).

Step 14B

A mixture of 14b (65 mg) and Pd(OH)$_2$/C (10 wt %, 50 mg) in MeOH/THF (3/1 ml) was stirred under H$_2$ balloon for 20 h. The reaction mixture was filtered through a pad of celite, washed with EtOAc/MeOH and concentrated. The residue was purified by silica gel chromatography to afford white solid 14c (38 mg).

Step 14C

To a solution of 14c (38 mg) in DCM (3 ml) at 0° C. was added Br$_2$ (15 µl) slowly. The mixture was stirred at rt for 18 h. Excess TEA and Boc$_2$O were added. The resulting mixture was stirred at rt for 24 h. Water was added, and the mixture was extracted with EtOAc. The organic extracts were washed with brine, dried over Na$_2$SO$_4$, filtered and concentrated. The residue was purified by silica gel chromatography to give 14d (20 mg).

Step 14D

A mixture of 14d (20 mg), 1f (19 mg), K$_2$CO$_3$ (2M, 0.1 ml), and Pd(dppf)Cl$_2$ (7 mg) in 1.4-dioxane (1.5 ml) was stirred in under N$_2$ at 80° C. for 3 h. After cooled to room temperature, the solvents were removed. The residue was purified by silica gel chromatography to give colorless oil 14e (30 mg). MS (ESI): m/z=552 [M+H]$^+$.

Step 14E

A mixture of 14e (30 mg) and N$_2$H$_4$ (0.25 ml) in EtOH (2.5 ml) was refluxed for 20 h. After cooled to room temperature, the solvents were removed. The residue was purified by silica gel chromatography to give white solid 14f (15 mg). MS (ESI): m/z=538 [M+H]$^+$.

Step 14F

A mixture of 14f (15 mg) and HCl solution (1 ml, 4M in dioxane) was stirred at rt for 2 h and concentrated to give 14g (22 mg) which was used directly in next step without further purification. To a mixture of 14g (13 mg) and K$_2$CO$_3$ (2 M, 40 µl) in THF (1 ml) at 0° C. was added a solution of acryloyl chloride (4 mg) in THF. The resulting mixture was stirred at 0° C. for 20 min and purified by reversed phase preparative HPLC to give title compound 14 (3.3 mg) as white solid. MS (ESI): m/z=492 [M+H]$^+$.

Intermediate 1 tert-butyl (3-aminobicyclo[3.2.1]octan-8-yl)carbamate

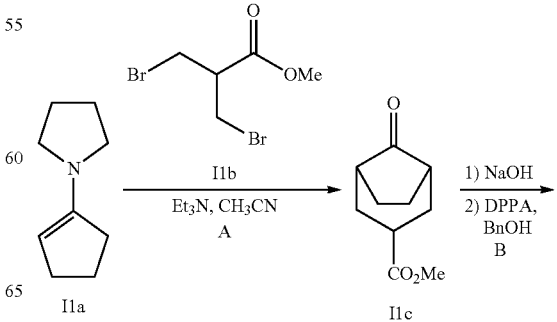

-continued

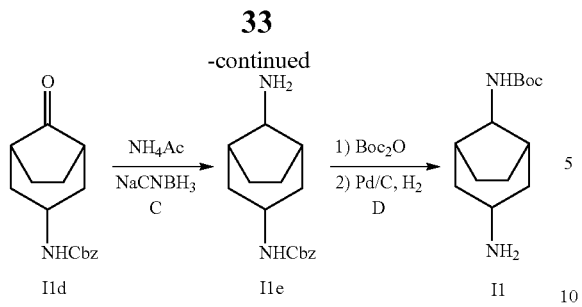

Step I1A

Methyl 3-bromo-2-(bromomethyl)propanoate I1b (2.61 g) was added dropwise to a solution of 1-(cyclopent-1-en-1-yl)pyrrolidine I1a (1.44 g), Et₃N (1.46 ml) in CH₃CN (10 ml). The mixture was refluxed for 20 h. A solution of 5% AcOH in water (1 ml) was added. The mixture was refluxed for 1.5 h. After cooled to room temperature, EtOAc (15 ml) was added. The suspension was filtered. The resulting filtrate was treated with water, extracted with EtOAc. The combined organic extracts were washed with brine, dried over Na₂SO₄, filtered and concentrated. The residue was purified by silica gel chromatography to afford I1c (1.0 g).

Step I1B

A mixture of I1c (1.0 g), 2M NaOH (10 ml) and MeOH (5 ml) was stirred at room temperature for 1.5 h. The mixture was acidified and extracted with EtOAc. The combined organic layers were washed with brine, dried over Na₂SO₄, filtered and concentrated. The resulting oil was dissolved in toluene (14 ml) followed by adding DPPA (1.7 g) and Et₃N (0.84 ml). The mixture was stirred at room temperature for 1.5 h and heated to 110° C. for 2 h. After addition of BnOH (5.7 ml), the mixture was stirred at 110° C. for 2 days. The mixture was diluted with EtOAc and washed with brine, dried over Na₂SO₄, filtered and concentrated. The residue was purified by silica gel chromatography to afford I1d (3.0 g).

Step I1C

To a solution of I1d (0.5 g), NH₄OAc (0.7 g) in CH₃OH (5 ml) was added NaCNBH₃ (0.23 g). The mixture was stirred at rt for 2 h. It was quenched with saturated NaHCO₃ solution, extracted with DCM. The organic extracts were dried over Na₂SO₄, filtered and concentrated. The residue was purified by silica gel chromatography to give I1e (45 mg).

Step I1D

A mixture of I1e (0.24 g) and Boc₂O (1.2 g) in DCM (10 ml) was stirred at rt for 20 h. After evaporation of solvents under reduced pressure, the residue was purified by silica gel chromatography to give 0.14 g colorless oil. The oil was dissolved in MeOH (15 ml) and charged with Pd/C. The mixture was stirred under H₂ balloon for 20 h, filter through a pad of celite and concentrated to give I1 (66 mg). MS (ESI): m/z=241 [M+H]⁺.

Example 15

N-(3-(4-amino-7-oxo-3-(4-phenoxyphenyl)-6,7-dihydro-1H-pyrrolo[2,3-d]pyridazin-1-yl)bicyclo[3.2.1]octan-8-yl)acrylamide

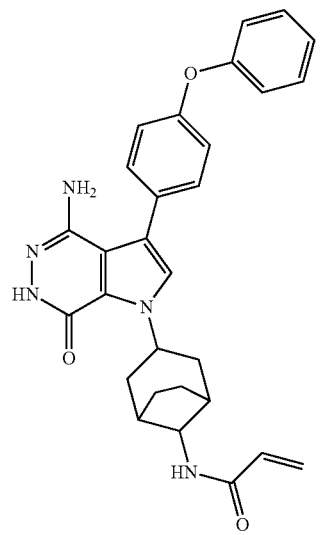

Title compound 15 (light yellow solid, 4.8 mg) was made from 1b and I1 via the similar conditions described in steps 1B-1G of Example 1. MS (ESI): m/z=496 [M+H]⁺.

Example 16

4-amino-1-[(3R)-1-[(E)-4-[isopropyl(methyl)amino]but-2-enoyl]-3-piperidyl]-3-(4-phenoxyphenyl)-6H-pyrrolo[2,3-d]pyridazin-7-one

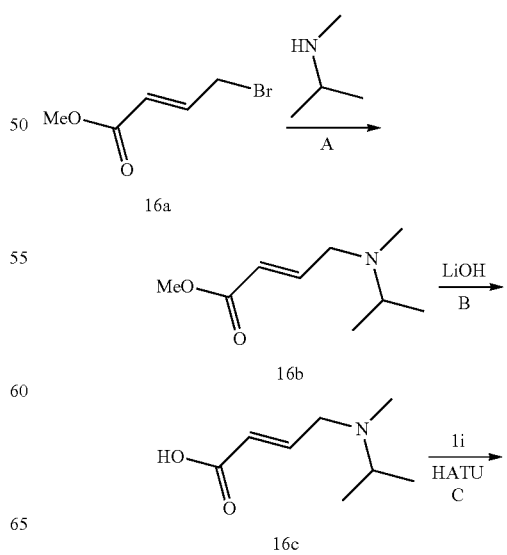

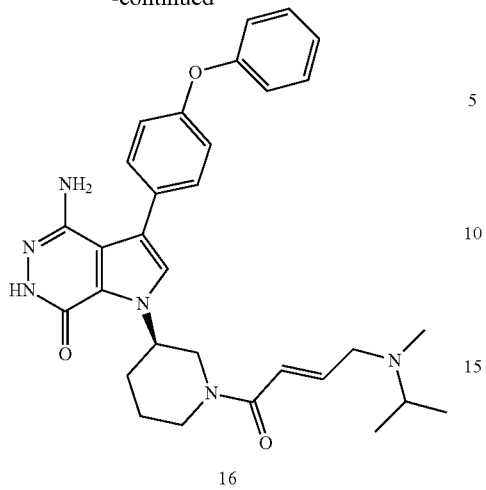

16

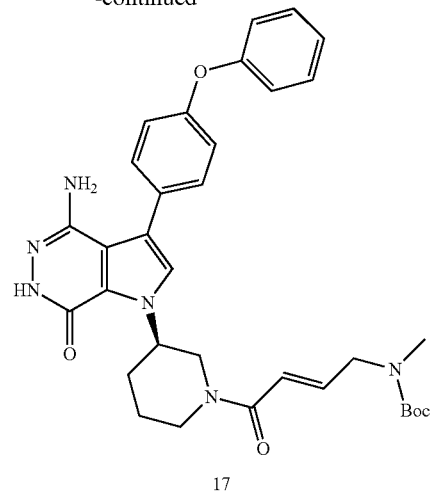

17

Step 16A

A mixture of 16a (225 mg) and N-methylpropan-2-amine (190 mg) in THF (3 ml) was stirred at rt for two days. Saturated NaCl solution was added, the mixture was extracted with EtOAc twice. The organic extracts were washed with brine, dried over $Na_2SO_4$, filtered, and concentrated to give 16b (200 mg).

Step 16B

To a solution of 16b (195 mg) in THF (5 ml) was added LiOH (1M solution, 2.5 ml). The mixture was stirred at rt for 2 h. 2M HCl solution was added to pH <5, concentrated to give 16c (500 mg).

Step 16C

To a solution of 1i (11 mg) in DMF (1 ml) was added DIEA (0.05 ml), acid 16c (15 mg) and HATU (20 mg). The resulting mixture was stirred at room temperature for 1.5 h. The solvents were removed, and the residue was purified by reversed phase preparative HPLC to give title compound 16 (4 mg). MS (ESI): m/z=541 [M+H]$^+$.

Step 17A

To a mixture of 16a (0.43 g) in THF at −60° C. was added dropwise a solution of 2M methylamine in THF (3 ml). The mixture was stirred at −60° C. for 2 h and concentrated. The residue was purified by silica gel chromatography to give 17a (0.146 g).

Step 17B

To a solution of 17a (145 mg) in THF (5 ml) was added NaOH (2 M solution, 2 ml) and MeOH (0.5 ml). The mixture was stirred at rt for 35 min. 1M HCl solution was added to pH <5, concentrated. The crude product was dissolved in DCM/MeOH and treated with Boc$_2$O (0.5 g). The mixture was stirred at rt for 2 h and concentrated. The residue was purified by silica gel chromatography to give 17b (0.11 g).

Step 17C

To a solution of 1i (10 mg) in DCM (2 ml) were added Et$_3$N (0.1 ml), acid 17b (7 mg) and HBTU (18 mg). The resulting mixture was stirred at room temperature for 0.5 h and purified by silica gel chromatography to give title compound 17 (10 mg) as off white solid. MS (ESI): m/z=599 [M+H]$^+$.

Example 17 tert-butyl N-RE)-4-[(3R)-3-[4-amino-7-oxo-3-(4-phenoxyphenyl)-6H-pyrrolo[2,3-d]pyridazin-1-yl]-1-piperidyl]-4-oxo-but-2-enyl]-N-methyl-carbamate Example 18

4-amino-1-[(3R)-1-[(E)-4-(methylamino)but-2-enoyl]-3-piperidyl]-3-(4-phenoxyphenyl)-6H-pyrrolo[2,3-d]pyridazin-7-one

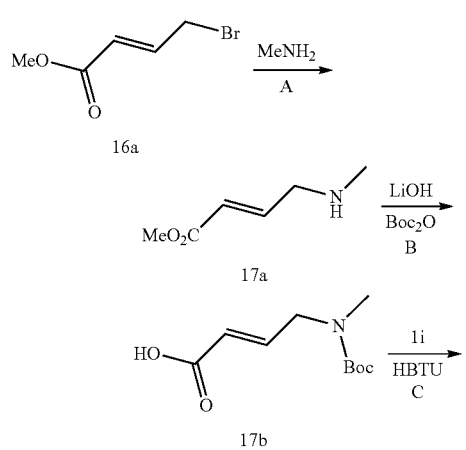

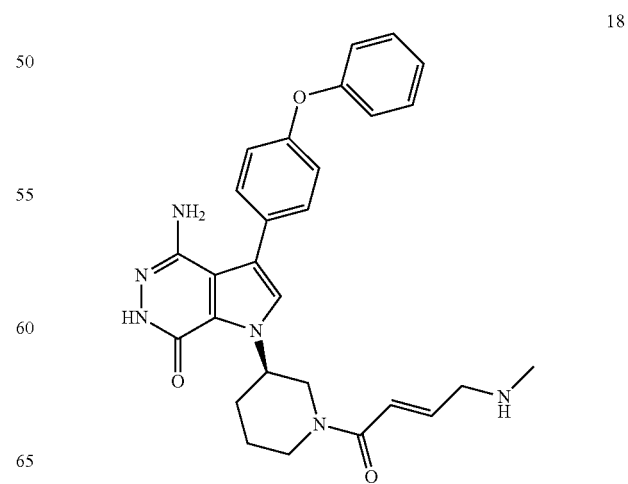

18

To a solution of compound 17 (6 mg) in DCM (1.6 ml) was added TFA (0.2 ml). The mixture was stirred at rt for 30 min and concentrated. The residue was purified by reversed phase preparative HPLC to give title compound 18 (2.4 mg) as white solid. MS (ESI): m/z=499 [M+H]$^+$.

Example 19

4-amino-3-(4-phenoxyphenyl)-1-(1-propionylpiperidin-3-yl)-1H-pyrrolo[2,3-d]pyridazin-7(6H)-one

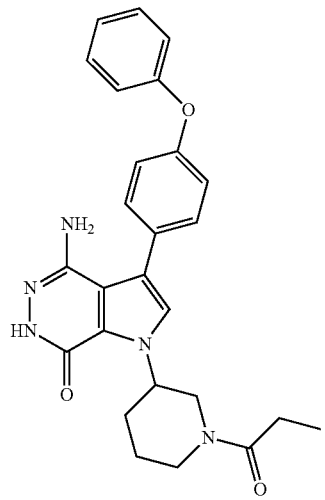

A mixture of compound 2 (5 mg) and Pd/C (10 wt %, 5 mg) in MeOH (5 ml) was stirred under H$_2$ balloon for 3 h. The reaction mixture was filtered through a pad of celite, washed with EtOAc/MeOH and concentrated to give title compound 19 (2.7 mg) as white solid. MS (ESI): m/z=458 [M+H]$^+$.

Example 20

(R)-3-(4-amino-7-oxo-3-(4-phenoxyphenyl)-6,7-dihydro-1H-pyrrolo[2,3-d]pyridazin-1-yl)piperidine-1-carbonitrile

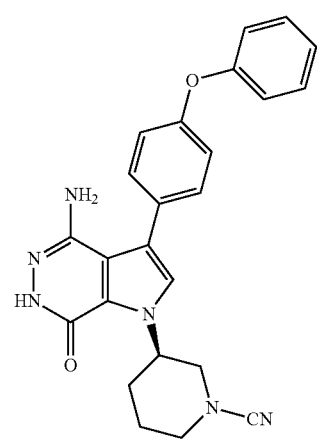

To a mixture of 1i (3.5 mg) and K$_2$CO$_3$ (2M, 15 μl) in acetone (3 ml) was added BrCN (1 mg). The mixture was stirred at rt for 2 h and concentrated. The residue was purified by reversed phase preparative HPLC to give title compound 20 (1.6 mg) as white solid. MS (ESI): m/z=427 [M+H]$^+$.

Example 21

4-amino-1-(1-(but-2-ynoyl)piperidin-3-yl)-3-(4-phenoxyphenyl)-1H-pyrrolo[2,3-d]pyridazin-7(6H)-one

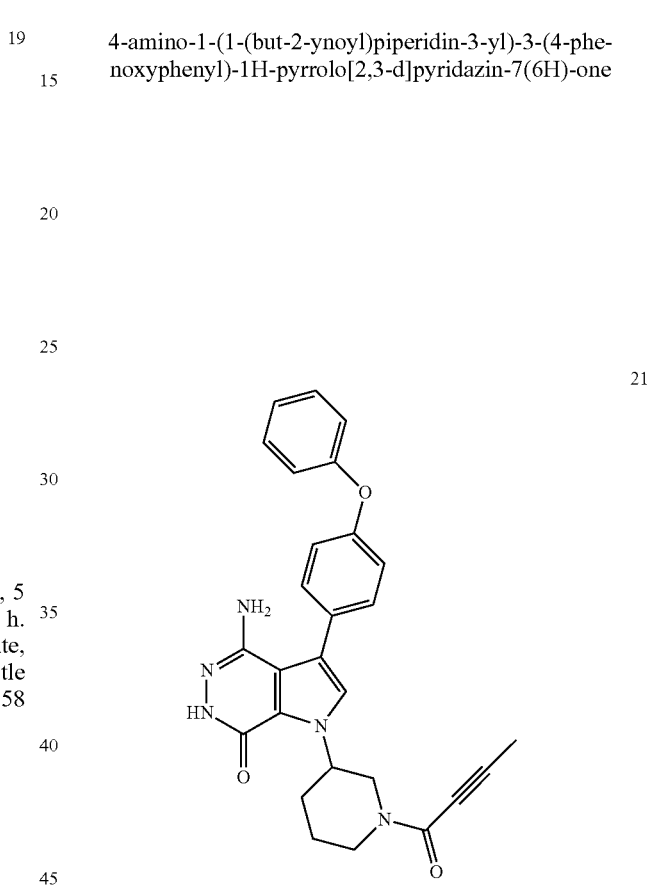

The title compound was made from racemic 1i and but-2-ynoic acid via the similar conditions described in step 1G of Example 1. MS (ESI): m/z=468 [M+H]$^+$.

Examples 22 to 37

(Table 2) were made from 1 i and corresponding acids (commercially available or easily prepared) via the similar conditions described in Examples 16, 17, 18.

TABLE 2

Compounds of formula:

| Example | Z | Name | MS(ESI) m/z [M + H] |
|---|---|---|---|
| 22 | (chloroacetyl group: -C(O)CH₂Cl) | 4-amino-1-[(3R)-1-(2-chloroacetyl)-3-piperidyl]-3-(4-phenoxyphenyl)-6H-pyrrolo[2,3-d]pyridazin-7-one | 478 |
| 23 | (cyclopropanecarbonyl) | 4-amino-1-[(3R)-1-(cyclopropanecarbonyl)-3-piperidyl]-3-(4-phenoxyphenyl)-6H-pyrrolo[2,3-d]pyridazin-7-one | 470 |
| 24 | (cyanoacetyl: -C(O)CH₂CN) | 3-[(3R)-3-[4-amino-7-oxo-3-(4-phenoxyphenyl)-6H-pyrrolo[2,3-d]pyridazin-1-yl]-1-piperidyl]-3-oxo-propanenitrile | 469 |
| 25 | (crotonyl: -C(O)CH=CHCH₃) | 4-amino-1-[(3R)-1-[(E)-but-2-enoyl]-3-piperidyl]-3-(4-phenoxyphenyl)-6H-pyrrolo[2,3-d]pyridazin-7-one | 470 |
| 26 | (-C(O)CH=CHCH₂N(CH₃)₂) | 4-amino-1-[(3R)-1-[(E)-4-(dimethylamino)but-2-enoyl]-3-piperidyl]-3-(4-phenoxyphenyl)-6H-pyrrolo[2,3-d]pyridazin-7-one | 513 |
| 27 | (-C(O)CH=CHCH₂N(Et)₂) | 4-amino-1-[(3R)-1-[(E)-4-(diethylamino)but-2-enoyl]-3-piperidyl]-3-(4-phenoxyphenyl)-6H-pyrrolo[2,3-d]pyridazin-7-one | 541 |
| 28 | (-C(O)CH=CHCH₂NH-cyclopropyl) | 4-amino-1-[(3R)-1-[(E)-4-(cyclopropylamino)but-2-enoyl]-3-piperidyl]-3-(4-phenoxyphenyl)-6H-pyrrolo[2,3-d]pyridazin-7-one | 525 |

TABLE 2-continued

Compounds of formula:

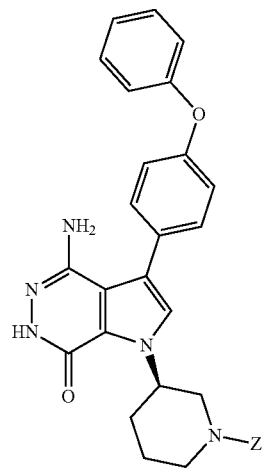

| Example | Z | Name | MS(ESI) m/z [M + H] |
|---|---|---|---|
| 29 | | 4-amino-1-[(3R)-1-[(E)-4-(cyclopropyl(methyl)amino)but-2-enoyl]-3-piperidyl]-3-(4-phenoxyphenyl)-6H-pyrrolo[2,3-d]pyridazin-7-one | 539 |
| 30 | | 4-amino-1-[(3R)-1-[(E)-4-[cyclopropyl(ethyl)amino]but-2-enoyl]-3-piperidyl]-3-(4-phenoxyphenyl)-6H-pyrrolo[2,3-d]pyridazin-7-one | 553 |
| 31 | | 4-amino-1-[(3R)-1-[(E)-4-[cyclobutyl(methyl)amino]but-2-enoyl]-3-piperidyl]-3-(4-phenoxyphenyl)-6H-pyrrolo[2,3-d]pyridazin-7-one | 553 |
| 32 | | 4-amino-1-[(3R)-1-[(E)-4-[cyclohexyl(methyl)amino]but-2-enoyl]-3-piperidyl]-3-(4-phenoxyphenyl)-6H-pyrrolo[2,3-d]pyridazin-7-one | 581 |
| 33 | | 4-amino-1-[(3R)-1-[(E)-4-(azetidin-1-yl)but-2-enoyl]-3-piperidyl]-3-(4-phenoxyphenyl)-6H-pyrrolo[2,3-d]pyridazin-7-one | 525 |

TABLE 2-continued

Compounds of formula:

| Example | Z | Name | MS(ESI) m/z [M + H] |
|---|---|---|---|
| 34 | pyrrolidinyl-butenone | 4-amino-3-(4-phenoxyphenyl)-1-[(3R)-1-[(E)-4-pyrrolidin-1-ylbut-2-enoyl]-3-piperidyl]-6H-pyrrolo[2,3-d]pyridazin-7-one | 539 |
| 35 | morpholinyl-butenone | 4-amino-1-[(3R)-1-[(E)-4-morpholinobut-2-enoyl]-3-piperidyl]-3-(4-phenoxyphenyl)-6H-pyrrolo[2,3-d]pyridazin-7-one | 555 |
| 36 | methylpiperazinyl-butenone | 4-amino-1-[(3R)-1-[(E)-4-(4-methylpiperazin-1-yl)but-2-enoyl]-3-piperidyl]-3-(4-phenoxyphenyl)-6H-pyrrolo[2,3-d]pyridazin-7-one | 568 |
| 37 | methoxy-butenone | 4-amino-1-[(3R)-1-[(E)-4-methoxybut-2-enoyl]-3-piperidyl]-3-(4-phenoxyphenyl)-6H-pyrrolo[2,3-d]pyridazin-7-one | 500 |

Examples 38 to 49

(Table 3) were made from (E)-4-(dimethylamino)but-2-enoic acid and corresponding amines (precursors of previous examples) via the similar conditions described in step 16C of Example 16.

TABLE 3

Compounds of formula:

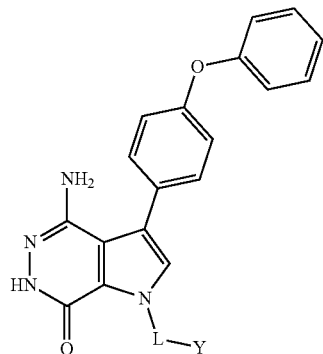

| Example | L-Y | Name | MS(ESI) m/z [M + H]+ |
|---|---|---|---|
| 38 | (3-piperidyl with N-C(O)-CH=CH-CH2-N(CH3)2) | 4-amino-1-[1-[(E)-4-(dimethylamino)but-2-enoyl]-3-piperidyl]-3-(4-phenoxyphenyl)-6H-pyrrolo[2,3-d]pyridazin-7-one | 513 |
| 39 | (3R)-pyrrolidin-3-yl with N-C(O)-CH=CH-CH2-N(CH3)2 | 4-amino-1-[(3R)-1-[(E)-4-(dimethylamino)but-2-enoyl]pyrrolidin-3-yl]-3-(4-phenoxyphenyl)-6H-pyrrolo[2,3-d]pyridazin-7-one | 499 |
| 40 | azetidin-3-yl with N-C(O)-CH=CH-CH2-N(CH3)2 | 4-amino-1-[1-[(E)-4-(dimethylamino)but-2-enoyl]azetidin-3-yl]-3-(4-phenoxyphenyl)-6H-pyrrolo[2,3-d]pyridazin-7-one | 485 |
| 41 | (2S)-pyrrolidin-2-ylmethyl with N-C(O)-CH=CH-CH2-N(CH3)2 | 4-amino-1-[[(2S)-1-[(E)-4-(dimethylamino)but-2-enoyl]pyrrolidin-2-yl]methyl]-3-(4-phenoxyphenyl)-6H-pyrrolo[2,3-d]pyridazin-7-one | 513 |

TABLE 3-continued

Compounds of formula:

| Example | L-Y | Name | MS(ESI) m/z [M + H]+ |
|---|---|---|---|
| 42 | | 4-amino-1-[[(2R)-1-[(E)-4-(dimethylamino)but-2-enoyl]pyrrolidin-2-yl]methyl]-3-(4-phenoxyphenyl)-6H-pyrrolo[2,3-d]pyridazin-7-one | 513 |
| 43 | | 4-amino-1-[[1-[(E)-4-(dimethylamino)but-2-enoyl]pyrrolidin-3-yl]methyl]-3-(4-phenoxyphenyl)-6H-pyrrolo[2,3-d]pyridazin-7-one | 513 |
| 44 | | 4-amino-1-[1-[(E)-4-(dimethylamino)but-2-enoyl]-4-piperidyl]-3-(4-phenoxyphenyl)-6H-pyrrolo[2,3-d]pyridazin-7-one | 513 |
| 45 | | 4-amino-1-[1-[(E)-4-(dimethylamino)but-2-enoyl]-4-fluoro-3-piperidyl]-3-(4-phenoxyphenyl)-6H-pyrrolo[2,3-d]pyridazin-7-one | 531 |

TABLE 3-continued

Compounds of formula:

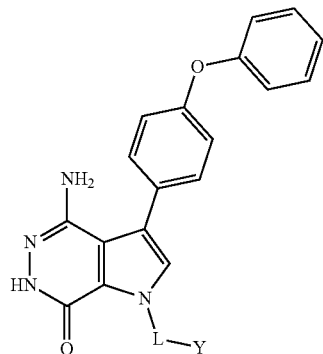

| Example | L-Y | Name | MS(ESI) m/z [M + H]+ |
|---|---|---|---|
| 46 |  | (E)-N-[4-[4-amino-7-oxo-3-(4-phenoxyphenyl)-6H-pyrrolo[2,3 d]pyridazin-1-yl]cyclohexyl]-4-(dimethylamino)but-2-enamide | 527 |
| 47 |  | 4-amino-1-[[1-[(E)-4-(dimethylamino)but-2-enoyl]azetidin-3-yl]methyl]-3-(4-phenoxyphenyl)-6H-pyrrolo[2,3 d]pyridazin-7-one | 499 |
| 48 |  | (E)-N-[3-[4-amino-7-oxo-3-(4-phenoxyphenyl)-6H-pyrrolo[2,3 d]pyridazin-1-yl]-8-bicyclo[3.2.1]octanyl]-4-(dimethylamino)but-2-enamide | 553 |
| 49 |  | 4-amino-1-[(3R)-1-[(E)-4-(dimethylamino)but-2-enoyl]-5,5-difluoro-3-piperidyl]-3-(4-phenoxyphenyl)-6H-pyrrolo[2,3-d]pyridazin-7-one | 549 |

Example 50

(E)-2-[(3R)-3-[4-amino-7-oxo-3-(4-phenoxyphenyl)-6H-pyrrolo[2,3-d]pyridazin-1-yl]piperidine-1-carbonyl]-3-cyclopropyl-prop-2-enenitrile

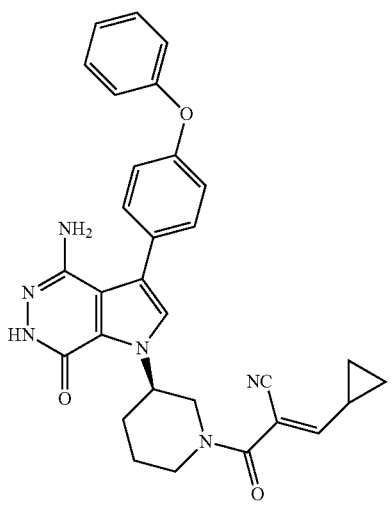

To a mixture of compound 24 (9 mg) and piperidine (2 mg) in MeOH (1 ml) was added cyclopropanecarbaldehyde (2.1 mg). The mixture was stirred at rt for 20 h and concentrated. The residue was purified by reversed phase preparative HPLC to give title compound 50 (2.7 mg) as white solid. MS (ESI): m/z=521 [M+H]$^+$.

Example 51

1-(1-acryloylpiperidin-3-yl)-4-amino-3-(4-methoxyphenyl)-1H-pyrrolo[2,3-d]pyridazin-7(6H)-one

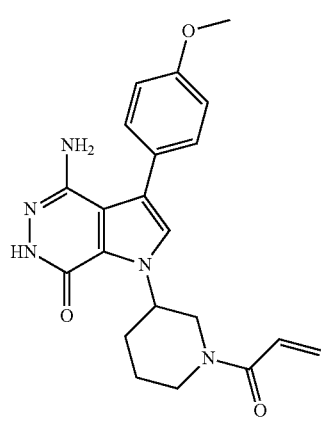

The title compound was made was made from racemic 1e and (4-methoxyphenyl)boronic acid via the similar conditions described in steps 1D-1G of Example 1. MS (ESI): m/z=394 [M+H]$^+$.

Example 52

4-amino-1-[1-[(E)-4-(dimethylamino)but-2-enoyl]-3-piperidyl]-3-(4-methoxyphenyl)-6H-pyrrolo[2,3-d]pyridazin-7-one

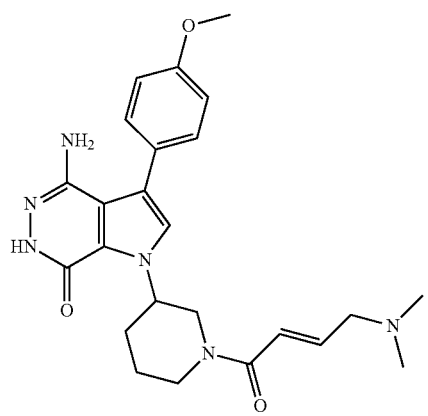

The title compound was made from (E)-4-(dimethylamino)but-2-enoic acid and corresponding amine (precursor of example 51) via the similar conditions described in step 16C of Example 16. MS (ESI): m/z=451 [M+H]$^+$.

Example 53

1-(1-acryloylpiperidin-3-yl)-4-amino-3-(3-chloro-4-methoxyphenyl)-1H-pyrrolo[2,3-d]pyridazin-7(6H)-one

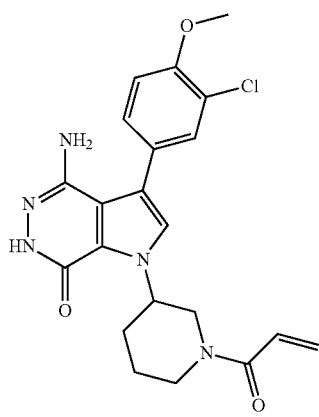

The title compound was made was made from racemic 1e and (3-chloro-4-methoxyphenyl)boronic acid via the similar conditions described in steps 1D-1G of Example 1. MS (ESI): m/z=428 [M+H]$^+$.

Example 54

4-amino-3-(3-chloro-4-methoxy-phenyl)-1-[1-[(E)-4-(dimethylamino)but-2-enoyl]-3-piperidyl]-6H-pyrrolo[2,3-d]pyridazin-7-one

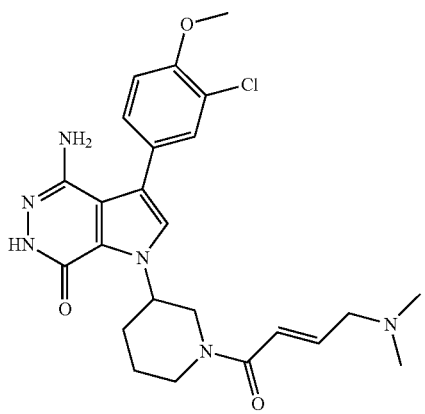

The title compound was made from (E)-4-(dimethylamino)but-2-enoic acid and corresponding amine (precursor of example 53) via the similar conditions described in step 16C of Example 16. MS (ESI): m/z=485 [M+H]$^+$.

Example 55

1-(1-acryloylpiperidin-3-yl)-4-amino-3-(4-(2-fluorophenoxy)phenyl)-1H-pyrrolo[2,3-d]pyridazin-7(6H)-one

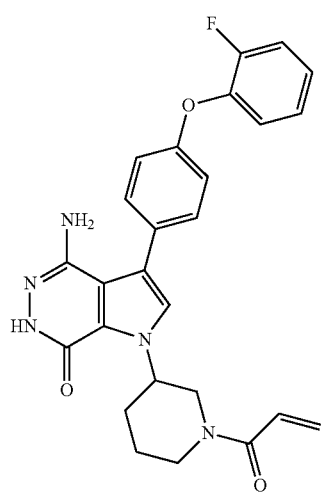

The title compound was made from racemic 1e and ((4-(2-fluorophenoxy)phenyl)boronic acid via the similar conditions described in steps 1D-1G of Example 1. MS (ESI): m/z=474 [M+H]$^+$.

Example 56

(R)-1-(1-acryloylpiperidin-3-yl)-4-amino-3-(4-(2-fluorophenoxy)phenyl)-1H-pyrrolo[2,3-d]pyridazin-7(6H)-one

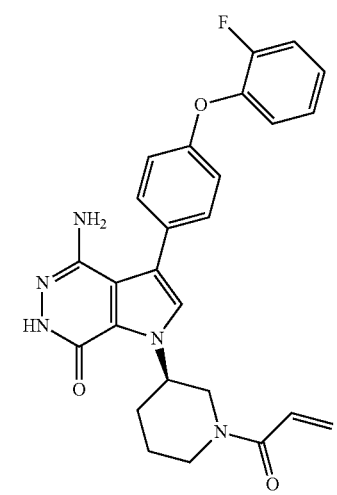

The title compound was made was made from 1e and ((4-(2-fluorophenoxy)phenyl)boronic acid via the similar conditions described in steps 1D-1G of Example 1. MS (ESI): m/z=474 [M+H]$^+$.

Example 57

4-amino-1-[(3R)-1-[(E)-4-(dimethylamino)but-2-enoyl]-3-piperidyl]-3-[4-(2-fluorophenoxy)phenyl]-6H-pyrrolo[2,3-d]pyridazin-7-one

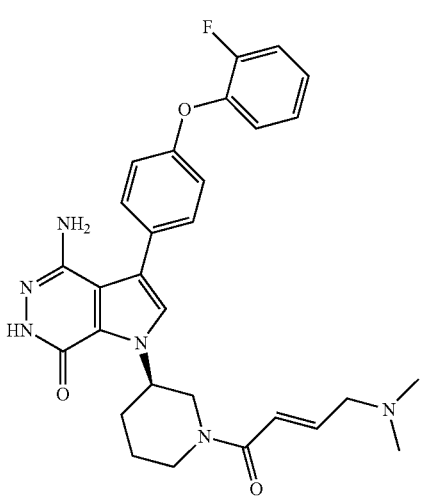

The title compound was made from (E)-4-(dimethylamino)but-2-enoic acid and corresponding amine (precursor of example 56) via the similar conditions described in step 16C of Example 16. MS (ESI): m/z=531 [M+H]$^+$.

Intermediate 2

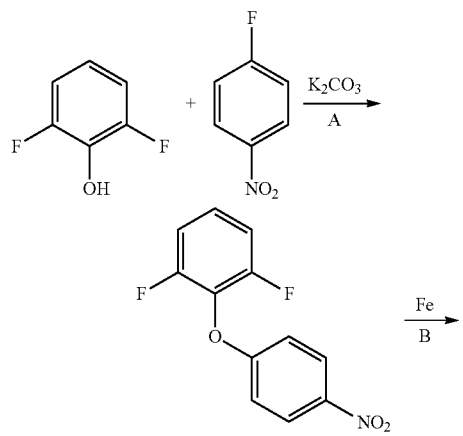

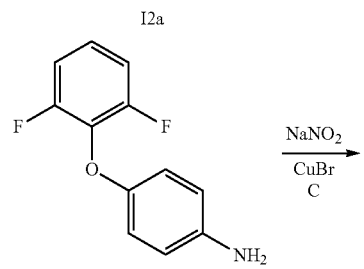

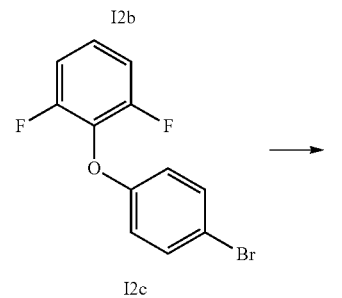

Step I2A

A mixture of 2,6-difluorophenol (3.0 g, 21.3 mmol), 1-fluoro-4-nitrobenzene (3.04 g, 23.4 mmol) and $K_2CO_3$ (4.4 g, 32 mmol) in $CH_3CN$ (50 ml) was refluxed 16 h. After cooled to room temperature, the solvents were removed. Water was added, the mixture was extracted with EtOAc three times. The organic extracts were washed with water, brine, dried over $MgSO_4$, filtered, and concentrated to give oil I2a (4.9 g).

Step I2B

A mixture of 1,3-difluoro-2-(4-nitrophenoxy)benzene I2a (4.9 g, 19.5 mmol), saturated $NH_4Cl$ solution (5 ml) and iron powder (5.5 g, 97.5 mmol) in MeOH (40 mL) was refluxed for 3 h. The mixture was filtered. Water was added to the filtrate, extracted with EtOAc three times. The organic extracts were washed with water, brine, dried over $MgSO_4$, filtered, and concentrated to give light yellow oil I2b (4.1 g). MS (ESI): m/z=222.1 $[M+H]^+$.

Step I2C

To a mixture of 4-(2,6-difluorophenoxy)aniline I2b (4.1 g, 18.5 mmol) in 2M $H_2SO_4$ solution (50 ml) at 0° C. was added a solution of $NaNO_2$ (6.4 g, 92.7 mmol) in water (20 ml). The mixture was stirred at 0° C. for 40 min and charged with CuBr (5.3 g, 37 mmol). The resulting mixture was refluxed for 16 h, cooled to rt, extracted with EtOAc three times. The organic extracts were washed with water, brine, dried over $MgSO_4$, filtered, and concentrated to give colorless oil I2c (1.6 g).

Step I2D

A mixture of 2-(4-bromophenoxy)-1,3-difluorobenzene I2c (1.6 g, 3.6 mmol), bis(pinacolato)-diboron (1.71 g, 6.7 mmol), KOAc (830 mg, 8.4 mmol) and $Pd(PPh_3)_2Cl_2$ (126 mg, 0.18 mmol) in 1,4-dioxane (40 ml) was stirred in under $N_2$ at 80° C. for 16 h. After cooled to room temperature, the solvents were removed. The residue was purified by silica gel chromatography to give colorless oil I2 (1.6 g).

Intermediate 3

2-(4-(4-chlorophenoxy)phenyl)-4,4,5,5-tetramethyl-1,3,2-dioxaborolane

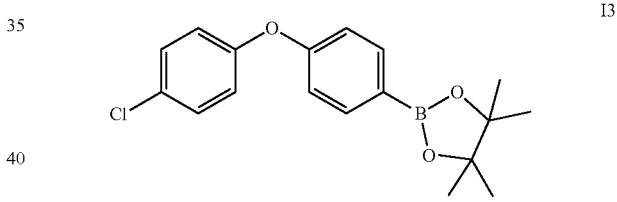

A mixture of 1-chloro-4-(4-iodophenoxy)benzene (330 mg), bis(pinacolato)diboron (508 mg), KOAc (300 mg) and $Pd(PPh_3)_2Cl_2$ (82 mg) in 1,4-dioxane (10 ml) was stirred in seal tube under $N_2$ at 100° C. for 16 h. After cooled to room temperature, filtered off solids, the filtrate was concentrated. The residue was purified by silica gel chromatography to give yellow oil I3 (150 mg).

Intermediate 4

2-(4-(4-fluorophenoxy)phenyl)-4,4,5,5-tetramethyl-1,3,2-dioxaborolane

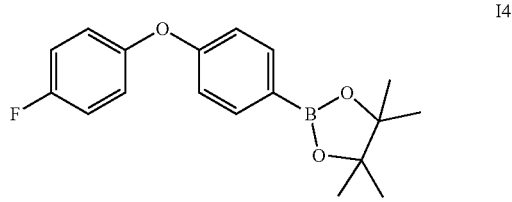 [SMILES: CC1(C)OB(c2ccc(Oc3ccc(F)cc3)cc2)OC1(C)C]

The title compound was made was made from 1-fluoro-4-(4-iodophenoxy)benzene via the similar conditions described in Intermediate 3.

Intermediate 5

2-(4-(3-fluorophenoxy)phenyl)-4,4,5,5-tetramethyl-1,3,2-dioxaborolane

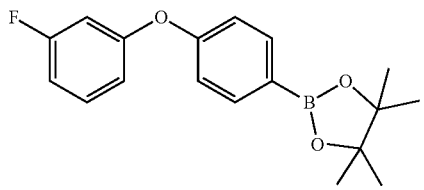

I5

A mixture of (3-fluorophenyl)boronic acid (0.71 g), 4-(4,4,5,5-tetramethyl-1,3,2-dioxaborolan-2-yl)phenol (1.02 g), Cu(OAc)$_2$ (1.0 g), TEA (1.3 ml), and molecular sieve 4A (3 g) in DCM (20 ml) was stirred at rt for 24 h. The reaction mixture was filtered through a pad of celite, washed with DCM and concentrated. The residue was purified by silica gel chromatography to give colorless oil I5 (60 mg).

Intermediate 6

2-(4-(3-chlorophenoxy)phenyl)-4,4,5,5-tetramethyl-1,3,2-dioxaborolane

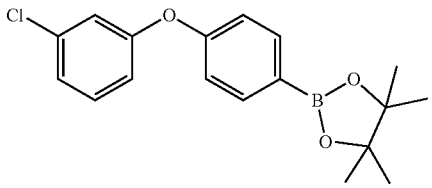

I6

The title compound was made was made from (3-chlorophenyl)boronic acid via the similar conditions described in Intermediate 5.

Intermediate 7

2-(4-(3-chlorophenoxy)-3-methoxyphenyl)-4,4,5,5-tetramethyl-1,3,2-dioxaborolane

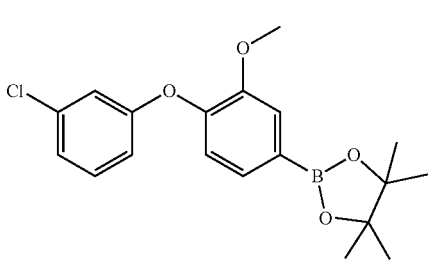

I7

The title compound was made was made from 3-chlorophenol and 1-fluoro-2-methoxy-4-nitrobenzene via the similar conditions described in Intermediate 2.

Intermediate 8

2-(4-(3,4-dichlorophenoxy)-3-methoxyphenyl)-4,4,5,5-tetramethyl-1,3,2-dioxaborolane

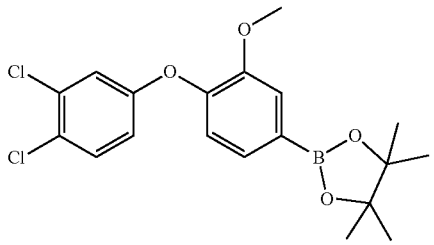

I8

The title compound was made was made from 3,4-dichlorophenol and 1-fluoro-2-methoxy-4-nitrobenzene via the similar conditions described in Intermediate 2.

Intermediate 9

2-(4-(2-chloro-6-fluorophenoxy)phenyl)-4,4,5,5-tetramethyl-1,3,2-dioxaborolane

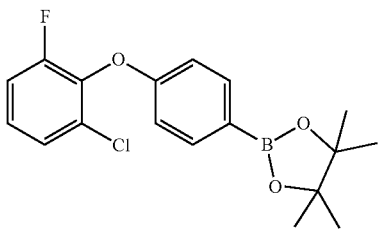

I9

The title compound was made was made from 2-chloro-6-fluorophenol and 1-fluoro-4-nitrobenzene via the similar conditions described in Intermediate 2.

Intermediate 10

2-(4-(2-chlorophenoxy)phenyl)-4,4,5,5-tetramethyl-1,3,2-dioxaborolane

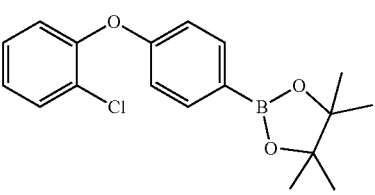

I10

The title compound was made was made from 2-chlorophenol and 1-fluoro-4-nitrobenzene via the similar conditions described in Intermediate 2.

Intermediate 11

2-(2-fluoro-4-phenoxyphenyl)-4,4,5,5-tetramethyl-1,3,2-dioxaborolane

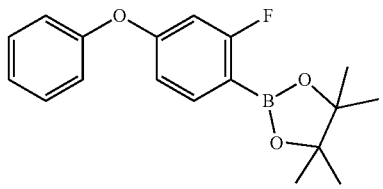

I11

The title compound was made was made from phenol and 2,4-difluoro-1-nitrobenzene via the similar conditions described in Intermediate 2.

Intermediate 12

(3-fluoro-4-phenoxyphenyl)boronic acid

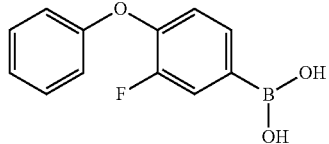

I12

To a solution of 4-bromo-2-fluoro-1-phenoxybenzene (0.5 g, 3.6 mmol) in THF (20 ml) at −78° C. was added dropwise a solution of n-BuLi (2.5 M in hexane, 2.16 ml, 5.4 mmol). After 30 min, triisopropyl borate (1.15 ml, 5.4 mmol) was added dropwise. The mixture was stirred −78° C. for 1 h. The reaction was quenched with water, extracted with EtOAc three times. The combined organic extracts were washed with water, brine, dried over MgSO$_4$, filtered, and concentrated to give light yellow oil I12 (0.18 g).

Example 58

(R)-1-(1-acryloylpiperidin-3-yl)-4-amino-3-(4-(2,6-difluorophenoxy)phenyl)-1H-pyrrolo[2,3-d]pyridazin-7(6H)-one

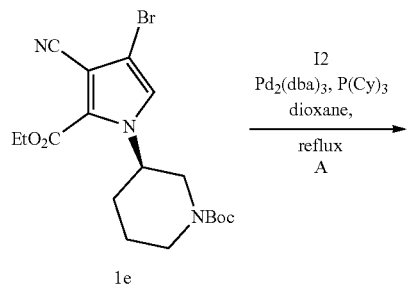

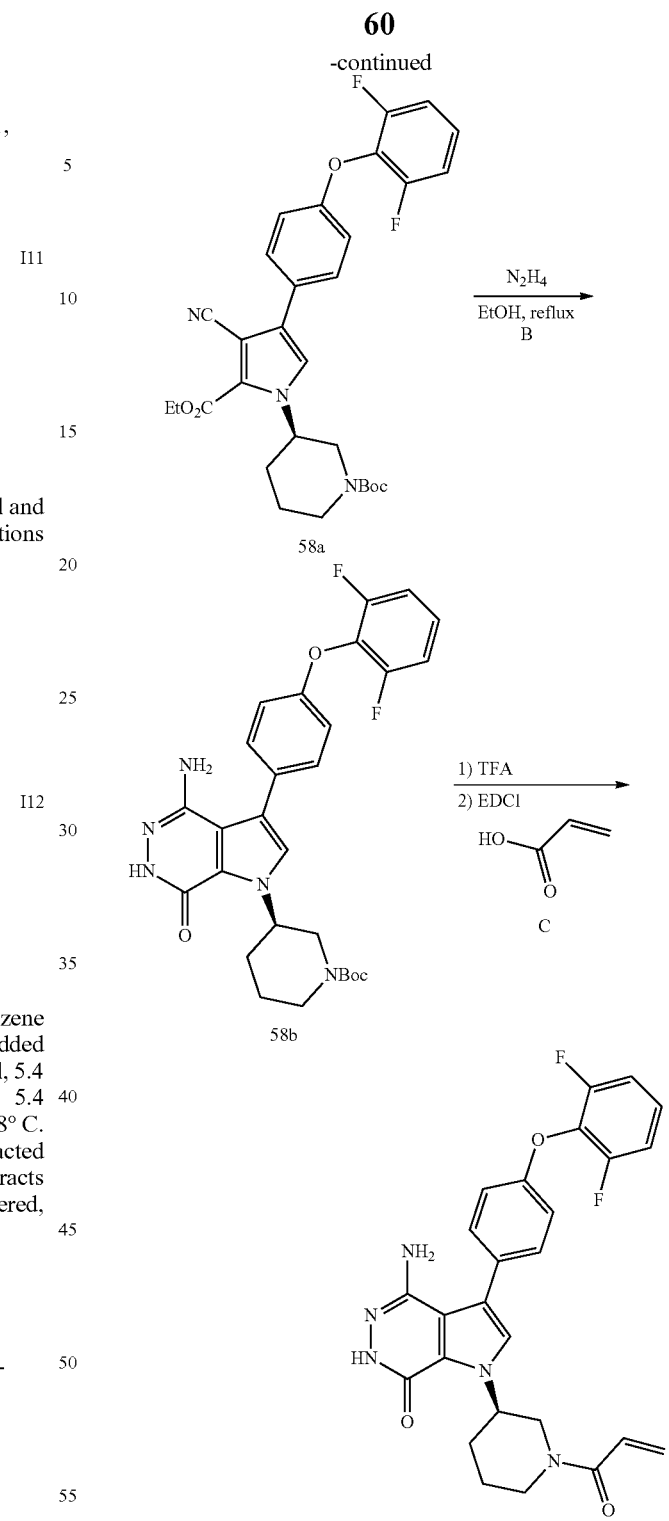

Step 58A

A mixture of 1e (2.8 g, 6.6 mol), 12 (2.2 g, 6.6 mol) and K$_3$PO$_4$·3H$_2$O (2.6 g, 9.9 mol) in 1.4-dioxane/water (10 ml/1 ml) was degassed with N$_2$. Next was added Pd$_2$(dba)$_3$ (300 mg, 0.33 mmol) and P(Cy)$_3$ (185 mg, 0.66 mmol). The resulting mixture was refluxed under N$_2$ for 16 h. After cooled to room temperature, the solid was filtered off, the filtrate was concentrated. The residue was purified by silica gel chromatography to give white solid 58a (1.2 g). MS (ESI): m/z=552 [M+H]⁺.

Step 58B

A mixture of 58a (1.2 g) and $N_2H_4 \cdot H_2O$ (1 mL) in EtOH (5 ml) was refluxed for 16 h. After cooled to room temperature, the solvents were removed. The residue was purified by silica gel chromatography to give white solid 58b (0.66 g). MS (ESI): m/z=538 [M+H]⁺.

Step 58C

To a solution of 58b (880 mg, 1.63 mol) in DCM (5 ml) was added TFA (1 ml). The mixture was stirred at rt for 3 h and concentrated to give oil 58c (940 mg). To a solution of 58c (940 mg) in DCM (5 ml) was added acrylic acid (210 mg, 2.5 mol), EDCI (627 mg, 3.3 mmol) and TEA (340 mg, 3.3 mmol). The resulting mixture was stirred at room temperature for 18 h and concentrated. The residue was purified by silica gel chromatography to give the title compound 58 (450 mg) as white solid. MS (ESI): m/z=492 [M+H]⁺.

Example 59

4-amino-3-[4-(2,6-difluorophenoxy)phenyl]-1-[(3R)-1-[(E)-4-(dimethylamino)but-2-enoyl]-3-piperidyl]-6H-pyrrolo[2,3-d]pyridazin-7-one

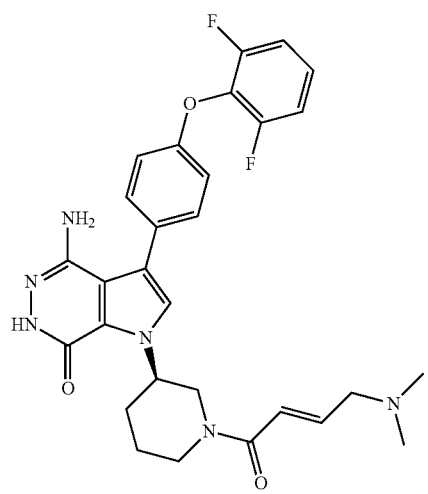

The title compound was made from (E)-4-(dimethylamino)but-2-enoic acid and amine 58c via the similar conditions described in step 16C of Example 16. MS (ESI): m/z=549 [M+H]⁺.

Example 60

1-(1-acryloylpiperidin-3-yl)-4-amino-3-(4-(4-fluorophenoxy)phenyl)-1H-pyrrolo[2,3-d]pyridazin-7(6H)-one

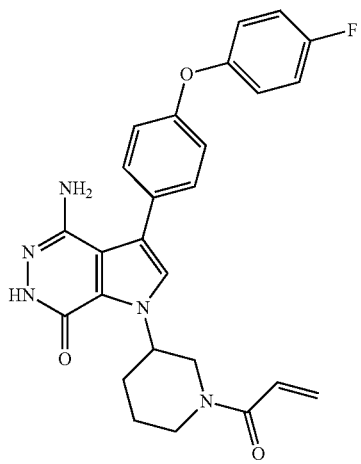

The title compound was made was made from racemic 1e and intermediate 4 via the similar conditions described in steps 1D-1G of Example 1. MS (ESI): m/z=474 [M+H]⁺.

Example 61

4-amino-1-[1-[(E)-4-(dimethylamino)but-2-enoyl]-3-piperidyl]-3-[4-(4-fluorophenoxy)phenyl]-6H-pyrrolo[2,3-d]pyridazin-7-one

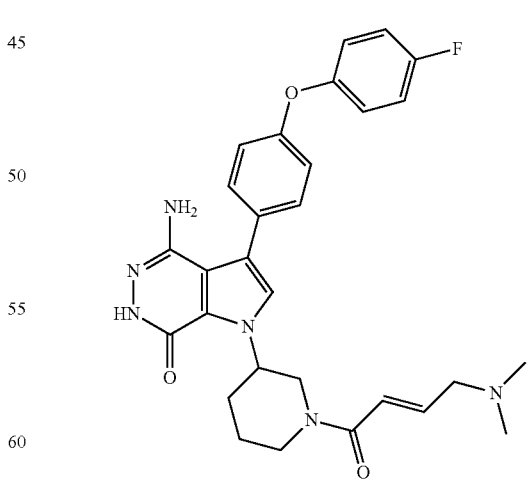

The title compound was made from (E)-4-(dimethylamino)but-2-enoic acid and corresponding amine (precursor of example 60) via the similar conditions described in step 16C of Example 16. MS (ESI): m/z=531 [M+H]⁺.

Example 62

1-(1-acryloylpiperidin-3-yl)-4-amino-3-(4-(3-fluorophenoxy)phenyl)-1H-pyrrolo[2,3-d]pyridazin-7(6H)-one

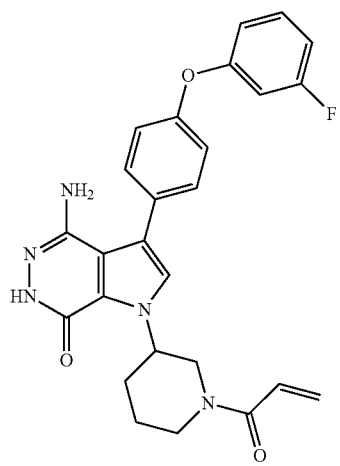

The title compound was made was made from racemic 1e and intermediate 5 via the similar conditions described in steps 1D-1G of Example 1. MS (ESI): m/z=474 [M+H]$^+$.

Example 63

4-amino-1-[1-[(E)-4-(dimethylamino)but-2-enoyl]-3-piperidyl]-3-[4-(3-fluorophenoxy)phenyl]-6H-pyrrolo[2,3-d]pyridazin-7-one

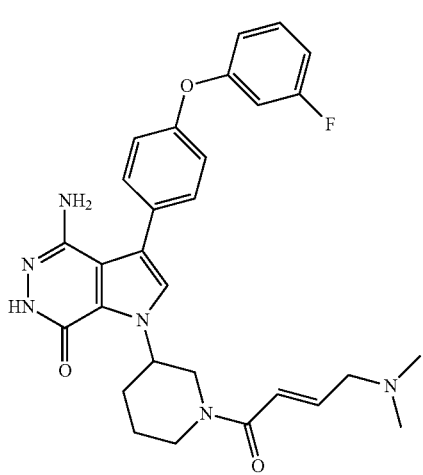

The title compound was made from (E)-4-(dimethylamino)but-2-enoic acid and corresponding amine (precursor of example 62) via the similar conditions described in step 16C of Example 16. MS (ESI): m/z=531 [M+H]$^+$.

Example 64

1-(1-acryloylpiperidin-3-yl)-4-amino-3-(4-(4-chlorophenoxy)phenyl)-1H-pyrrolo[2,3-d]pyridazin-7(6H)-one

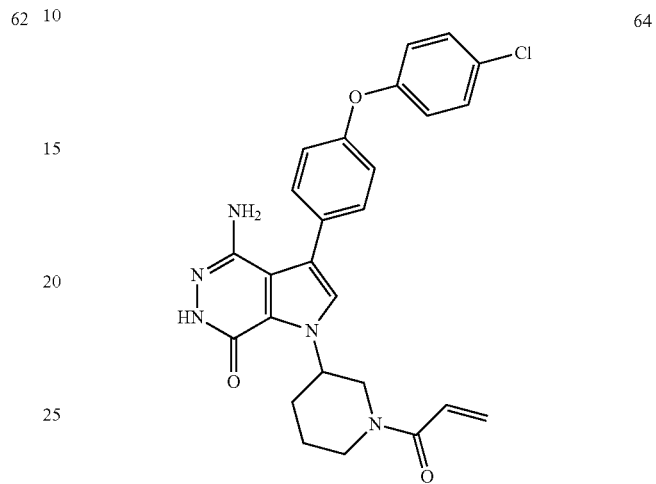

The title compound was made was made from racemic 1e and intermediate 3 via the similar conditions described in steps 1D-1G of Example 1. MS (ESI): m/z=490 [M+H]$^+$.

Example 65

4-amino-3-[4-(4-chlorophenoxy)phenyl]-1-[1-[(E)-4-(dimethylamino)but-2-enoyl]-3-piperidyl]-6H-pyrrolo[2,3-d]pyridazin-7-one

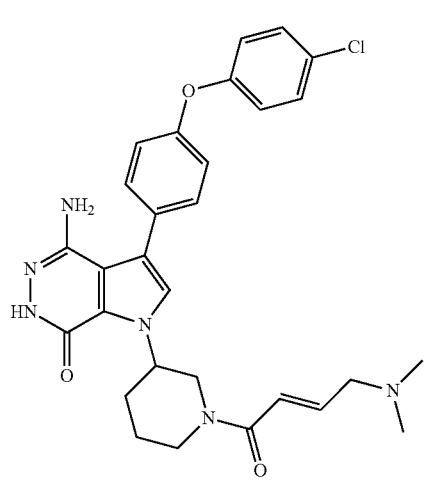

The title compound was made from (E)-4-(dimethylamino)but-2-enoic acid and corresponding amine (precursor of example 64) via the similar conditions described in step 16C of Example 16. MS (ESI): m/z=547 [M+H]$^+$.

Example 66

1-(1-acryloylpiperidin-3-yl)-4-amino-3-(4-(3-chlorophenoxy)phenyl)-1H-pyrrolo[2,3-d]pyridazin-7(6H)-one

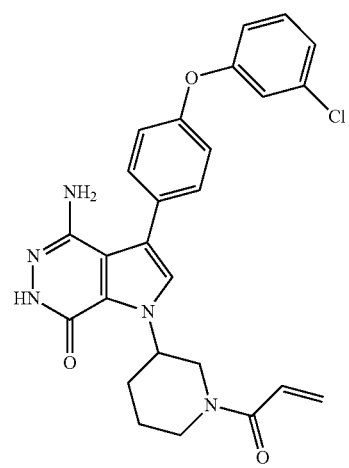

The title compound was made was made from racemic 1e and intermediate 6 via the similar conditions described in steps 1D-1G of Example 1. MS (ESI): m/z=490 [M+H]$^+$.

Example 67

4-amino-3-[4-(3-chlorophenoxy)phenyl]-1-[1-[(E)-4-(dimethylamino)but-2-enoyl]-3-piperidyl]-6H-pyrrolo[2,3-d]pyridazin-7-one

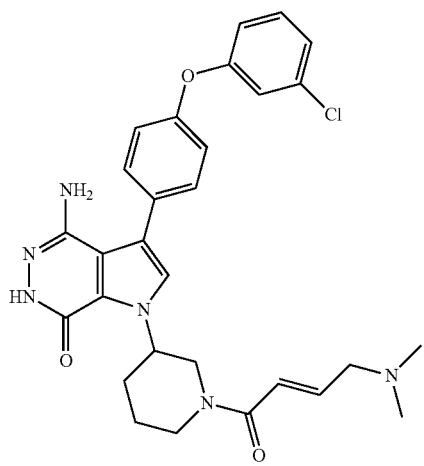

The title compound was made from (E)-4-(dimethylamino)but-2-enoic acid and corresponding amine (precursor of example 66) via the similar conditions described in step 16C of Example 16. MS (ESI): m/z=547 [M+H]$^+$.

Example 68

1-(1-acryloylpiperidin-3-yl)-4-amino-3-(4-(3-chlorophenoxy)-3-methoxyphenyl)-1H-pyrrolo[2,3-d]pyridazin-7(6H)-one

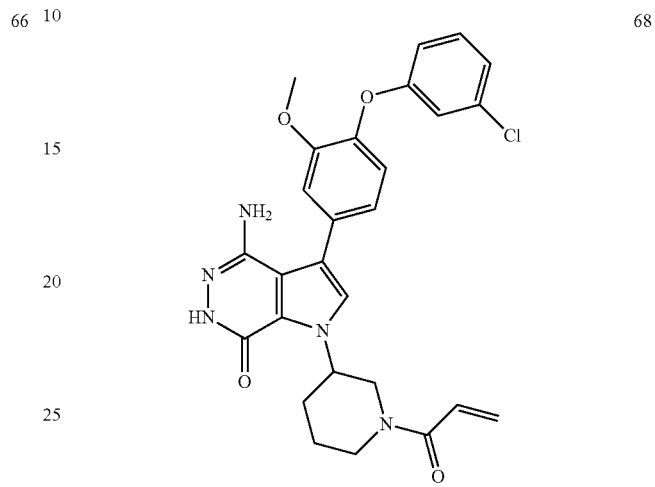

The title compound was made was made from racemic 1e and intermediate 7 via the similar conditions described in steps 1D-1G of Example 1. MS (ESI): m/z=520 [M+H]$^+$.

Example 69

4-amino-3-[4-(3-chlorophenoxy)-3-methoxy-phenyl]-1-[1-[(E)-4-(dimethylamino)but-2-enoyl]-3-piperidyl]-6H-pyrrolo[2,3-d]pyridazin-7-one

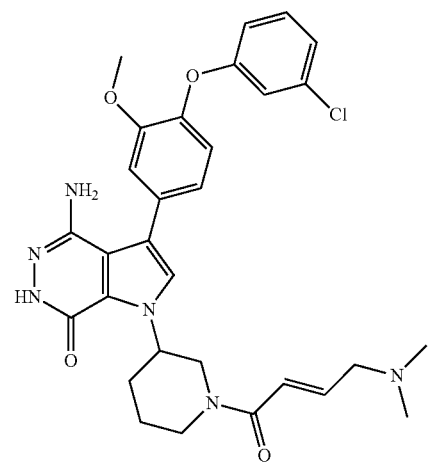

The title compound was made from (E)-4-(dimethylamino)but-2-enoic acid and corresponding amine (precursor of example 68) via the similar conditions described in step 16C of Example 16. MS (ESI): m/z=577 [M+H]$^+$.

Example 70

(R)-1-(1-acryloylpiperidin-3-yl)-4-amino-3-(4-(2-chlorophenoxy)phenyl)-1H-pyrrolo[2,3-d]pyridazin-7(6H)-one

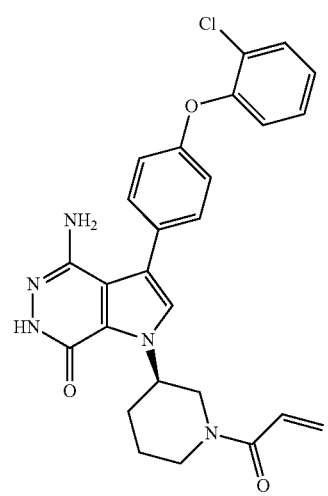

The title compound was made was made from 1e and intermediate 10 via the similar conditions described in Example 58. MS (ESI): m/z=490 [M+H]+.

Example 71

4-amino-3-[4-(2-chlorophenoxy)phenyl]-1-[(3R)-1-[(E)-4-(dimethylamino)but-2-enoyl]-3-piperidyl]-6H-pyrrolo[2,3-d]pyridazin-7-one

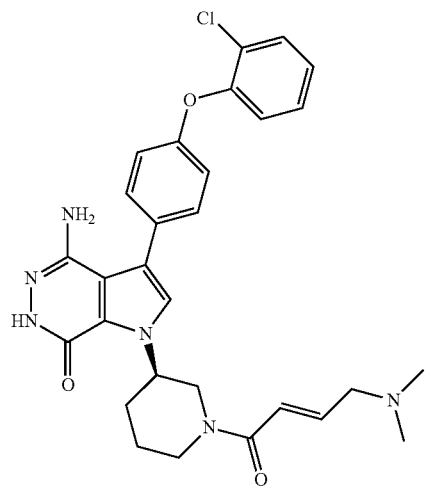

The title compound was made from (E)-4-(dimethylamino)but-2-enoic acid and corresponding amine (precursor of example 70) via the similar conditions described in step 16C of Example 16. MS (ESI): m/z=547 [M+H]+.

Example 72

(R)-1-(1-acryloylpiperidin-3-yl)-4-amino-3-(4-(3,4-dichlorophenoxy)-3-methoxyphenyl)-1H-pyrrolo[2,3-d]pyridazin-7(6H)-one

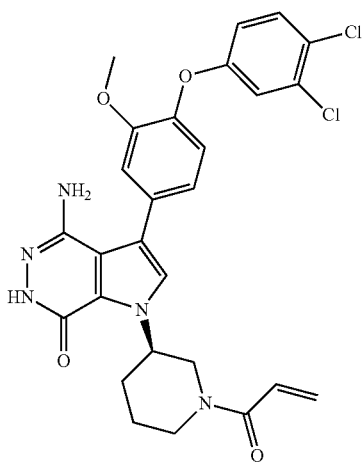

The title compound was made was made from 1e and intermediate 8 via the similar conditions described in Example 58. MS (ESI): m/z=554 [M+H]+.

Example 73

4-amino-3-[4-(3,4-dichlorophenoxy)-3-methoxyphenyl]-1-[(3R)-1-[(E)-4-(dimethylamino)but-2-enoyl]-3-piperidyl]-6H-pyrrolo[2,3-d]pyridazin-7-one

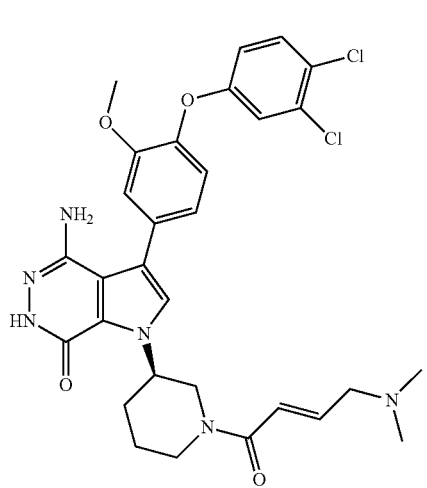

The title compound was made from (E)-4-(dimethylamino)but-2-enoic acid and corresponding amine (precursor of example 72) via the similar conditions described in step 16C of Example 16. MS (ESI): m/z=611 [M+H]+.

Example 74

(R)-1-(1-acryloylpiperidin-3-yl)-4-amino-3-(3-fluoro-4-phenoxyphenyl)-1H-pyrrolo[2,3-d]pyridazin-7(6H)-one

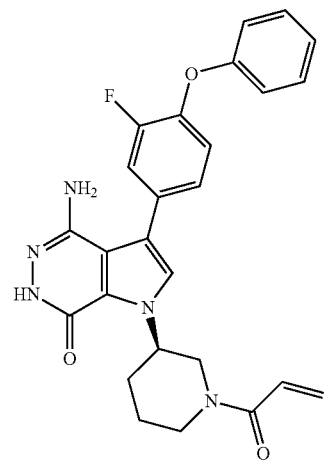

The title compound was made from 1e and intermediate 12 via the similar conditions described in Example 58. MS (ESI): m/z=474 [M+H]+.

Example 75

4-amino-1-[(3R)-1-[(E)-4-(dimethylamino)but-2-enoyl]-3-piperidyl]-3-(3-fluoro-4-phenoxy-phenyl)-6H-pyrrolo[2,3-d]pyridazin-7-one

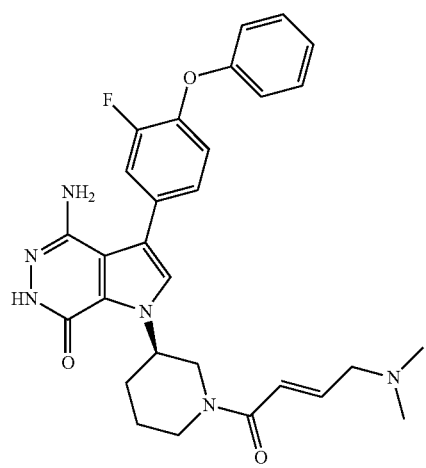

The title compound was made from (E)-4-(dimethylamino) but-2-enoic acid and corresponding amine (precursor of example 74) via the similar conditions described in step 16C of Example 16. MS (ESI): m/z=531 [M+H]+.

Example 76

(R)-1-(1-acryloylpiperidin-3-yl)-4-amino-3-(2-fluoro-4-phenoxyphenyl)-1H-pyrrolo[2,3-d]pyridazin-7(6H)-one

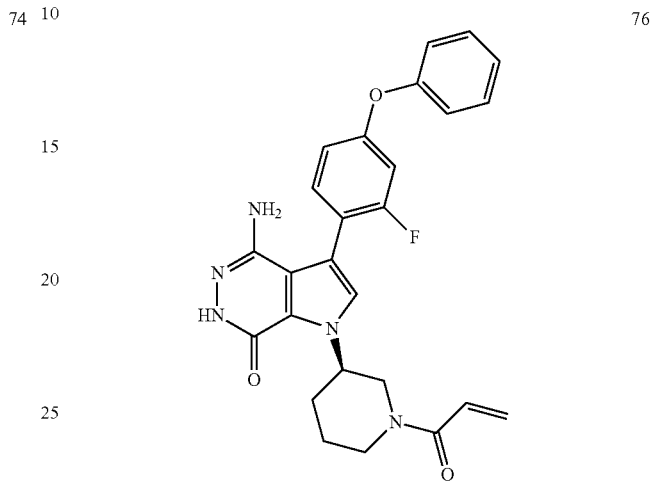

The title compound was made from 1e and intermediate 11 via the similar conditions described in Example 58. MS (ESI): m/z=474 [M+H]+.

Example 77

4-amino-1-[(3R)-1-[(E)-4-(dimethylamino)but-2-enoyl]-3-piperidyl]-3-(2-fluoro-4-phenoxy-phenyl)-6H-pyrrolo[2,3-d]pyridazin-7-one

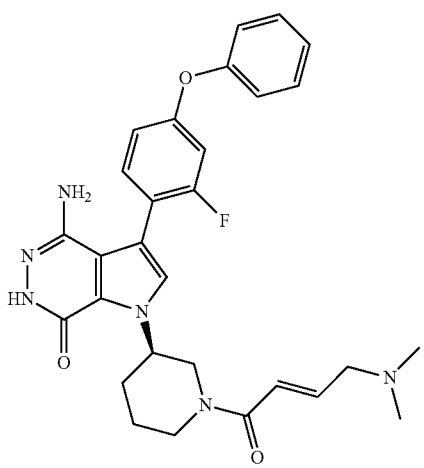

The title compound was made from (E)-4-(dimethylamino)but-2-enoic acid and corresponding amine (precursor of example 76) via the similar conditions described in step 16C of Example 16. MS (ESI): m/z=531 [M+H]+.

Example 78

(R)-1-(1-acryloylpiperidin-3-yl)-4-amino-3-(4-(2-chloro-6-fluorophenoxy)phenyl)-1H-pyrrolo[2,3-d]pyridazin-7(6H)-one

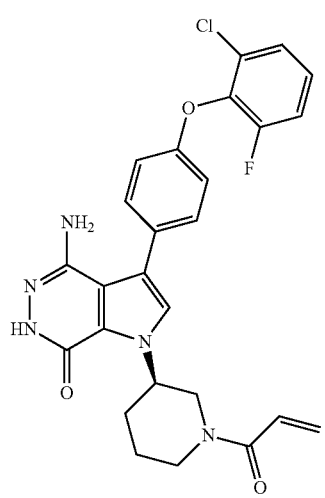

78

The title compound was made from 1e and intermediate 9 via the similar conditions described in Example 58. MS (ESI): m/z=508 [M+H]⁺.

Example 79

4-amino-3-[4-(2-chloro-6-fluoro-phenoxy)phenyl]-1-[(3R)-1-[(E)-4-(dimethylamino)but-2-enoyl]-3-piperidyl]-6H-pyrrolo[2,3-d]pyridazin-7-one

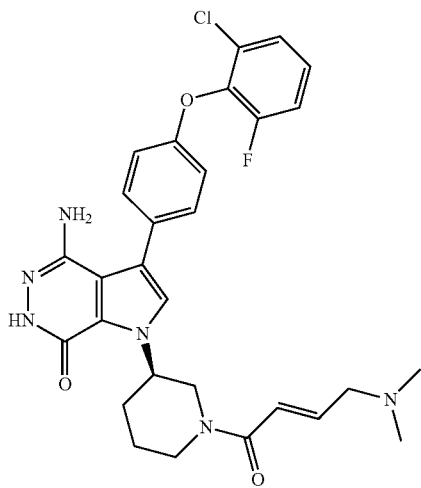

79

The title compound was made from (E)-4-(dimethylamino)but-2-enoic acid and corresponding amine (precursor of example 78) via the similar conditions described in step 16C of Example 16. MS (ESI): m/z=565 [M+H]⁺.

Example 80

(R)-1-(1-acryloylpiperidin-3-yl)-4-amino-2-chloro-3-(4-phenoxyphenyl)-1H-pyrrolo[2,3-d]pyridazin-7(6H)-one

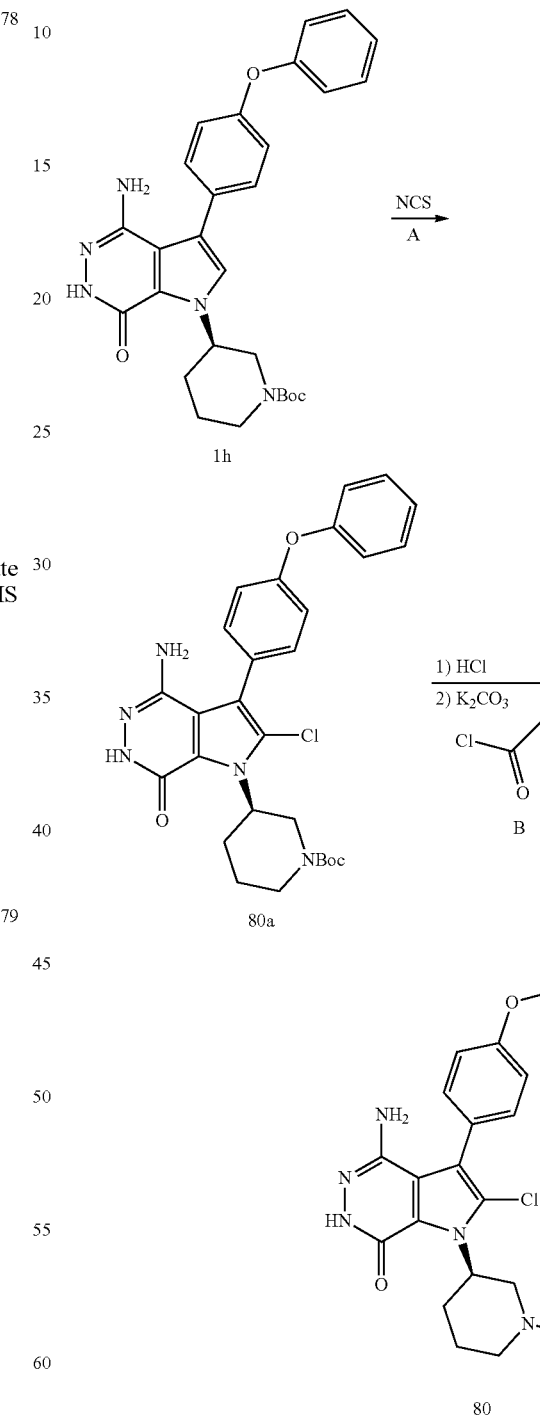

Step 80A

A mixture of 1h (23 mg) and NCS (15 mg) in DCM (1.5 ml) was stirred at rt for 20 h and concentrated. The residue was purified by silica gel chromatography to afford beige solid 80a (13 mg). MS (ESI): m/z=536 [M+H]+.

Step 80B

A mixture of 80a (13 mg) and HCl solution (0.2 ml, 4M in dioxane) in DCM (1 ml) was stirred at rt for 0.5 h and concentrated. The crude product was dissolved in THF and cooled in ice bath. To the mixture was added K$_2$CO$_3$ (2 M, 30 µl) and a solution of acryloyl chloride (5 mg) in THF. The resulting mixture was stirred at 0° C. for 30 min and purified by reversed phase preparative HPLC to give title compound 80 (2.1 mg) as off white solid. MS (ESI): m/z=490 [M+H]+.

Example 81

(R)-1-(1-acryloylpiperidin-3-yl)-4-amino-2-fluoro-3-(4-phenoxyphenyl)-1H-pyrrolo[2,3-d]pyridazin-7(6H)-one

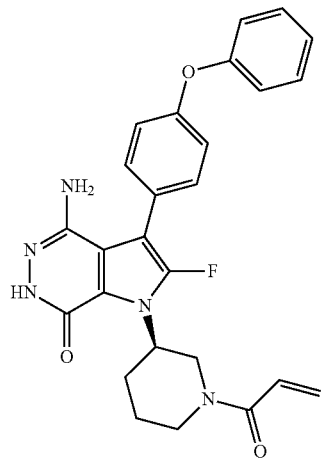

A mixture of 1g (120 mg, 0.23 mmol) and select flour (98.9 mg, 0.28 mmol) in CH$_3$CN (10 ml) was refluxed for 10 h. After cooled to room temperature, the solvents were removed. Water was added, the mixture was extracted with EtOAc three times. The combined organic extracts were washed with water, brine, dried over MgSO$_4$, filtered, and concentrated to give oil 81a (71 mg). MS (ESI): m/z=534 [M+H]+.

The title compound was made from 81a and via the similar conditions described in steps 1E~1G of Example 1. MS (ESI): m/z=474 [M+H]+.

Example 82

4-amino-1-[(3R)-1-[(E)-4-(dimethylamino)but-2-enoyl]-3-piperidyl]-2-fluoro-3-(4-phenoxyphenyl)-6H-pyrrolo[2,3-d]pyridazin-7-one

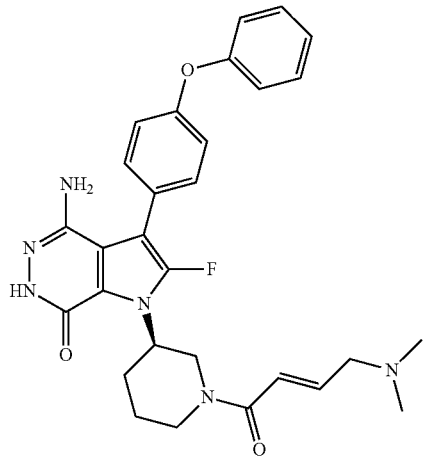

The title compound was made from (E)-4-(dimethylamino)but-2-enoic acid and corresponding amine (precursor of example 81) via the similar conditions described in step 16C of Example 16. MS (ESI): m/z=531 [M+H]+.

Example 83

(R)-1-(1-acryloylpiperidin-3-yl)-4-amino-2-chloro-3-(4-(2-fluorophenoxy)phenyl)-1H-pyrrolo[2,3-d]pyridazin-7(6H)-one

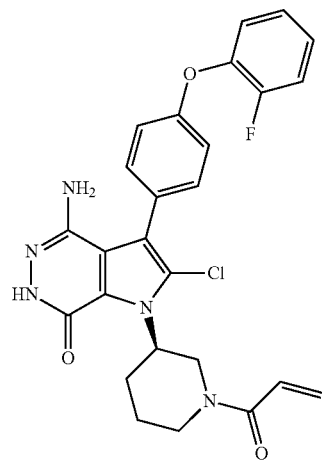

The title compound was prepared via the similar conditions described in Example 80. MS (ESI): m/z=508 [M+H]+.

Example 84

(R)-3-(4-amino-3-(4-(2,6-difluorophenoxy)phenyl)-7-oxo-6,7-dihydro-1H-pyrrolo[2,3-d]pyridazin-1-yl)piperidine-1-carbonitrile

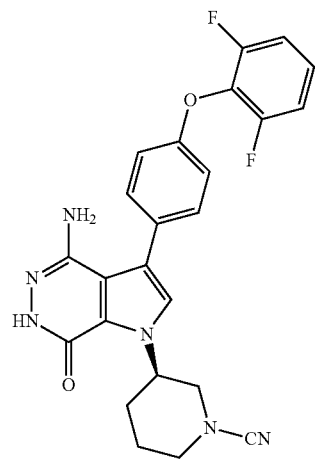

The title compound was prepared via the similar conditions described in Example 20. MS (ESI): m/z=463 [M+H]⁺.

Example 85

(R)-3-(4-amino-3-(3-fluoro-4-phenoxyphenyl)-7-oxo-6,7-dihydro-1H-pyrrolo[2,3-d]pyridazin-1-yl)piperidine-1-carbonitrile

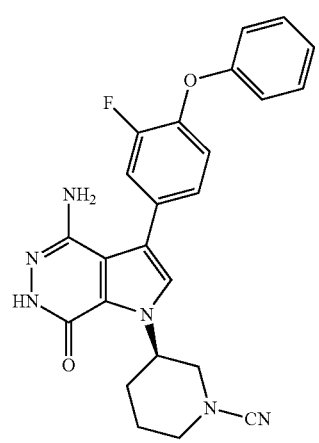

The title compound was prepared via the similar conditions described in Example 20. MS (ESI): m/z=445 [M+H]⁺.

Example 86

(R)-3-(4-amino-2-chloro-3-(4-(2-fluorophenoxy)phenyl)-7-oxo-6,7-dihydro-1H-pyrrolo[2,3-d]pyridazin-1-yl)piperidine-1-carbonitrile

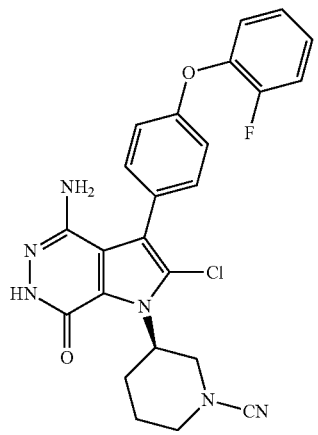

The title compound was prepared via the similar conditions described in Example 20, 80. MS (ESI): m/z=479 [M+H]⁺.

Example 87

(R)-3-(4-amino-3-(4-(2-fluorophenoxy)phenyl)-7-oxo-6,7-dihydro-1H-pyrrolo[2,3-d]pyridazin-1-yl)piperidine-1-carbonitrile

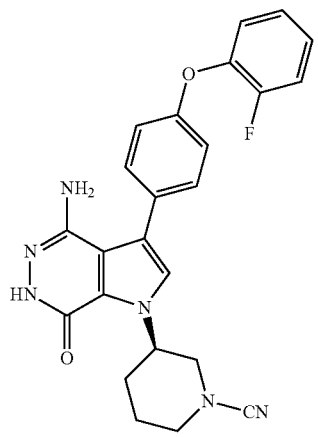

The title compound was prepared via the similar conditions described in Example 20. MS (ESI): m/z=445 [M+H]⁺.

Example 88

N-(3-(4-amino-7-oxo-3-(4-phenoxyphenyl)-6,7-dihydro-1H-pyrrolo[2,3-d]pyridazin-1-yl)phenyl)acrylamide

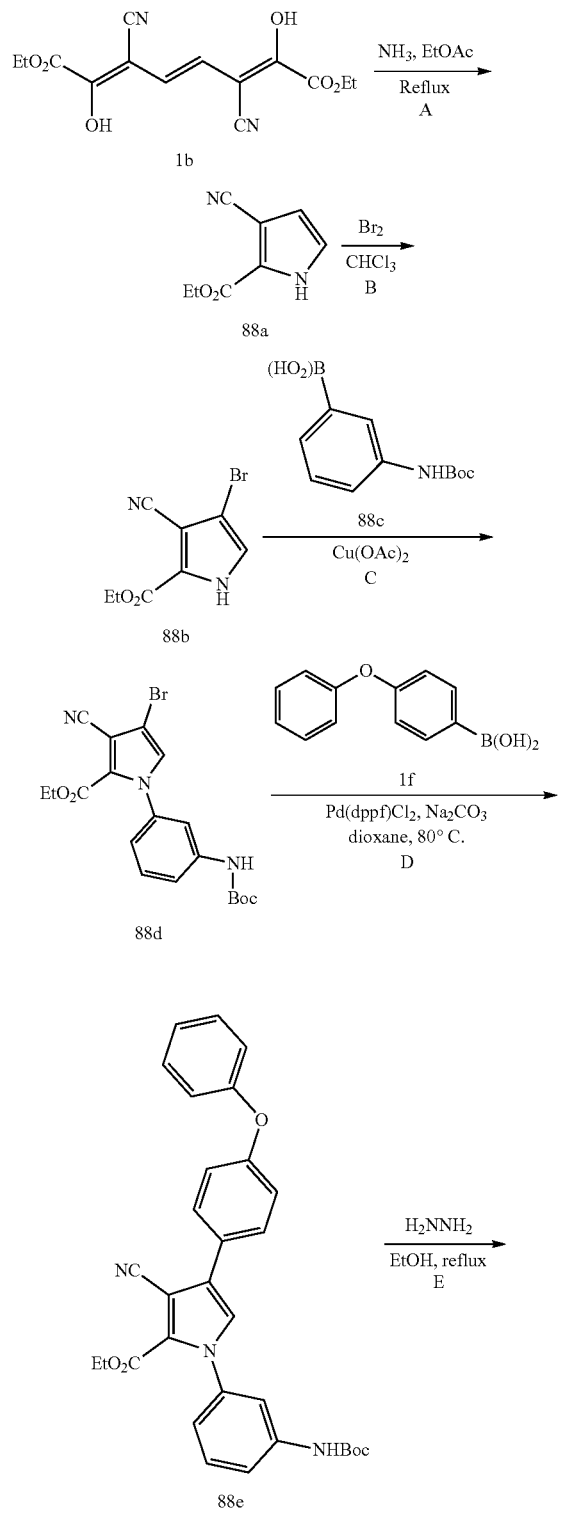

Step 88A

To a solution of 1b (1.62 g) in EtOAc (30 ml) at 60° C. was added dropwise a solution of 0.5 M NH$_3$ in dioxane (22 ml). The mixture was refluxed for 18 h. After cooled to room temperature, the solvents were removed. The residue was purified by silica gel chromatography to afford light yellow solid 88a (0.37 g).

Step 88B

To a solution of 88a (320 mg) in CHCl$_3$ (17 ml) at −20° C. was added dropwise a solution of Br$_2$ (350 mg) in CHCl$_3$ (3 ml). The mixture was stirred at lower than 10° C. for 5 h, and then quenched with a solution of 10% Na$_2$S$_2$O$_3$ and saturated solution of NaHCO$_3$. The two phases were separated; the aqueous phase was extracted with DCM three times. The combined organic layers were dried over Na$_2$SO$_4$, filtered and concentrated. The residue was purified by silica gel chromatography to give 88b (400 mg).

Step 88C

To a mixture of 88b (200 mg, 0.82 mmol), 88c (390 mg, 1.64 mmol) in DCM (10 ml) at 0° C. was added Cu(OAc)$_2$ (224 mg, 1.23 mmol) and pyridine (185 µl). The mixture stirred at rt for 20 h. Water was added, extracted with EtOAc twice. The organic extracts were washed with brine, dried over Na$_2$SO$_4$, filtered, and concentrated. The residue was purified by silica gel chromatography to give 88d (360 mg).

Step 88D

A mixture of 88d (133 mg, 0.306 mmol), 1f (131 mg, 0.612 mmol), K$_2$CO$_3$ (2M, 0.5 ml), and Pd(dppf)Cl$_2$ (49 mg, 0.06 mmol) in 1.4-dioxane (8 ml) was stirred in under $N_2$ at 80° C. for 18 h. Water was added, extracted with EtOAc twice. The organic extracts were washed with brine, dried over $Na_2SO_4$, filtered, and concentrated. The residue was purified by silica gel chromatography to give colorless oil 88e (135 mg). MS (ESI): m/z=524 [M+H]$^+$.

Step 88E

A mixture of 88e (130 mg) and $N_2H_4$ (1.2 ml) in EtOH (10 ml) was refluxed for 24 h. After cooled to room temperature, the solvents were removed. The residue was purified by silica gel chromatography to give white solid 88f (38 mg). MS (ESI): m/z=510 [M+H]$^+$.

Step 88F

A mixture of 88f (18 mg) and HCl solution (1 ml, 4 M in dioxane) was stirred at rt for 1 h and concentrated. The crude product was dissolved in THF and cooled in ice bath. To the mixture was added $K_2CO_3$ (2 M, 40 μl) and a solution of acryloyl chloride (4 mg) in THF. The resulting mixture was stirred at 0° C. for 20 min and purified by reversed phase preparative HPLC to give title compound 88 (7.2 mg) as white solid. MS (ESI): m/z=464 [M+H]$^+$.

Example 89

N-(3-(4-amino-3-(3-chloro-4-methoxyphenyl)-7-oxo-6,7-dihydro-1H-pyrrolo[2,3-d]pyridazin-1-yl)phenyl)acrylamide

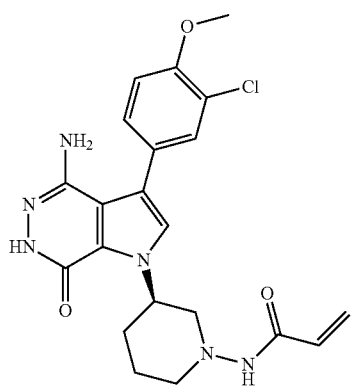

89

The title compound was made from 88d and (3-chloro-4-methoxyphenyl)boronic acid via the similar conditions described in steps 88D-88F of Example 88. MS (ESI): m/z=436 [M+H]$^+$.

Example 90

N-(4-(4-amino-7-oxo-3-(4-phenoxyphenyl)-6,7-dihydro-1H-pyrrolo[2,3-d]pyridazin-1-yl)phenyl)acrylamide

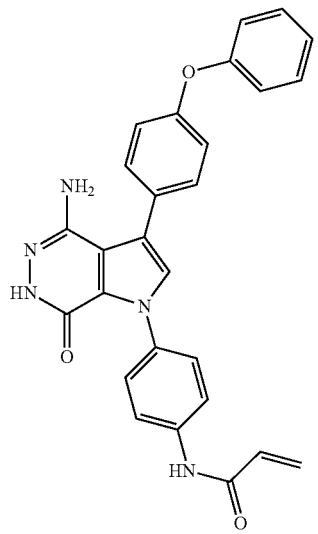

90

The title compound was made from 88b and (4-((tert-butoxycarbonyl)amino)phenyl)boronic acid via the similar conditions described in steps 88C-88F of Example 88. MS (ESI): m/z=464 [M+H]$^+$.

Example 91

N-(3-(4-amino-3-(4-(2-fluorophenoxy)phenyl)-7-oxo-6,7-dihydro-1H-pyrrolo[2,3-d]pyridazin-1-yl)phenyl)acrylamide

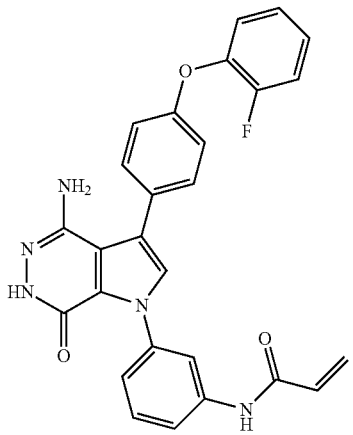

91

The title compound was made from 88d and (4-(2-fluorophenoxy)phenyl)boronic acid via the similar conditions described in steps 88D-88F of Example 88. MS (ESI): m/z=482 [M+H]$^+$.

Example 92

(E)-N-[3-[4-amino-3-[4-(2-fluorophenoxy)phenyl]-7-oxo-6H-pyrrolo[2,3-d]pyridazin-1-yl]phenyl]-4-(dimethylamino)but-2-enamide

Example 93

(R)-4-amino-1-(1-(but-2-ynoyl)pyrrolidin-3-yl)-3-(4-(2,6-difluorophenoxy)phenyl)-1H-pyrrolo[2,3-d]pyridazin-7(6H)-one

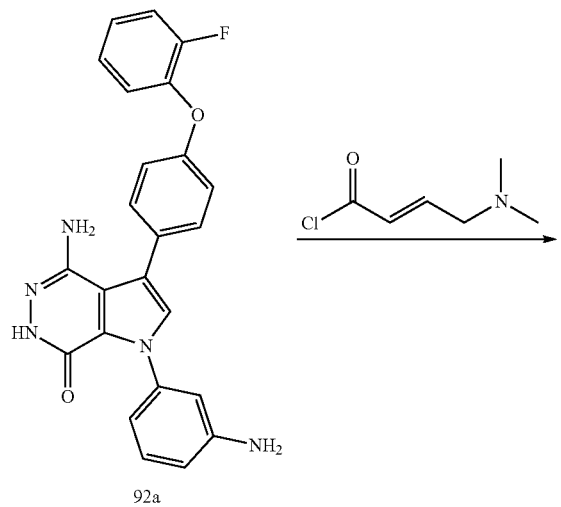

To a solution of 92a (10 mg) in DCM at 0° C. was added fresh prepared (E)-4-(dimethylamino)but-2-enoyl chloride. The resulting mixture was stirred at 0° C. for 0.5 h and purified by reversed phase preparative HPLC to give title compound 92 (1 mg). MS (ESI): m/z=539 [M+H]$^+$.

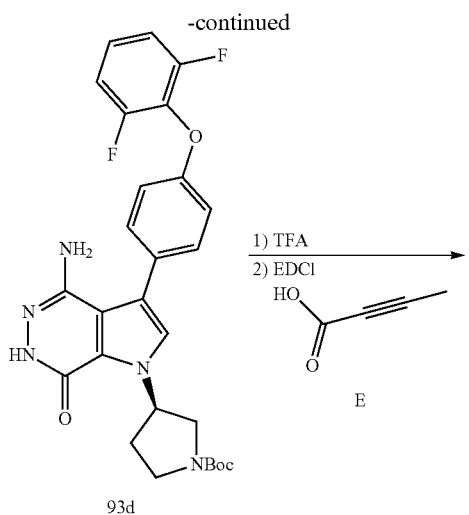

93d

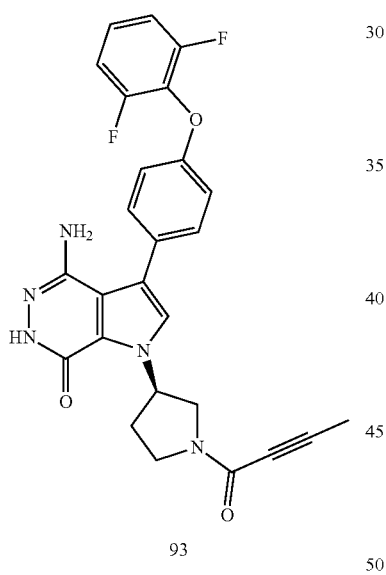

93

Step 93A

To a solution of 1b (1.5 g) in EtOAc (84 ml) at 60° C. was added dropwise a solution of (R)-tert-butyl 3-aminopyrrolidine-1-carboxylate (1.41 g) in EtOAc (21 ml). The mixture was refluxed for 4 h. After cooled to room temperature, the solvents were removed. The residue was purified by silica gel chromatography to afford 93a (0.686 g).

Step 93B

To a solution of 93a (0.686 g) in DCM (120 ml) at 0° C. was added slowly a solution of $Br_2$ (3.7 g) in DCM (5 ml). The mixture was stirred for 1.5 h, and then quenched with a solution of 10% $Na_2S_2O_3$ and saturated solution of $NaHCO_3$. The two phases were separated; the aqueous phase was extracted with DCM. The combined organic extracts were treated with excess $Boc_2O$, dried over $Na_2SO_4$, filtered and concentrated. The residue was purified by silica gel chromatography to give 93b (0.342 g).

Step 93C

A mixture of 93b (198 mg, 0.48 mmol), I2 (160 mg, 0.48 mmol) and $K_3PO_4.3H_2O$ (188 mg, 0.72 mmol) in 1.4-dioxane/water (10 ml/1 ml) was degassed with $N_2$. Next was added $Pd_2(dba)_3$ (22 mg, 0.024 mmol) and $P(Cy)_3$ (14 mg, 0.048 mmol). The resulting mixture was refluxed under $N_2$ for 16 h. After cooled to room temperature, the solid was filtered off, the filtrate was concentrated. The residue was purified by silica gel chromatography to give white solid 93c (59 mg). MS (ESI): m/z=538 $[M+H]^+$.

Step 93D

A mixture of 93c (72 mg, 0.13 mmol) and $N_2H_4.H_2O$ (1 mL) in EtOH (5 ml) was refluxed for 16 h. After cooled to room temperature, the solvents were removed. The residue was purified by silica gel chromatography to give white solid 93d (24 mg). MS (ESI): m/z=524 $[M+H]^+$.

Step 93E

To a solution of 93d (40 mg, 0.08 mmol) in DCM (5 ml) was added TFA (1 ml). The mixture was stirred at rt for 3 h and concentrated to give oil 93e (49 mg). To a solution of 93e (49 mg) in DCM (5 ml) was added but-2-ynoic acid (13 mg, 0.16 mmol), EDCI (31 mg, 0.16 mmol) and TEA (17 mg, 0.16 mmol). The resulting mixture was stirred at room temperature for 18 h and concentrated. The residue was purified by silica gel chromatography to give the title compound 93 (20 mg) as white solid. MS (ESI): m/z=490 $[M+H]^+$.

Example 94

(R)-4-amino-1-(1-(but-2-ynoyl)pyrrolidin-3-yl)-3-(4-(2-chloro-6-fluorophenoxy)phenyl)-1H-pyrrolo[2,3-d]pyridazin-7(6H)-one

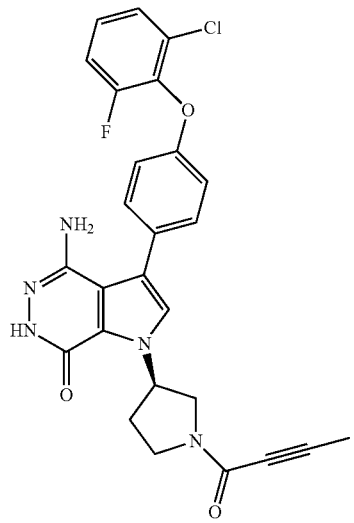

94

The title compound was made from 93b and intermediate 9 via the similar conditions described in steps 93C-93E of Example 93. MS (ESI): m/z=506 $[M+H]^+$.

Example 95

(R)-4-amino-1-(1-(but-2-ynoyl)pyrrolidin-3-yl)-3-(4-(2-fluorophenoxy)phenyl)-1H-pyrrolo[2,3-d]pyridazin-7(6H)-one

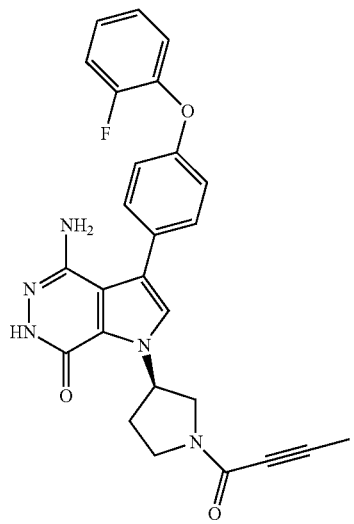

The title compound was made from 93b and ((4-(2-fluorophenoxy)phenyl)boronic acid via the similar conditions described in steps 93C-93E of Example 93. MS (ESI): m/z=472 [M+H]⁺.

Example 96

(R)-4-amino-1-(1-(but-2-ynoyl)pyrrolidin-3-yl)-3-(4-(2-chlorophenoxy)phenyl)-1H-pyrrolo[2,3-d]pyridazin-7(6H)-one

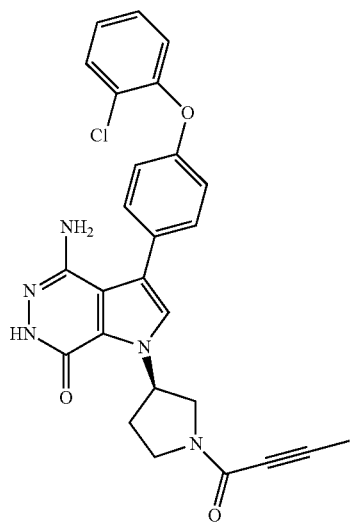

The title compound was made from 93b and intermediate 10 via the similar conditions described in steps 93C-93E of Example 93. MS (ESI): m/z=488 [M+H]⁺.

Example 97

(R)-4-amino-1-(1-(but-2-ynoyl)pyrrolidin-3-yl)-3-(4-phenoxyphenyl)-1H-pyrrolo[2,3-d]pyridazin-7(6H)-one

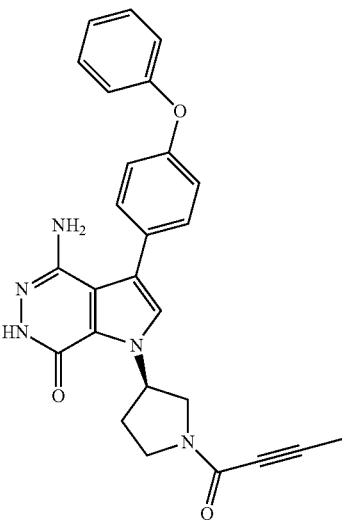

The title compound was made from 93b and (4-phenoxyphenyl)boronic acid via the similar conditions described in steps 93C-93E of Example 93. MS (ESI): m/z=454 [M+H]⁺.

Example 98

4-amino-1-((3S,4S)-1-(but-2-ynoyl)-4-methoxypyrrolidin-3-yl)-3-(4-(2-fluorophenoxy)phenyl)-1H-pyrrolo[2,3-d]pyridazin-7(6H)-one and Enantiomer

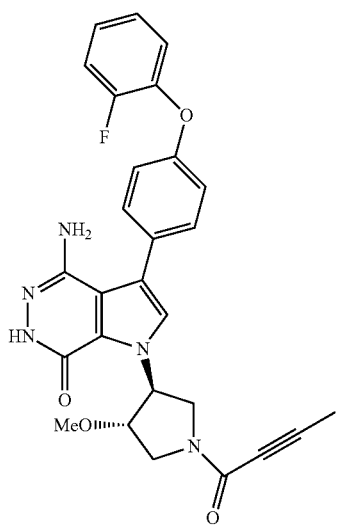

The title compound was made from trans-tert-butyl 3-amino-4-methoxypyrrolidine-1-carboxylate via the similar conditions described in Example 1. MS (ESI): m/z=502 [M+H]⁺.

Example 99

(R)-4-amino-1-(1-(4-(dimethylamino)but-2-ynoyl)pyrrolidin-3-yl)-3-(4-(2-fluorophenoxy)phenyl)-1H-pyrrolo[2,3-d]pyridazin-7(6H)-one

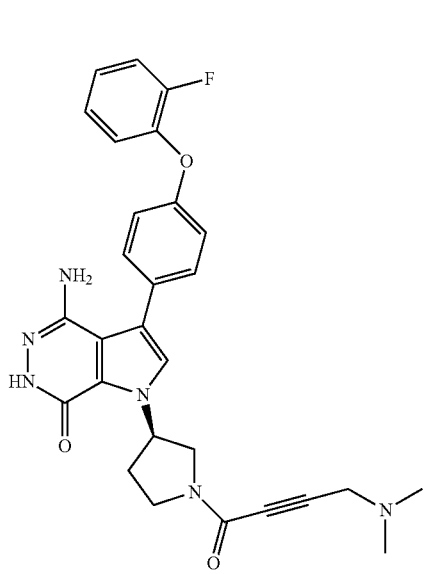

The title compound was prepared via the similar procedures described in Example 93. MS (ESI): m/z=515 [M+H]$^+$.

Example 100

N-(3-(4-amino-3-(4-(2-fluorophenoxy)phenyl)-7-oxo-6,7-dihydro-1H-pyrrolo[2,3-d]pyridazin-1-yl)cyclopentyl)but-2-ynamide

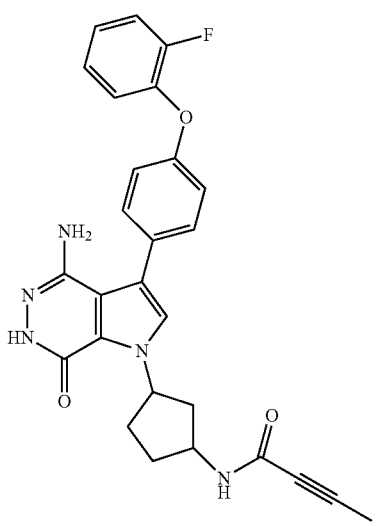

The title compound was prepared via the similar procedures described in Example 93. MS (ESI): m/z=486 [M+H]$^+$.

Example 101

(S)-4-amino-1-(1-(but-2-ynoyl)pyrrolidin-3-yl)-3-(4-(2-fluorophenoxy)phenyl)-1H-pyrrolo[2,3-d]pyridazin-7(6H)-one

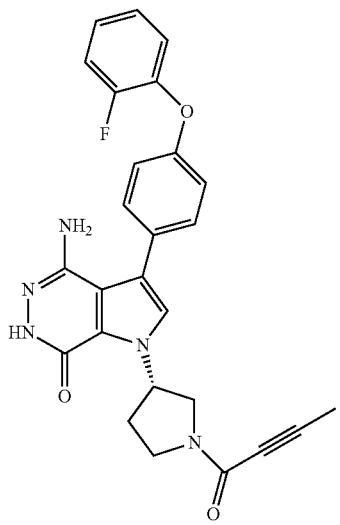

The title compound was prepared via the similar procedures described in Example 93. MS (ESI): m/z=472 [M+H]$^+$.

Example 102

N-((1s,4s)-4-(4-amino-3-(4-(2-fluorophenoxy)phenyl)-7-oxo-6,7-dihydro-1H-pyrrolo[2,3-d]pyridazin-1-yl)cyclohexyl)but-2-ynamide

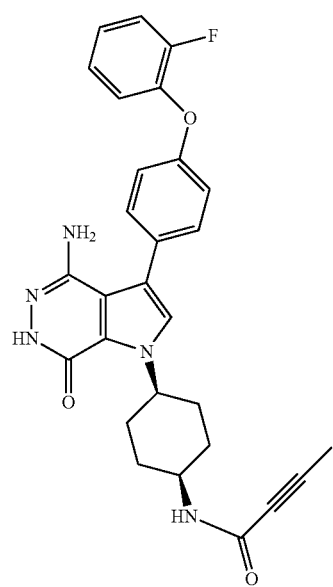

The title compound was prepared via the similar procedures described in Example 1. MS (ESI): m/z=500 [M+H]$^+$.

Example 103

N-((1r,4r)-4-(4-amino-3-(4-(2-fluorophenoxy)phenyl)-7-oxo-6,7-dihydro-1H-pyrrolo[2,3-d]pyridazin-1-yl)cyclohexyl)but-2-ynamide

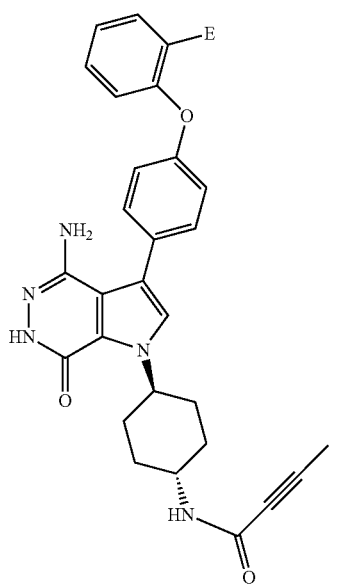

The title compound was prepared via the similar procedures described in Example 1. MS (ESI): m/z=500 [M+H]⁺.

Example 104

N-((1s,4s)-4-(4-amino-3-(4-(2-fluorophenoxy)phenyl)-7-oxo-6,7-dihydro-1H-pyrrolo[2,3-d]pyridazin-1-yl)cyclohexyl)acrylamide

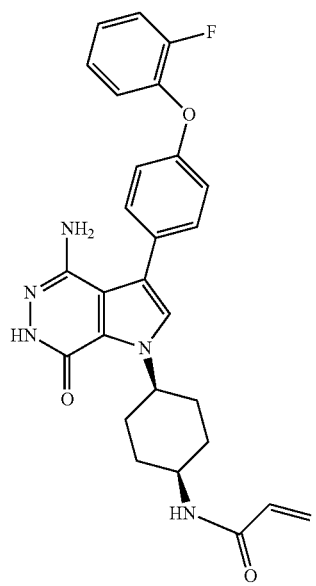

The title compound was prepared via the similar procedures described in Example 1. MS (ESI): m/z=488 [M+H]⁺.

Example 105

N-((1r,4r)-4-(4-amino-3-(4-(2-fluorophenoxy)phenyl)-7-oxo-6,7-dihydro-1H-pyrrolo[2,3-d]pyridazin-1-yl)cyclohexyl)acrylamide

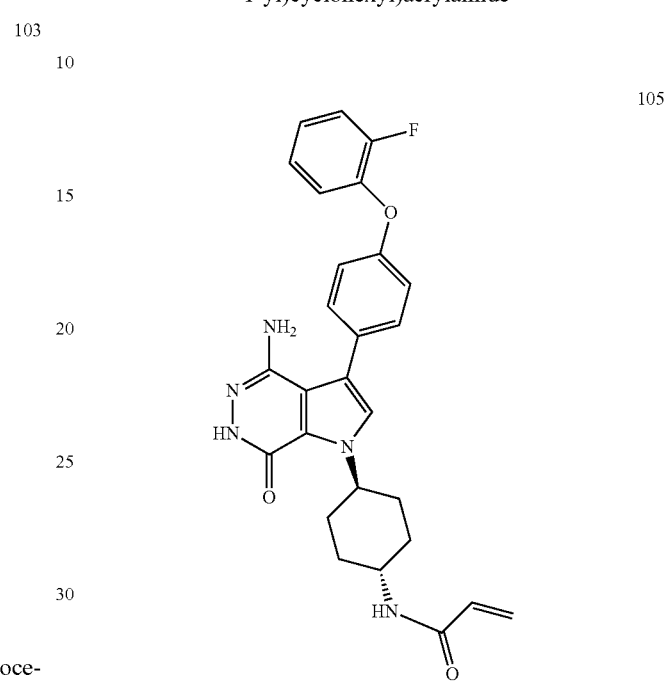

The title compound was prepared via the similar procedures described in Example 1. MS (ESI): m/z=488 [M+H]⁺.

Example 106

(R)-1-(1-acryloylpyrrolidin-3-yl)-4-amino-3-(4-(2-fluorophenoxy)phenyl)-1H-pyrrolo[2,3-d]pyridazin-7(6H)-one

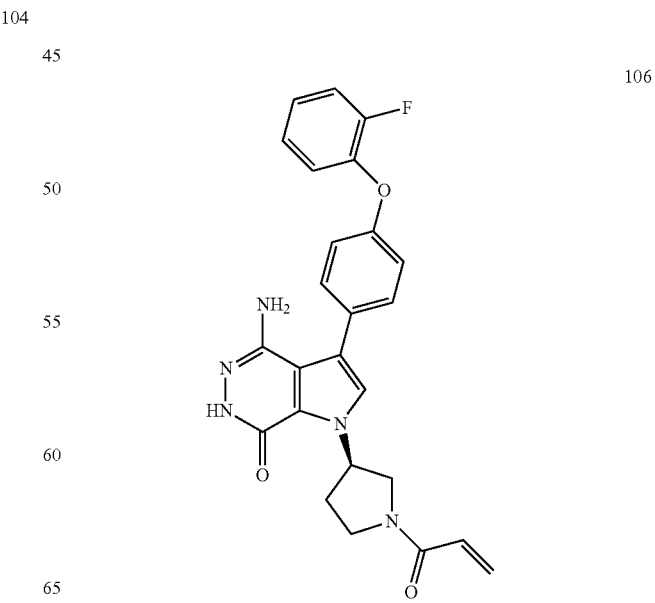

The title compound was prepared via the similar procedures described in Example 1. MS (ESI): m/z=460 [M+H]⁺.

Example 107

(R)-3-(4-amino-7-oxo-3-(4-phenoxyphenyl)-6,7-dihydro-1H-pyrrolo[2,3-d]pyridazin-1-yl)pyrrolidine-1-carbonitrile

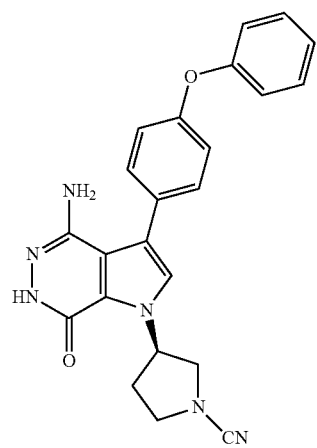

107

The title compound was prepared via the similar conditions described in Example 20. MS (ESI): m/z=413 [M+H]⁺.

Example 108

3-(4-amino-3-(4-(2-fluorophenoxy)phenyl)-7-oxo-6,7-dihydro-1H-pyrrolo[2,3-d]pyridazin-1-yl)piperidine-1-carbonitrile

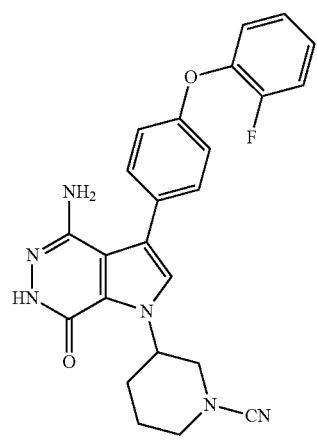

108

The title compound was prepared via the similar conditions described in Example 20. MS (ESI): m/z=445 [M+H]⁺.

Example 109

(R)-1-(1-acryloylpiperidin-3-yl)-4-amino-3-(4-(2-fluorophenoxy)phenyl)-1H-pyrazolo[3,4-d]pyridazin-7(6H)-one

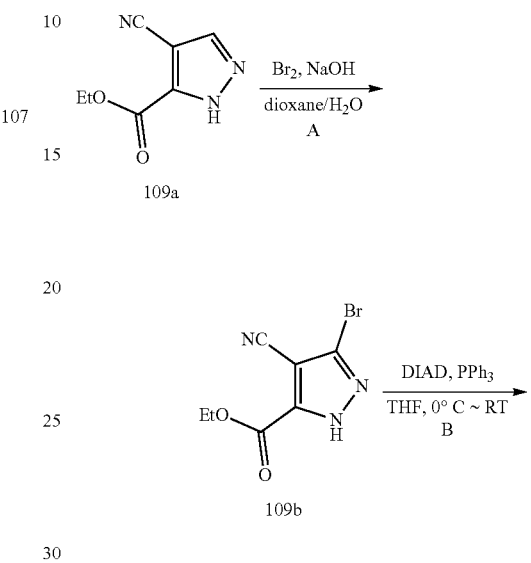

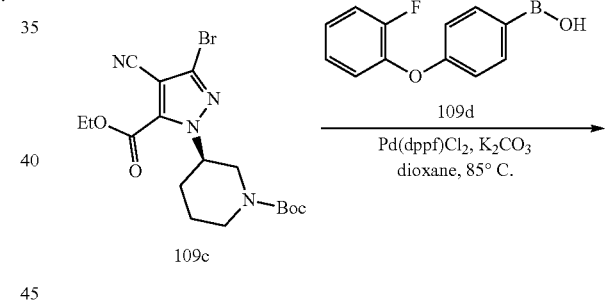

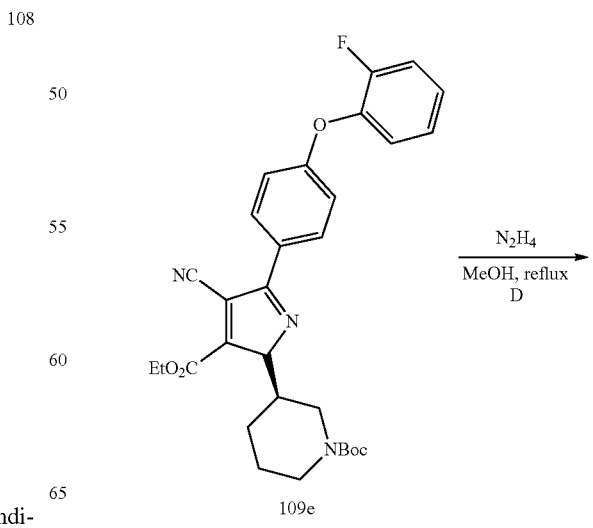

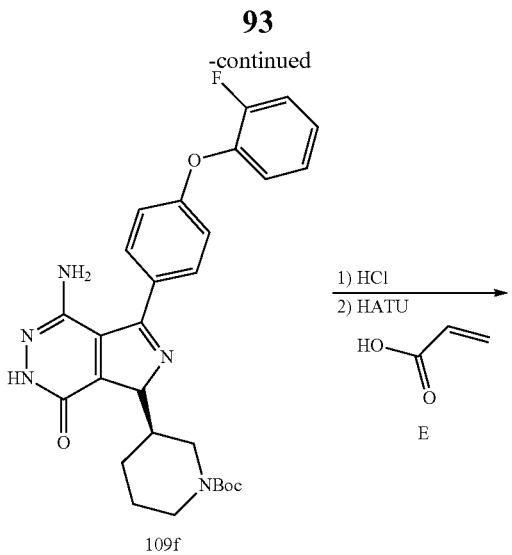

109f

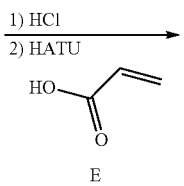

1) HCl
2) HATU

Step 109A

To a mixture of 109a (200 mg) and NaOH (2 M, 1.2 ml) in dioxane (4 ml) at 0° C. was added a solution of Br$_2$ (380 mg) in dioxane (2 ml). The mixture was stirred at rt for 1 h and concentrated. The residue was purified by silica gel chromatography to give 109b (340 mg).

Step 109B

To a solution of 109b (50 mg), (S)-tert-butyl 3-hydroxypiperidine-1-carboxylate (80 mg) and PPh$_3$ (100 mg) in THF (5 ml) at 0° C. was added DIAD (80 mg). The mixture was stirred at rt for 18 h and concentrated. The residue was purified by silica gel chromatography to give 109c (76 mg).

Step 109C

A mixture of 109c (70 mg), 109d (114 mg), K$_2$CO$_3$ (113 mg), and Pd(dppf)Cl$_2$ (66 mg) in dioxane/water (5 ml/0.5 ml) was stirred in under N$_2$ at 85° C. for 3 h. After cooled to room temperature, the solvents were removed. The residue was purified by silica gel chromatography to give 109e (100 mg). MS (ESI): m/z=535 [M+H]$^+$.

Step 109D

A mixture of 109e (100 mg) and N$_2$H$_4$ (2.5 ml) in MeOH (5 ml) was refluxed for 3 h. After cooled to room temperature, the solvents were removed. The residue was purified by silica gel chromatography to give 109f (70 mg). MS (ESI): m/z=521 [M+H]$^+$.

Step 109E

A mixture of 109f (70 mg) and HCl solution (4 ml, 4M in dioxane) was stirred at rt for 0.5 h and concentrated to give 109g (100 mg) which was used directly in next step.

To a solution of 109g (9 mg) in DMF (1 ml) was added DIEA (13 mg), acid (6 mg) and HATU (18 mg). The resulting mixture was stirred at room temperature for 0.5 h and purified by reversed phase preparative HPLC to give title compound 109 (3.1 mg). MS (ESI): m/z=475 [M+H].

Example 110

(R)-1-(1-acryloylpiperidin-3-yl)-4-amino-3-(4-phenoxyphenyl)-1H-pyrazolo[3,4-d]pyridazin-7(6H)-one

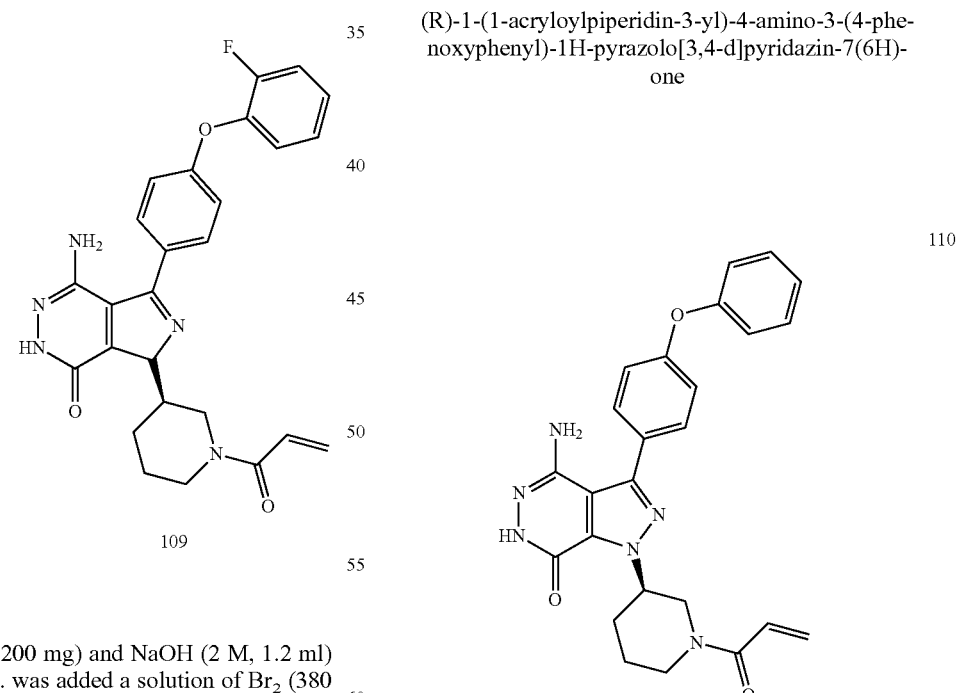

The title compound was made was made from 109c and (4-phenoxyphenyl)boronic acid via the similar conditions described in steps 109C-109E of Example 109. MS (ESI): m/z=457 [M+H]$^+$.

Example 111

(R)-4-amino-1-(1-(but-2-ynoyl)pyrrolidin-3-yl)-3-(4-phenoxyphenyl)-1H-pyrazolo[3,4-d]pyridazin-7(6H)-one

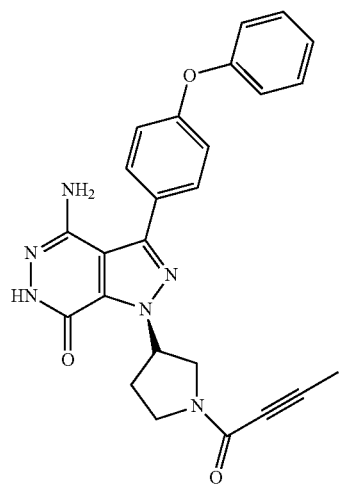

111

The title compound was made was made from 109b and proper reagents via the similar conditions described in steps 109B-109E of Example 109. MS (ESI): m/z=455 [M+H]$^+$.

Example 112

(R)-4-amino-1-(1-(but-2-ynoyl)pyrrolidin-3-yl)-3-(4-(2-fluorophenoxy)phenyl)-1H-pyrazolo[3,4-d]pyridazin-7(6H)-one

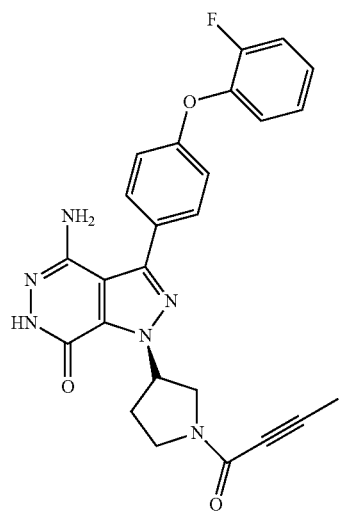

112

The title compound was made was made from 109b and proper reagents via the similar conditions described in steps 109B-109E of Example 109. MS (ESI): m/z=473 [M+H]$^+$.

Example 113

(R)-4-amino-1-(1-(but-2-ynoyl)pyrrolidin-3-yl)-3-(4-(2,6-difluorophenoxy)phenyl)-1H-pyrazolo[3,4-d]pyridazin-7(6H)-one

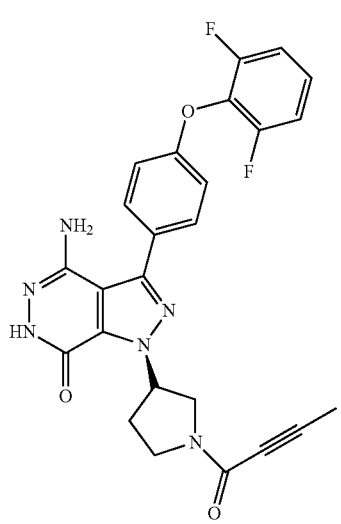

113

The title compound was made was made from 109b and proper reagents via the similar conditions described in steps 109B-109E of Example 109. MS (ESI): m/z=491 [M+H]$^+$.

Example 114

(S)-1-(1-acryloylpiperidin-3-yl)-4-amino-3-(4-(2,6-difluorophenoxy)phenyl)-1H-pyrrolo[2,3-d]pyridazin-7(6H)-one

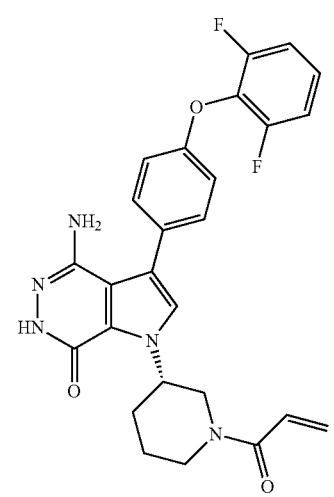

114

The title compound was prepared via the similar conditions described in Example 58. MS (ESI): m/z=492 [M+H]$^+$.

Example 115

(R)-4-amino-3-(4-(2,6-difluorophenoxy)phenyl)-1-(1-propionylpiperidin-3-yl)-1H-pyrrolo[2,3-d]pyridazin-7(6H)-one

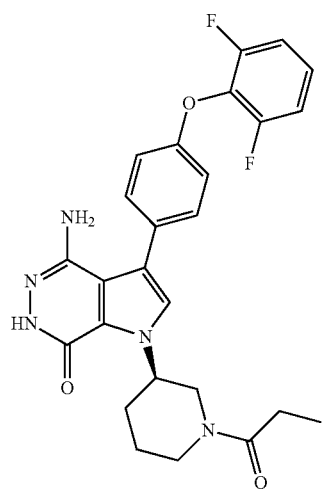

The title compound was prepared from compound 58 via the similar conditions described in Example 19. MS (ESI): m/z=494 [M+H]$^+$.

Example 116

4-amino-3-[4-(2,6-difluorophenoxy)phenyl]-1-[(3R)-1-[(E)-but-2-enoyl]-3-piperidyl]-6H-pyrrolo[2,3-d]pyridazin-7-one

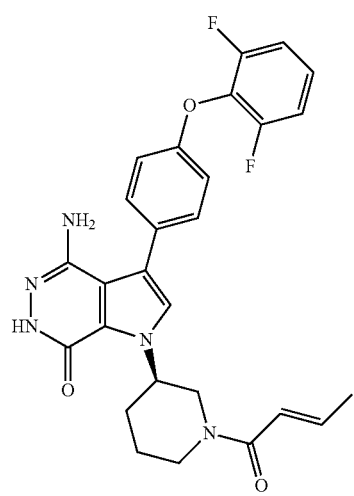

The title compound was made from (E)-but-2-enoic acid and amine 58c via the similar conditions described in step 58C of Example 58. MS (ESI): m/z=506 [M+H]$^+$.

Example 117

(R)-4-amino-1-(1-(but-2-ynoyl)piperidin-3-yl)-3-(4-(2,6-difluorophenoxy)phenyl)-1H-pyrrolo[2,3-d]pyridazin-7(6H)-one

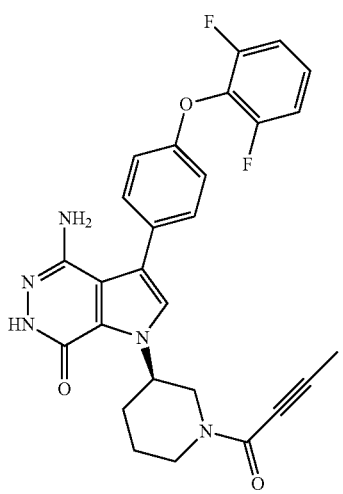

The title compound was made from but-2-ynoic acid and amine 58c via the similar conditions described in step 58C of Example 58. MS (ESI): m/z=504 [M+H]$^+$.

Example 118

(R)-4-amino-1-(1-butyrylpyrrolidin-3-yl)-3-(4-(2,6-difluorophenoxy)phenyl)-1H-pyrrolo[2,3-d]pyridazin-7(6H)-one

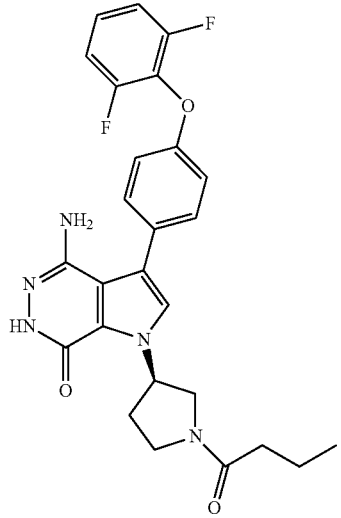

The title compound was prepared compound 93 via the similar conditions described in Example 19. MS (ESI): m/z=494 [M+H]$^+$.

Example 119

Evaluation of BTK Activity

Methods for Biochemical and Cell-Based Assays:

Btk Kinase Assay—The Btk kinase assay was performed using a ADP-Glo Btk kinase assay kit purchased from Promega (Madison, Wis.). The assay was conducted according to the protocols provided in the assay kit. In brief, the enzyme reaction was carried out in the kinase reaction buffer containing Btk (2 ng/μl), ATP (1.2 μM), poly GT peptide (0.3 μM), DTT (40 nM), MnCl2 (1.4 mM), and 1×kinase buffer (included in the kit) in the presence or absence of the tested articles at various concentrations in 384-well plate at room temperature (22±1° C.) for 60 minutes. The final reaction volume for each reaction was 10 μl. Then, 4 μl of ADP-Glo reagent (included in the kit) was added into the reaction and the plate was further incubated for another 40 minutes to terminate the reaction and deplete the remaining ATP. Finally, 10 μl of the kinase detection reagent was added into each reaction to simultaneously convert ADP to ATP and allow the newly synthesized ATP to be measured by a plate-reading luminometer (Victor X5 2030 multilabel reader, PerkinElmer). IC50 value was calculated using appropriate programs in GraphPad Prism by plotting the logarithm of the concentration versus percent inhibition as compared with a vehicle (DMSO) control. The IC50 values for the example compounds are shown in Table 4.

Cell proliferation assay: TMD-8 and SU-DHL-1 cells were maintained at 37° C. in a humidified atmosphere with 5% $CO_2$ in the recommended medium and serum concentrations. For cell proliferation assay, cells were seeded in 96-well pates at a density of 5,000 to 10,000 cells per well and cultured overnight at 37° C. in recommended medium supplemented with 5-10% FBS. On the next day, the test articles at various concentrations or vehicle control (0.5% DMSO) were added into cell culture. After 5-day treatment, the growth of cells was assayed by the CellTiter-Glo® Luminestceaent Cell Viability Assay (Promega). $IC_{50}$ values were calculated using GraphPad Prism by plotting the logarithm of the concentration versus percent inhibition of cell growth as compared with the vehicle control. The $IC_{50}$ values for the example compounds are shown in Table 4.

TABLE 4

Biological Testing Results

| Example | BTK enzyme $IC_{50}$ (μM) | TMD8 cells growth $IC_{50}$ (μM) |
|---|---|---|
| 1 | A | A |
| 2 | A | A |
| 3 | B | B |
| 4 | B | B |
| 5 | B | B |
| 6 | B | A |
| 7 | C | — |
| 8 | B | B |
| 9 | C | — |
| 10 | B | B |
| 11 | B | A |
| 12 | B | A |
| 13 | A | A |
| 14 | A | A |
| 15 | B | A |
| 16 | A | B |
| 17 | B | B |
| 18 | A | A |
| 19 | B | B |
| 20 | B | A |

TABLE 4-continued

Biological Testing Results

| Example | BTK enzyme $IC_{50}$ (μM) | TMD8 cells growth $IC_{50}$ (μM) |
|---|---|---|
| 21 | C | — |
| 22 | B | B |
| 23 | B | B |
| 24 | B | B |
| 25 | B | B |
| 26 | A | A |
| 27 | A | A |
| 28 | A | A |
| 29 | B | A |
| 30 | B | B |
| 31 | A | B |
| 32 | B | B |
| 33 | A | A |
| 34 | A | A |
| 35 | A | A |
| 36 | A | B |
| 37 | C | — |
| 38 | A | A |
| 39 | A | A |
| 40 | B | B |
| 41 | B | B |
| 42 | C | — |
| 43 | B | B |
| 44 | B | B |
| 45 | A | A |
| 46 | B | B |
| 47 | A | A |
| 48 | B | B |
| 49 | B | B |
| 50 | B | B |
| 51 | A | B |
| 52 | A | C |
| 53 | A | B |
| 54 | A | B |
| 55 | A | A |
| 56 | A | A |
| 57 | A | A |
| 58 | A | A |
| 59 | B | A |
| 60 | B | B |
| 61 | B | B |
| 62 | B | A |
| 63 | A | A |
| 64 | B | A |
| 65 | B | B |
| 66 | B | A |
| 67 | A | B |
| 68 | B | A |
| 69 | A | A |
| 70 | B | A |
| 71 | A | A |
| 72 | B | B |
| 73 | B | B |
| 74 | B | A |
| 75 | A | B |
| 76 | B | A |
| 77 | A | A |
| 78 | A | A |
| 79 | A | A |
| 80 | B | B |
| 81 | B | A |
| 82 | A | A |
| 83 | C | — |
| 84 | B | A |
| 85 | B | A |
| 86 | C | — |
| 87 | A | A |
| 88 | A | A |
| 89 | B | B |
| 90 | B | A |
| 91 | B | A |
| 92 | B | A |
| 93 | B | A |
| 94 | B | A |
| 95 | B | A |

TABLE 4-continued

Biological Testing Results

| Example | BTK enzyme IC$_{50}$ (μM) | TMD8 cells growth IC$_{50}$ (μM) |
|---|---|---|
| 96 | B | B |
| 97 | B | A |
| 98 | B | B |
| 99 | A | B |
| 100 | B | A |
| 101 | C | — |
| 102 | B | A |
| 103 | B | A |
| 104 | B | A |
| 105 | B | B |
| 106 | B | A |
| 107 | A | C |
| 108 | A | A |
| 109 | B | A |
| 110 | B | A |
| 111 | A | A |
| 112 | B | A |
| 113 | B | A |
| 114 | B | A |
| 115 | B | B |
| 116 | B | B |
| 117 | B | B |
| 118 | C | — |

A ≤ 0.01 μM;
0.01 μM < B ≤ 1 μM;
1 μM < C < 100 μM

Pharmacokinetic Tests: The tested articles were given to Sprague-Dawley rats or Beagle dogs by intravenous and oral administration. Plasma samples were prepared from blood samples which were collected at various time points. The plasma concentrations of the tested articles were determined by specific LC-MS/MS analytical methods. Pharmacokinetic parameters were calculated with WinNonlin®. The pharmacokinetic test results for the example compounds are shown in Table 5 (rat) and Table 6 (dog) below.

TABLE 5

Rat PK parameters of selected examples.

| Example | 58 | | 93 | |
|---|---|---|---|---|
| Dose | IV (0.5 mg/kg) | PO (5 mg/kg) | IV (0.5 mg/kg) | PO (5 mg/kg) |
| Cmax(ng/ml) | 1509 | 1297 | 710 | 914 |
| AUC 0-t (ng/ml*h) | 1511 | 6837 | 395 | 2290 |
| t½ (h) | 0.64 | 4.09 | 0.63 | 4.62 |
| CLz/F (ml/min/kg) | 5.45 | 11.0 | 22.9 | 39.2 |
| Vz/F(ml/kg) | 301 | 3827 | 1371 | 15421 |
| F % | — | 51.9% | — | 58.1% |

TABLE 6

Dog PK parameters of selected examples.

| Example | 58 | | 93 | |
|---|---|---|---|---|
| Dose | IV (0.2 mg/kg) | PO (2 mg/kg) | IV (0.5 mg/kg) | PO (2 mg/kg) |
| Cmax(ng/ml) | 145 | 656 | 212 | 315 |
| AUC 0-t (ng/ml*h) | 94.4 | 1094 | 525 | 1290 |

TABLE 6-continued

Dog PK parameters of selected examples.

| Example | 58 | | 93 | |
|---|---|---|---|---|
| t½(h) | 0.43 | 0.66 | 1.5 | 1.78 |
| CLz/F (ml/min/kg) | 35.4 | 31.1 | 15.9 | 26.3 |
| Vz/F(ml/kg) | 1281 | 1753 | 2050 | 4010 |
| F % | — | 114% | — | 61.6% |

In Vivo Efficacy Study: The in vivo antitumor activity was assessed with TMD-8 xenograft model. In brief, TMD-8 cells were implanted into NOD-SCID nude mice and allowed to grow to the designated size (c.a. 100-200 mm$^3$) before treatment. The tested articles were given orally at various dose levels once daily (QD) or twice a day (BID) for 14 consecutive days. Tumor and body weight were measured during the experiments, and tumor volumes were estimated from the formula [length/2]×[width$^2$]. Established tumors in each animal were individually normalized to their size at the start of the experiment, and the data were calculated as the change in tumor volume relative to the day 0 volume by the use of the relative tumor volume (RTV) formula, RTV=TV$_x$/TV$_0$, where TV$_x$ is the tumor volume on any day and TV$_0$ is the tumor volume at the initiation of dosing. Significant suppression of tumor growth was observed with examples 58 (98% tumor growth inhibition rate) and 93 (80% tumor growth inhibition rate).

What is claimed is:

1. A compound of formula (I), including tautomers, rotamers, geometric isomers, diastereomers, racemates, and enantiomers, a pharmaceutically acceptable salt, a solvate, or a hydrate thereof,

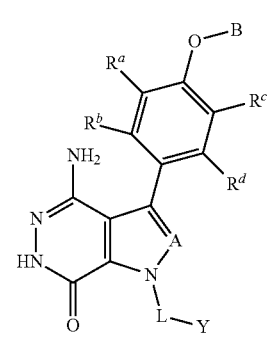

I wherein A is selected from the group consisting of CR$^0$ and N; and wherein R$^0$ is selected from the group consisting of hydrogen, halogen, and alkyl;

R$^a$, R$^b$, R$^c$ and R$^d$ are independently selected from the group consisting of hydrogen, halogen, and alkoxyl;

B is selected from the group consisting of hydrogen, C$_1$-C$_6$ alkyl, aryl, and B is either unsubstituted or substituted with at least one member selected from the group consisting of halogen, and alkoxyl;

L is alkylene, or absent; and

Y is selected from the group consisting of:

i)

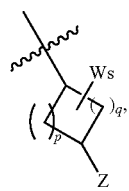

wherein W is independently selected from the group consisting of halogen, hydroxyl, cyano, alkyl, and alkoxyl;

p=1, 2, or 3;

q=0, 1, or 2;

s=0, 1, 2, or 3; and

Z is selected from the group consisting of —NHC(O)R$^{12}$ and —NHS(O)$_2$R$^{14}$; and wherein R$^{12}$ and R$^{14}$ are independently selected from the group consisting of alkyl, cycloalkyl, alkenyl, cycloalkenyl, and alkynyl;

ii)

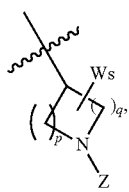

wherein W is independently selected from the group consisting of halogen, hydroxyl, cyano, alkyl, and alkoxyl;

p=1, 2, or 3;

q=0, 1, or 2;

s =0, 1, 2, or 3; and

Z is selected from the group consisting of CN, —C(O)R$^{11}$, and —S(O)$_2$R$^{13}$; and wherein R$^{11}$, and R$^{13}$ are independently selected from the group consisting of alkyl, cycloalkyl, alkenyl, cycloalkenyl, and alkynyl; or Z is selected from the group consisting of —C(O)CH═CH$_2$, —C(O)CH═CHCH$_2$N(CH$_3$)$_2$, —C(O)CH═CHCH$_2$N(CH$_3$)(COOC(CH$_3$)$_3$; —C(O)CH═CHCH$_2$NH(CH$_3$), —C(O)CH$_2$CH$_3$, —C(O)CH$_2$CH$_2$CH$_3$,

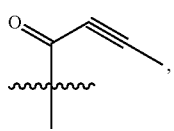 [SMILES: *C(=O)C#CC]

C(O)CH$_2$CH$_2$Cl,

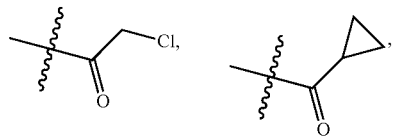 [SMILES: *C(=O)CCl ; *C(=O)C1CC1 ; ","]

—C(O)CH$_2$CN,

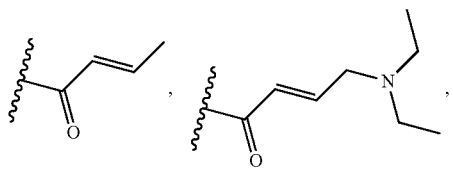

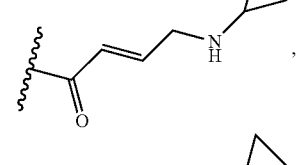

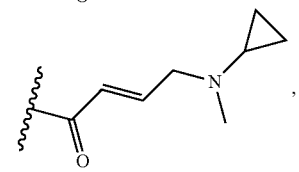

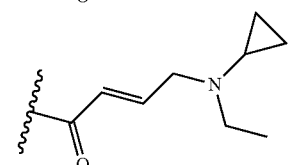

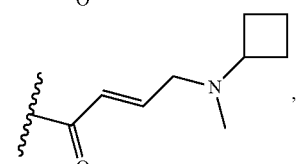

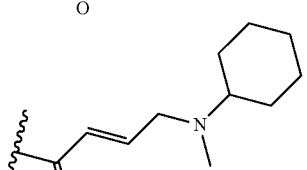

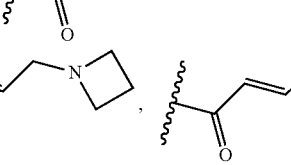

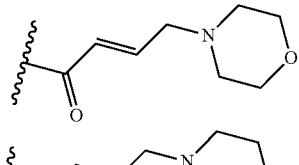

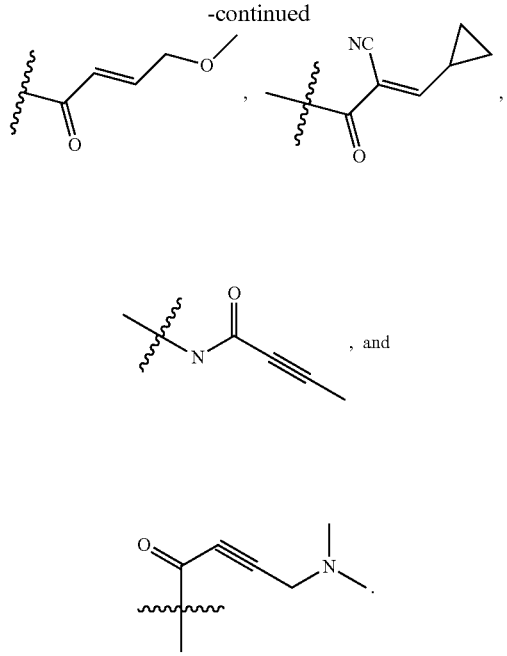

iii)

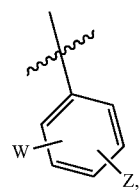

wherein W is selected from the group consisting of halogen, hydroxyl, cyano, alkyl, and alkoxyl; and
Z is —NHC(O)$R^{12}$; and wherein $R^{12}$ is selected from the group consisting of alkyl, cycloalkyl, alkenyl, cycloalkenyl, and alkynyl;

iv)

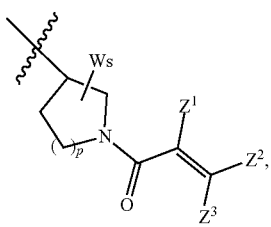

wherein W is independently selected from halogen, hydroxyl, cyano, alkyl, and alkoxyl;
p =1 or 2;
s =0, 1, 2, or 3;
$Z^1$ is selected from the group consisting of hydrogen, halogen, cyano, and alkyl; and
$Z^2$ and $Z^3$ are independently selected from the group consisting of hydrogen, alkyl, cycloalkyl, heterocycloalkyl, —$CH_2$O-alkyl, —$CH_2NR^{16}R^{17}$;
wherein $R^{16}$ and $R^{17}$ are independently selected from the group consisting of hydrogen, alkyl, cycloalkyl, and heterocycloalkyl;

wherein heterocycloalkyl is selected from the group consisting of morpholinyl, oxazolidinyl, piperazinyl, piperidinyl, pyrrolidinyl, tetrahydrofuryl, thiomorpholinyl, and indolinyl;

wherein $R^{16}$ and $R^{17}$ can combine with N to which they are attached to form a heterocyclic ring selected from the group consisting of morpholinyl, oxazolidinyl, piperazinyl, piperidinyl, pyrrolidinyl, thiomorpholinyl and indolinyl; and wherein $Z^1$ and $Z^2$ can join together to form a bond; and v) bicyclo[3.2.1]octanyl.

2. The compound of claim 1, a pharmaceutically acceptable salt, a solvate, or a hydrate thereof, wherein A is selected from the group consisting CH, CF, CCl and N.

3. The compound of claim 1, a pharmaceutically acceptable salt, a solvate, or a hydrate thereof, wherein at least one of $R^a$, $R^b$, $R^c$ and $R^d$ is selected from the group consisting of hydrogen, F, Cl, and methoxyl.

4. The compound of claim 1, a pharmaceutically acceptable salt, a solvate, or a hydrate thereof, wherein $R^a$, $R^b$, $R^c$ and $R^d$ are hydrogen.

5. The compound of claim 1, a pharmaceutically acceptable salt, a solvate, or a hydrate thereof, wherein B is unsubstituted or substituted $C_1$-$C_6$ alkyl.

6. The compound of claim 1, a pharmaceutically acceptable salt, a solvate, or a hydrate thereof, wherein B is unsubstituted or substituted aryl.

7. The compound of claim 1, a pharmaceutically acceptable salt, a solvate, or a hydrate thereof, wherein B is unsubstituted or substituted phenyl.

8. The compound of claim 1, a pharmaceutically acceptable salt, a solvate, or a hydrate thereof, wherein B is phenyl substituted with at least one member selected from the group consisting of F, Cl, and methoxyl.

9. The compound of claim 1, a pharmaceutically acceptable salt, a solvate, or a hydrate thereof, wherein B is phenyl substituted with two F.

10. The compound of claim 1, a pharmaceutically acceptable salt, a solvate, or a hydrate thereof, wherein B is phenyl substituted with two Cl.

11. The compound of claim 1, a pharmaceutically acceptable salt, a solvate, or a hydrate thereof, wherein B is phenyl substituted with one Cl and one F.

12. The compound of claim 1, a pharmaceutically acceptable salt, a solvate, or a hydrate thereof, wherein L is absent.

13. The compound of claim 1, a pharmaceutically acceptable salt, a solvate, or a hydrate thereof, wherein L is methylene.

14. The compound of claim 1, a pharmaceutically acceptable salt, a solvate, or a hydrate thereof, wherein Y is selected from the group consisting of piperidinyl, phenyl, bicyclo[3.2.1]octanyl, azetidinyl, and pyrrolidinyl.

15. The compound of claim 1, a pharmaceutically acceptable salt, a solvate, or a hydrate thereof, wherein the compound has more R-form than S-form.

16. The compound of claim 1, a pharmaceutically acceptable salt, a solvate, or a hydrate thereof, wherein the compound has more S-form than R-form.

17. A compound of formula (II), including tautomers, rotamers, geometric isomers, diastereomers, racemates, and enantiomers, a pharmaceutically acceptable salt, a solvate, or a hydrate thereof,

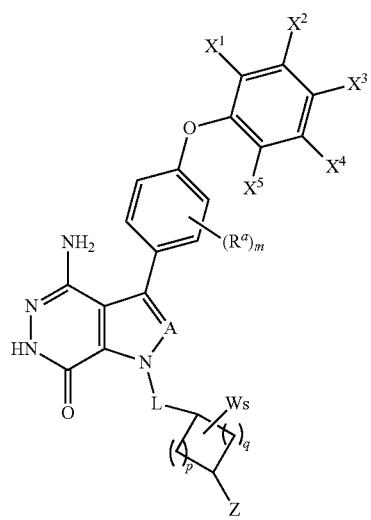

II wherein $X^1$, $X^2$, $X^3$, $X^4$, and $X^5$ are independently selected from the group consisting of hydrogen, halogen, cyano, nitro, hydroxyl, alkyl, and alkoxy;

each $R^a$ is independently selected from the group consisting of hydrogen, halogen, and alkoxyl;

A is selected from the group consisting of $CR^0$ and N; and wherein $R^0$ is selected from the group consisting of hydrogen, halogen, and alkyl;

L is alkylene, or absent;

each W is independently selected from the group consisting of halogen, hydroxyl, cyano, alkyl, and alkoxyl;

m =0, 1, 2, or 3;

p =1, 2, or 3;

q =0, 1, or 2;

s =0, 1, 2, or 3; and

Z is selected from the group consisting of —NHC(O)$R^{12}$ and —NHS(O)$_2R^{14}$; and wherein $R^{12}$ and $R^{14}$ are independently selected from the group consisting of alkyl, cycloalkyl, alkenyl, cycloalkenyl, and alkynyl.

18. A compound of formula (III), including tautomers, rotamers, geometric isomers, diastereomers, racemates, and enantiomers, a pharmaceutically acceptable salt, a solvate, or a hydrate thereof,

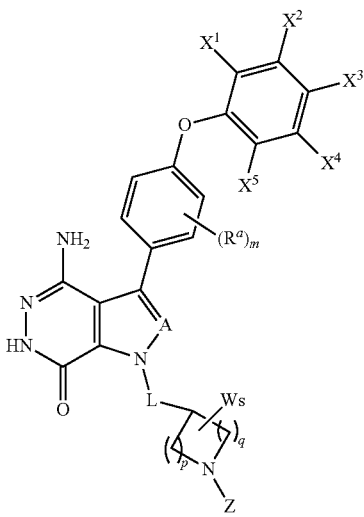

III wherein $X^1X^2$, $X^3$, $X^4$, and $X^5$ are independently selected from the group consisting of hydrogen, halogen, cyano, nitro, hydroxyl, alkyl, and alkoxy;

each $R^a$ is independently selected from the group consisting of hydrogen, halogen, and alkoxyl;

A is selected from the group consisting of $CR^0$ and N; and wherein $R^0$ is selected from the group consisting of hydrogen, halogen, and alkyl;

L is alkylene, or absent;

each W is independently selected from the group consisting of halogen, hydroxyl, cyano, alkyl, and alkoxyl;

m =0, 1, 2, or 3;

p =1, 2, or 3;

q =0, 1, or 2;

s =0, 1, 2, or 3; and

Z is selected from the group consisting of CN, —C(O)$R^{11}$, and —S(O)$_2R^{13}$; and wherein $R^{11}$, and $R^{13}$ are independently selected from the group consisting of alkyl, cycloalkyl, alkenyl, cycloalkenyl, and alkynyl; or Z is selected from the group consisting of —C(O)CH=CH$_2$, —C(O)CH=CHCH$_2$N(CH$_3$)$_2$, —C(O)CH=CHCH$_2$N(CH$_3$)(COOC(CH$_3$)$_3$); —C(O)CH=CHCH$_2$NH(CH$_3$), —C(O)CH$_2$CH$_3$, —C(O)CH$_2$CH$_2$CH$_3$,

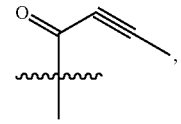 [SMILES: *C(=O)C#CC]

C(O)CH$_2$CH$_2$Cl,

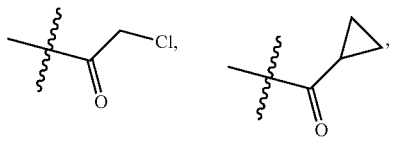 [SMILES: *C(=O)CCl ; *C(=O)C1CC1 ; ","]

—C(O)CH₂CN,
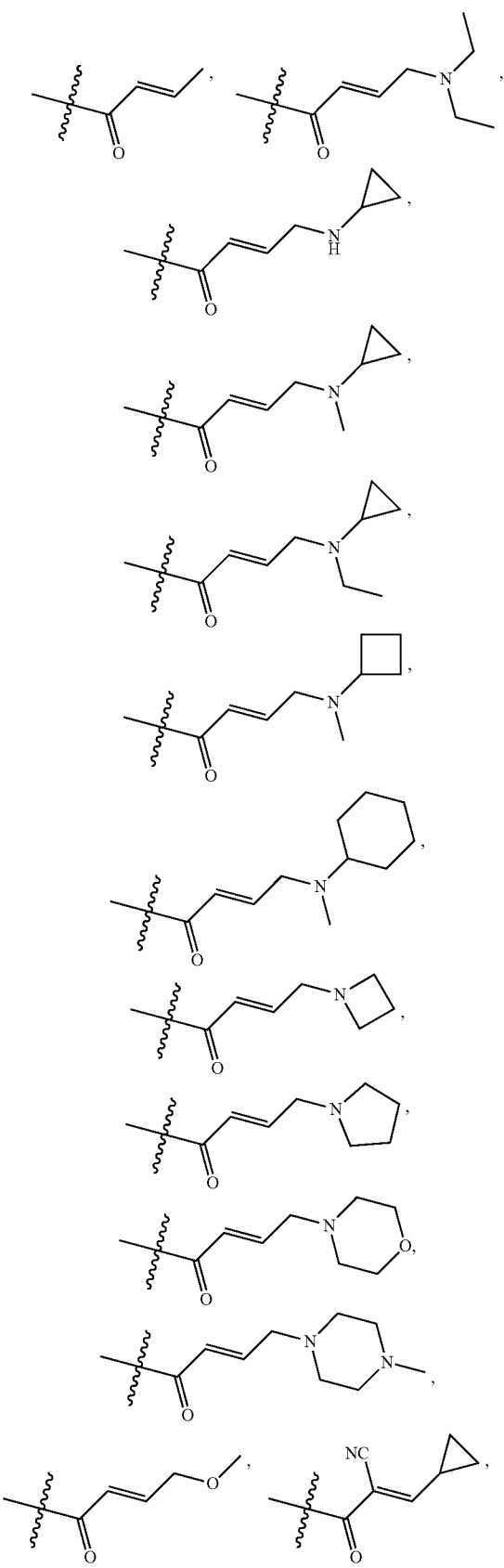
and
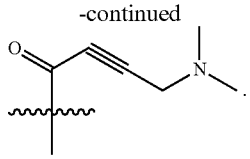
19. The compound of claim 18, a pharmaceutically acceptable salt, a solvate, or a hydrate thereof, wherein Z is from the group consisting of CN, —C(O)CH=CH₂, —C(O)CH=CHCH₂N(CH₃)₂, —C(O)CH=CHCH₂N(CH₃)(COOC(CH₃)₃); —C(O)CH=CHCH₂NH(CH₃), —C(O)CH₂CH₃, —C(O)CH₂CH₂CH₃
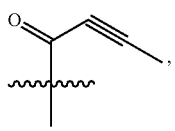
—C(O)CH₂CH₂Cl,
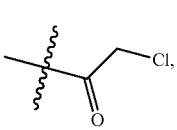 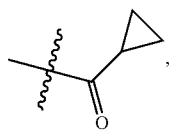
—C(O)CH₂CN,
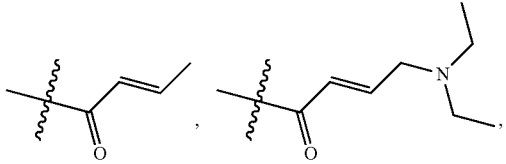
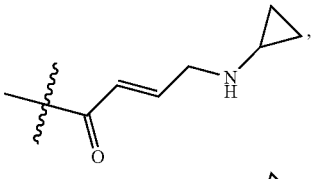
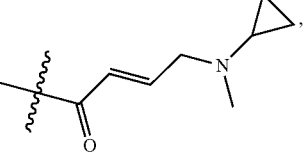
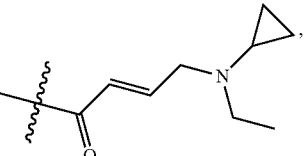
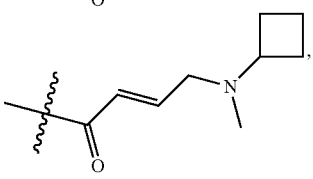

-continued

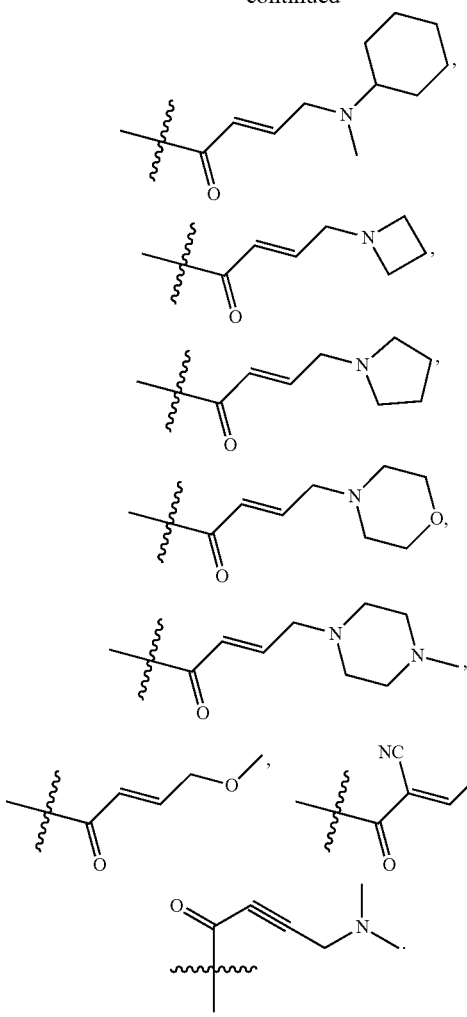

20. The compound of claim 1, a pharmaceutically acceptable salt, a solvate, or a hydrate thereof, wherein the compound is of formula (IV):

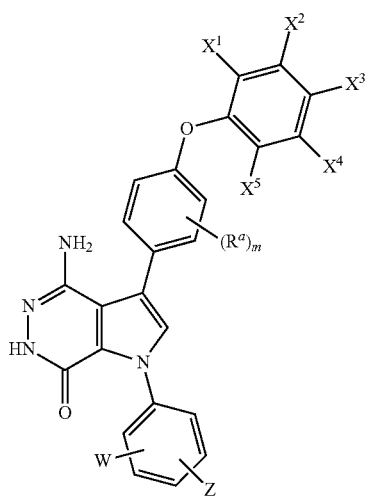

wherein $X^1$, $X^2$, $X^3$, $X^4$, and $X^5$ are independently selected from the group consisting of hydrogen, halogen, and alkoxyl; and
m =0, 1, 2, or 3, wherein W and Z are as defined in claim 1.

21. The compound of claim 1, a pharmaceutically acceptable salt, a solvate, or a hydrate thereof, wherein the compound is of formula (V):

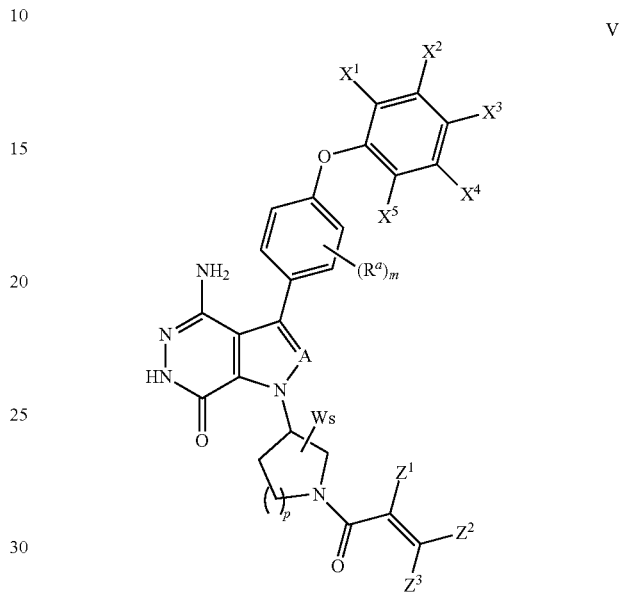

wherein $X^1$, $X^2$, $X^3$, $X^4$, and $X^5$ are independently selected from the group consisting of hydrogen, halogen, and alkoxyl; and
m =0, 1, 2, or 3.

22. The compound of claim 21, a pharmaceutically acceptable salt, a solvate, or a hydrate thereof, wherein A is N.

23. The compound of claim 21, a pharmaceutically acceptable salt, a solvate, or a hydrate thereof, wherein A is selected from the group consisting of CH, CF and CCl.

24. The compound of claim 21, a pharmaceutically acceptable salt, a solvate, or a hydrate thereof, wherein $Z^1$, $Z^2$ and $Z^3$ are H.

25. The compound of claim 21, a pharmaceutically acceptable salt, a solvate, or a hydrate thereof, wherein $Z^1$ and $Z^3$ are H, $Z^2$ is —$CH_2NR^{16}R^{17}$.

26. The compound of claim 21, a pharmaceutically acceptable salt, a solvate, or a hydrate thereof, wherein $Z^1$ and $Z^2$ join together to form a bond.

27. The compound of claim 21, a pharmaceutically acceptable salt, a solvate, or a hydrate thereof, wherein 3 or less than 3 of $X^1$, $X^2$, $X^3$, $X^4$, and $X^5$ are halogen.

28. The compound of claim 21, a pharmaceutically acceptable salt, a solvate, or a hydrate thereof, wherein $X^1$ is F.

29. The compound of claim 21, a pharmaceutically acceptable salt, a solvate, or a hydrate thereof, wherein $X^2$, $X^3$, and $X^4$ are hydrogen.

30. The compound of claim 21, a pharmaceutically acceptable salt, a solvate, or a hydrate thereof, wherein $X^5$ is selected from the group consisting of H, F and Cl.

31. A pharmaceutical composition comprising the compound of claim 1, and a pharmaceutically acceptable carrier.

* * * * *